US011987822B2

(12) United States Patent
Kahre

(10) Patent No.: US 11,987,822 B2
(45) Date of Patent: May 21, 2024

(54) SYNTHETIC REVERSE TRANSCRIPTASES AND USES THEREOF

(71) Applicant: SOLIS BIODYNE OÜ, Tartu (EE)

(72) Inventor: Olev Kahre, Tartu (EE)

(73) Assignee: SOLIS BIODYNE OÜ, Tartu (EE)

( * ) Notice: Subject to any disclaimer, the term of this patent is extended or adjusted under 35 U.S.C. 154(b) by 0 days.

(21) Appl. No.: 17/329,358

(22) Filed: May 25, 2021

(65) Prior Publication Data
US 2021/0388327 A1 Dec. 16, 2021

Related U.S. Application Data

(63) Continuation of application No. 16/092,753, filed as application No. PCT/IB2017/052114 on Apr. 12, 2017, now Pat. No. 11,046,940.

(60) Provisional application No. 62/321,692, filed on Apr. 12, 2016.

(51) Int. Cl.
C12N 9/12 (2006.01)
C12N 9/22 (2006.01)

(52) U.S. Cl.
CPC ............ C12N 9/1276 (2013.01); C12N 9/22 (2013.01); C12Y 207/07049 (2013.01); C12Y 301/26004 (2013.01); C07K 2319/85 (2013.01)

(58) Field of Classification Search
CPC ...... C12N 9/1276; C12N 9/22; C12N 9/1241; C12Y 207/07049; C12Y 301/26004; C07K 2319/85
See application file for complete search history.

(56) References Cited

U.S. PATENT DOCUMENTS

| | | | |
|---|---|---|---|
| 5,017,492 A | 5/1991 | Kotewicz et al. | |
| 5,244,797 A | 9/1993 | Kotewicz et al. | |
| 5,405,776 A | 4/1995 | Kotewicz et al. | |
| 5,668,005 A | 9/1997 | Kotewicz et al. | |
| 6,063,608 A | 5/2000 | Kotewicz et al. | |
| 8,618,253 B2 | 12/2013 | Cheung et al. | |
| 11,046,940 B2 | 6/2021 | Kahre | |
| 2003/0228616 A1 | 12/2003 | Arezi et al. | |
| 2011/0294674 A1 | 12/2011 | Cheung et al. | |
| 2012/0219945 A1 | 8/2012 | Lee | |
| 2014/0322789 A1* | 10/2014 | Lee | C12N 9/22 536/23.2 |

FOREIGN PATENT DOCUMENTS

| | | | |
|---|---|---|---|
| EP | 1554377 B1 | 11/2012 | |
| EP | 2639300 A2 | 9/2013 | |
| EP | 3443079 A1 | 2/2019 | |
| JP | 2008054599 A | 3/2008 | |
| WO | WO-2004/024749 A2 * | 3/2004 | |
| WO | WO-2004024749 A3 | 5/2005 | |
| WO | WO-2007022045 A2 | 2/2007 | |
| WO | WO-2017178986 A1 | 10/2017 | |

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36): 11643-50. (Year: 1999).*
Kisselev L., Polypeptide release factors in prokaryotes and eukaryotes: same function, different structure. Structure, 2002, vol. 10: 8-9. (Year: 2002).*
Enzymatics. M-MuLV Reverse Transcriptase. Product Information Sheet. P7040L Rev F. 2016. 2 pages.
Guo, et al. Defects in primer-template binding, processive DNA synthesis, and RNase H activity associated with chimeric reverse transcriptases having the murine leukemia virus polymerase domain joined to Escherichia coli RNase H. Biochemistry. Apr. 18, 1995;34(15):5018-29.
Hart, et al. Thermodynamic system drift in protein evolution. PLoS Biol. Nov. 11, 2014;12(11):e1001994. doi: 10.1371/journal.pbio. 1001994. eCollection 2014.
Howard, et al. Reconstitution and properties of homologous and chimeric HIV-1.HIV-2 p. 66.p. 51 reverse transcriptase. J Biol Chem. Dec. 5, 1991;266(34):23003-9.
"International Search Report and Written Opinion dated Jul. 4, 2017 for International PCT Patent Application No. IB-2017052114".
Invitrogen. SuperScript® One-Step RT-PCR with Platinum® Taq. Rev. 3.0. Oct. 8, 2013. 4 pages.
Julias, et al. Replication of phenotypically mixed human immunodeficiency virus type 1 virions containing catalytically active and catalytically inactive reverse transcriptase. J Virol. Jul. 2001;75(14):6537-46.
Lim, et al. Crystal structure of the moloney murine leukemia virus RNase H domain. J Virol. Sep. 2006;80(17):8379-89.
Misra, et al. An enzymatically active chimeric HIV-1 reverse transcriptase (RT) with the RNase-H domain of murine leukemia virus RT exists as a monomer. J Biol Chem. Apr. 17, 1998;273(16):9785-9.
PCT/IB2017/052114 International Search Report dated Jul. 4, 2017.
PCT/IB2017/052114 Written Opinion Report dated Jul. 4, 2017.
Post, et al. A large deletion in the connection subdomain of murine leukemia virus reverse transcriptase or replacement of the RNase H domain with Escherichia coli RNase H results in altered polymerase and RNase H activities. Biochemistry. Jun. 1, 1993;32(21):5508-17.
Post, et al. Human immunodeficiency virus type 2 reverse transcriptase activity in model systems that mimic steps in reverse transcription. J Virol. Jul. 2003;77(13):7623-34.

(Continued)

Primary Examiner — Iqbal H Chowdhury
(74) Attorney, Agent, or Firm — Wilson Sonsini Goodrich & Rosati

(57) ABSTRACT

The present disclosure provides non-natural reverse transcriptases for conducting reverse transcription. The non-natural reverse transcriptases herein may have increased thermostability and can conduct reverse transcription more efficiently than natural reverse transcriptases.

9 Claims, 5 Drawing Sheets
Specification includes a Sequence Listing.

(56) References Cited

OTHER PUBLICATIONS

Promega. Choosing the Right Reverse Transcriptase. Published 2013. 4 pages. http://www.promega.com/~/pdf/resources/pubhub/choosing-the-right-reverse-transcriptase/.
ThermoFisher. cDNA Synthesis from Transcripts with High Secondary Structure Using Thermo-X™ Reverse Transcriptase. Dec. 7, 2004. 3 pages. http://www.thermofisher.com/us/en/home/references/protocols/nucleic-acid-amplification-and-expression-profiling/cdna-protocol/cdna-synthesis-from-transcripts-with-high-secondary-structure-using-thermo-x-reverse-transcriptase.html.
ThermoFisher. ThermoScript™ Reverse Transcriptase. Catalog No.: 12236022. 2016. 3 pages. https://www.thermofisher.com/order/catalog/product/12236022.
U.S. Appl. No. 16/092,753 Notice of Allowance dated Mar. 2, 2021.
U.S. Appl. No. 16/092,753 Office Action dated Dec. 11, 2020.
U.S. Appl. No. 16/092,753 Office Action dated May 21, 2020.
Zhou, et al. Crystal structures of the reverse transcriptase-associated ribonuclease H domain of xenotropic murine leukemia-virus related virus. J Struct Biol. Mar. 2012;177(3):638-45. doi: 10.1016/j.jsb.2012.02.006. Epub Feb. 16, 2012.

* cited by examiner

Figure 1

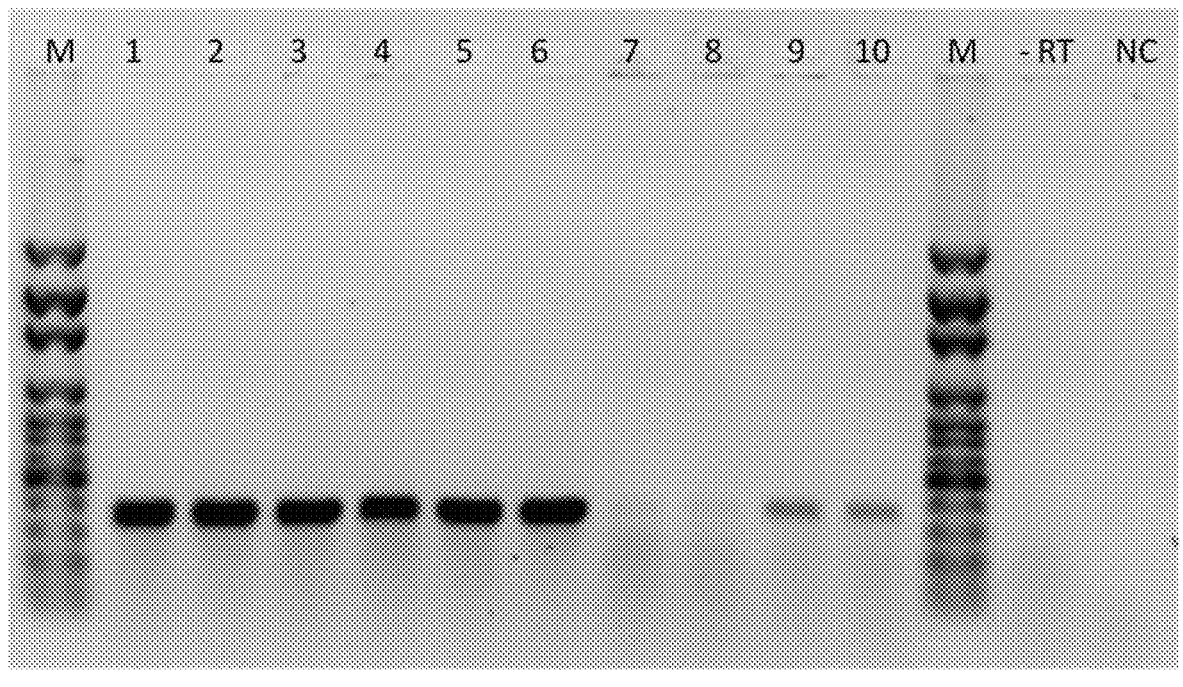

LANES

| | |
|---|---|
| M | 100 bp DNA Ladder Ready to Load (SBD) |
| 1. | wt_M-MLV_RNAse H+, SEQ ID NO: 1 |
| 2. | TAG_M-MLV_RNAse H+, SEQ ID NO: 13 |
| 3. | wt_M-MLV_Tth-RNAse H-, SEQ ID NO: 9 |
| 4. | TAG_M-MLV_Tth-RNAse H-, SEQ ID NO: 14 |
| 5. | wt_M-MLV_Tli-RNAse H II-, SEQ ID NO: 10 |
| 6. | TAG_M-MLV_Tli-RNAse H II-, SEQ ID NO: 15 |
| 7. | wt_HIV-1(p66)_Tth-RNAse H-, SEQ ID NO: 11 |
| 8. | TAG_HIV-1(p66)_Tth-RNAse H-, SEQ ID NO: 16 |
| 9. | wt_HIV-1(p66)_Tli-RNAse H II-, SEQ ID NO: 12 |
| 10. | TAG_HIV-1(p66)_Tli-RNAse H II-, SEQ ID NO: 17 |
| -RT | (control) reverse transcription reaction carried out without reverse transcriptase |
| NC | PCR negative control |

LANES

1. TAG_M-MLV_RNAse H+, SEQ ID NO: 13
2. wt_M-MLV_RNAse H+, SEQ ID NO: 1
3. TAG_M-MLV_Tth-RNAse H-, SEQ ID NO: 14
4. wt_M-MLV_Tth-RNAse H-, SEQ ID NO: 9
5. TAG_M-MLV_Tli-RNAse H II-, SEQ ID NO: 15
6. wt_M-MLV_Tli-RNAse H II-, SEQ ID NO: 10
7. TAG_HIV-1(p66)_Tth-RNAse H-, SEQ ID NO: 16
8. wt_HIV-1(p66)_Tth-RNAse H-, SEQ ID NO: 11
9. TAG_HIV-1(p66)_Tli-RNAse H II-, SEQ ID NO: 17
10. wt_HIV-1(p66)_Tli-RNAse H II-, SEQ ID NO: 12

LANES

M     100 bp DNA Ladder Ready to Load (SBD)

RT1    TAG_M-MLV_RNAse H+, SEQ ID NO: 13

RT2    TAG_M-MLV_Tth_RNAse H-, SEQ ID NO: 14

RT3    TAG_M-MLV_Tli_RNAse H II-, SEQ ID NO: 15

-RT    Control were reverse transcription reaction was carried out without any reverse transcriptase NC    PCR negative control

LANES

1. Total RNA input 1 μg
2. Total RNA input 100 ng
3. Total RNA input 10 ng
4. Total RNA input 1 ng
5. Total RNA input 100 pg
6. Total RNA input 10 pg
7. -RT control (no RT enzyme)

LANES

1. Total RNA input 1 μg
2. Total RNA input 100 ng
3. Total RNA input 10 ng
4. Total RNA input 1 ng
5. Total RNA input 100 pg
6. Total RNA input 10 pg
7. -RT control (no RT enzyme)

SYNTHETIC REVERSE TRANSCRIPTASES AND USES THEREOF

CROSS-REFERENCE

This application is a continuation of U.S. patent application Ser. No. 16/092,753, filed Oct. 10, 2018, now U.S. Pat. No. 11,046,940, issued Jun. 29, 2021, which is a U.S. National Stage entry under 35 U.S.C. § 371 of International Patent Application No.: PCT/IB2017/052114, filed Apr. 12, 2017, which claims the benefit of U.S. Provisional Application No. 62/321,692, filed Apr. 12, 2016, which applications are each incorporated herein by reference.

The instant application contains a Sequence Listing which has been submitted electronically in ASCII format and is hereby incorporated by reference in its entirety. Said ASCII copy, created on Jan. 28, 2019, is named 39328-703_831_SL.txt and is 115,236 bytes in size.

BACKGROUND

Retroviruses replicate their genomes through reverse transcription, which is a step-wise process that leads to the synthesis of double-stranded DNA from a single stranded RNA molecule. Retroviral reverse transcription is generally accomplished by a viral reverse transcriptase that possesses DNA polymerase activity and ribonuclease (RNase) activity. The DNA polymerase has RNA-dependent DNA polymerase activity and may also possess DNA-dependent DNA polymerase activity, albeit with variable efficiency. The first step of reverse transcription is catalyzed by an RNA-dependent DNA polymerase that synthesizes single-stranded DNA using RNA as a template. The RNA portion of the resulting DNA-RNA hybrid is then degraded by the RNase H portion of the reverse transcriptase (RT). The resulting single-stranded DNA may be used as a template to produce double-stranded DNA, a process catalyzed by DNA-dependent DNA polymerase activity of the viral RT, if present, or by an exogenous DNA-dependent DNA polymerase, such as a DNA polymerase present in the host cell.

In a viral RT, the RNase domain (e.g., RNase H) is generally linked to the DNA polymerase domain. However, ribonucleases can also exist independently of reverse transcriptases. For example, cellular RNase Hs, which have been identified in various microorganisms such as bacteria (e.g., mesophilic and thermophilic) and archaea (e.g., thermophilic), can exist as independent molecules.

Natural viral RTs can be inefficient for various reasons. RTs, in some cases, can degrade an RNA template before the first strand reaction is initiated or completed, e.g., due to the intrinsic ribonuclease activity present in the enzyme. In addition, mis-priming of the RNA template molecule can lead to the introduction of errors in the cDNA first strand. Reverse transcription may be especially challenging when the template RNA has a high degree of secondary structure, which can occur, for example, when complementary regions within an RNA molecule hybridize to form double-stranded RNA. Generally, the detrimental effects of RNA secondary structure may be reduced by heating the RNA in a pre-incubation step prior to the initiation of reverse transcription.

There is a need in the art for a new RT with improved specific activity, efficiency, reaction speed, and/or stability, particularly at elevated temperatures. Novel approaches for generating new RTs are also needed.

SUMMARY

This disclosure provides non-natural reverse transcriptases (non-natural "RTs") with enhanced properties such as the ability to conduct reverse transcription at elevated temperatures with a high specific activity. This disclosure also provides methods of using the non-natural RTs, methods of generating the non-natural RTs and kits containing the non-natural RTs as one of the components of the kit.

In an aspect, the present disclosure provides a non-natural reverse transcriptase comprising a first domain and a second domain, wherein (a) the first domain comprises an enzyme with an amino acid sequence at least about 80% identical to an amino acid sequence of an enzyme from a first organism, and (b) the second domain comprises a modified ribonuclease polypeptide with an amino acid sequence between 50% and 99.9% identical to an amino acid sequence of a wild-type ribonuclease from a second organism; wherein the second organism is different from the first organism and wherein the modified ribonuclease polypeptide has reduced ribonuclease activity relative to ribonuclease activity of the wild-type ribonuclease from the second organism.

In an aspect, the present disclosure provides a non-natural reverse transcriptase comprising a first domain and a second domain, wherein (a) the first domain comprises an enzyme with an amino acid sequence at least about 80% identical to an amino acid sequence of an enzyme from a first organism, and (b) the second domain comprises a modified ribonuclease polypeptide with an amino acid sequence between 50% and 97% identical to an amino acid sequence of a wild-type ribonuclease from a second organism; wherein the second organism is different from the first organism and wherein the modified ribonuclease polypeptide has reduced ribonuclease activity relative to ribonuclease activity of the wild-type ribonuclease from the second organism.

In an aspect, the present disclosure provides a non-natural reverse transcriptase comprising a first domain and a second domain wherein (a) the first domain comprises an enzyme, and (b) the second domain comprises a modified ribonuclease polypeptide; wherein the first and second domains are not derived from the same organism and wherein the modified ribonuclease polypeptide comprises an amino acid sequence designed to reduce activity of the modified ribonuclease polypeptide when compared to a naturally-occurring version of the modified ribonuclease polypeptide.

In some embodiments, the modified ribonuclease polypeptide comprises an RNase H polypeptide. In some embodiments, the RNase H polypeptide comprises a mutated RNase H domain. In some embodiments, the mutated RNase H domain comprises at least one mutation in an active site. In some embodiments, the at least one mutation in the active site decreases RNase H activity of the RNase H domain relative to an un-mutated version of the RNase H domain. In some embodiments, the at least one mutation is an amino acid substitution, insertion, or deletion. In some embodiments, the non-natural reverse transcriptase has at most 75%, 50%, 25%, 10%, 1%, 0.1%, or less of the ribonuclease activity of a wild type version of the modified ribonuclease polypeptide.

In some embodiments, the first domain is linked to the second domain. In some embodiments, the first domain is linked to the N-terminus of the modified ribonuclease polypeptide. In some embodiments, a non-natural reverse transcriptase provided herein further comprises a third polypeptide. In some embodiments, the third polypeptide comprises a peptide tag that confers thermal stability to the non-natural reverse transcriptase. In some embodiments, the third polypeptide is positioned at the N-terminus of the non-natural reverse transcriptase. In some embodiments, the third polypeptide is positioned at the C-terminus of the non-natural reverse transcriptase. In some embodiments, the non-natural reverse transcriptase further comprises a fourth polypeptide. In some embodiments, the fourth polypeptide comprises a peptide tag that confers thermal stability to the non-natural reverse transcriptase. The fourth polypeptide can be positioned at the N-terminus or at the C-terminus.

In some embodiments, the enzyme comprises a polymerase domain or a variant thereof. In some embodiments, the enzyme comprises a polymerase and the polymerase is derived from a virus, an avian virus, a human virus, a murine virus, a retrovirus, a lentivirus, or a gammaretrovirus. In some embodiments, the polymerase domain or variant thereof is derived from a viral reverse transcriptase selected from the group consisting of: Moloney Murine Leukemia Virus (M-MLV) reverse transcriptase, Rous Sarcoma Virus (RSV) reverse transcriptase, Avian Myeloblastosis Virus (AMV) reverse transcriptase, Myeloblastosis Associated Virus (MAV) reverse transcriptase, Rous Associated Virus (RAV) reverse transcriptase, and Human Immunodeficiency Virus 1 (HIV-1) reverse transcriptase. In some embodiments, the enzyme comprises a polymerase domain or a variant thereof, and the polymerase domain is derived from a virus, an avian virus, a human virus, a murine virus, a retrovirus, a lentivirus, or a gammaretrovirus. In some embodiments, the polymerase or polymerase domain or variant thereof comprises an amino acid sequence of (or is derived from) a polymerase domain of a viral reverse transcriptase selected from the group consisting of Moloney Murine Leukemia Virus (M-MLV) reverse transcriptase, Rous Sarcoma Virus (RSV) reverse transcriptase, Avian Myeloblastosis Virus (AMV) reverse transcriptase, Myeloblastosis Associated Virus (MAV) reverse transcriptase, Rous Associated Virus (RAV) reverse transcriptase, and Human Immunodeficiency In some embodiments, the enzyme is derived from a polymerase and the polymerase is a DNA polymerase. In some embodiments, the enzyme is derived from a polymerase and the polymerase is an RNA-dependent DNA polymerase. In some embodiments, the enzyme is derived from a polymerase and the polymerase is a DNA-dependent DNA polymerase. In some embodiments, the polymerase is derived from an M-MLV reverse transcriptase. In some embodiments, the polymerase is derived from HIV-1 reverse transcriptase. In some embodiments, the enzyme is a polymerase selected from the group consisting of DNA polymerase, RNA-dependent DNA polymerase, and DNA-dependent DNA polymerase. In some embodiments, the polymerase is derived from a viral reverse transcriptase. In some embodiments, the viral reverse transcriptase is selected from the group consisting of M-MLV reverse transcriptase and HIV-1 reverse transcriptase.

In some embodiments, the modified ribonuclease polypeptide is derived from a bacterial RNase H or an archaeal RNase H. In some embodiments, the modified ribonuclease polypeptide is derived from an extremophile organism. In some embodiments, the modified ribonuclease polypeptide is derived from a polypeptide selected from the group consisting of: *Pyrococcus furiosus* RNase H, *Pyrococcus horikoshi* RNase H, *Thermococcus litoralis* RNase H II, *Thermus thermophilus* RNase H, RNase H, RNase HI, Rnase HII, RNase HIII, and *Escherichia coli* RNase H. In some embodiments, the modified ribonuclease polypeptide is derived from an organism of the genus *Thermus*. In some embodiments, the modified ribonuclease polypeptide is derived from *Thermus thermophilus* RNase H. In some embodiments, the modified ribonuclease polypeptide comprises an amino acid sequence at least 85%, 90%, or 95% identical to SEQ ID NO: 21. In some embodiments, the modified ribonuclease polypeptide is derived from an organism of the genus *Thermococcus*. In some embodiments, the modified ribonuclease polypeptide is derived from *Thermococcus litoralis* RNase H. In some embodiments, the modified ribonuclease polypeptide comprises an amino acid sequence at least 85%, 90%, or 95% identical to SEQ ID NO: 22. In some embodiments, the modified ribonuclease polypeptide comprises an active site comprising a mutation at at least one of residues 14 (D), 52 (E), 74 (D) and 139 (D) of SEQ ID NO: 7. In some embodiments, the modified ribonuclease polypeptide comprises an active site comprising a mutation at at least one of residues 7 (D), 8 (E), 105 (D) and 135 (D) of SEQ ID NO: 8.

In some embodiments, the non-natural reverse transcriptase retains greater than 50% of its reverse transcriptase activity at temperatures above 55° C. In some embodiments, the non-natural reverse transcriptase retains greater than 50% of its reverse transcriptase activity after incubation at a temperature of least about 55° C. or higher for at least 15 minutes. In some embodiments, the non-natural reverse transcriptase retains reverse transcriptase activity after incubation at a temperature of least about 60° C. or higher for at least 15 minutes. In some embodiments, the non-natural reverse transcriptase retains reverse transcriptase activity after incubation at a temperature of least about 65° C. or higher for at least 15 minutes. In some embodiments, the non-natural reverse transcriptase retains reverse transcriptase activity after incubation at a temperature between 40° C. and 65° C., at a temperature between 60° C. and 65° C., at a temperature between 55° C. and 60° C. or at a temperature between 55° C. and 75° C. In some cases, such incubation is for 15 minutes, 30 minutes, 1 hour, or longer. In some cases, such incubation lasts between 15 minutes and 2 hours, between 15 minutes and 1 hour, between 30 minutes and 2 hours, or between 60 minutes and 2 hours.

In some embodiments, the non-natural reverse transcriptase comprises an amino acid sequence at least 85% identical to SEQ ID NO: 9, SEQ ID NO: 10, SEQ ID NO: 11, SEQ ID NO: 12, SEQ ID NO: 14, SEQ ID NO: 15, SEQ ID NO: 16 or SEQ ID NO: 17. In some embodiments, the non-natural reverse transcriptase has a specific activity of at least about 30,000 U/µg.

In an aspect, the present disclosure provides a non-natural reverse transcriptase comprising (a) a first domain comprising an enzyme, and (b) a second domain comprising a ribonuclease polypeptide having ribonuclease activity; wherein the non-natural reverse transcriptase retains at least 25% of its reverse transcriptase activity at about 37° C. after incubation at a temperature of at least about 60° C. for at least 10 minutes.

In some embodiments, the first domain is linked to the second domain.

In some embodiments, the specific activity of the non-natural reverse transcriptase is greater than 450 U/µg. In some embodiments, the specific activity of the non-natural reverse transcriptase is greater than 10,000 U/µg. In some embodiments, the specific activity of the non-natural reverse transcriptase is greater than 20,000 U/µg. In some embodiments, the specific activity of the non-natural reverse transcriptase is greater than 30,000 U/µg.

In some embodiments, the second domain is derived from an extremophile organism.

In an aspect, the present disclosure provides a kit for complementary DNA (cDNA) synthesis comprising any non-natural reverse transcriptase provided herein. In some cases, the kit further comprises a DNA-dependent DNA polymerase in a separate container from the non-natural reverse transcriptase. In some cases, the kit further comprises a DNA-dependent DNA polymerase mixed in the same container as the non-natural reverse transcriptase.

In some embodiments, the kit further comprises a primer to initiate cDNA synthesis. In some embodiments, the primer is an oligo(dT) primer. In some embodiments, the kit further comprises dNTPs. In some embodiments, the kit further comprises a reaction buffer. In some embodiments, the reaction buffer comprises divalent metal ions. In some embodiments, the divalent metal ions are Mg2+ or Mn2+.

In some embodiments, the kit is stored at room temperature.

In an aspect, the present disclosure provides a method for synthesizing complementary DNA (cDNA), comprising (a) providing an RNA molecule as a template for cDNA synthesis, (b) providing a primer to initiate cDNA synthesis from the RNA molecule, and (c) synthesizing cDNA initiated by the primer from the template using any non-natural reverse transcriptase provided herein.

In an aspect, the present disclosure provides a method of synthesizing a reverse transcriptase comprising linking an enzyme to a ribonuclease polypeptide, wherein the enzyme and the ribonuclease are from different organisms, and wherein the ribonuclease is specifically selected to increase the thermal stability of the reverse transcriptase.

In some embodiments, the ribonuclease is derived from an extremophile RNase. In some embodiments, the ribonuclease is derived from a bacterial RNase or an archaeal RNase H. In some embodiments, the ribonuclease is derived from an RNase selected from the group consisting of: *Pyrococcus furiosus* RNase H, *Pyrococcus horikoshi* RNase H, *Thermococcus litoralis* RNase H II, *Thermus thermophilus* RNase H, and *Escherichia coli* RNase H. In some embodiments, the RNase H is *Thermus thermophilus* RNase H. In some embodiments, the RNase H is *Thermococcus litoralis* RNase H.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows DNA product from reverse transcription performed with non-natural reverse transcriptases provided herein and subsequent amplification via a DNA polymerase.

DETAILED DESCRIPTION

Overview

Figure 2:
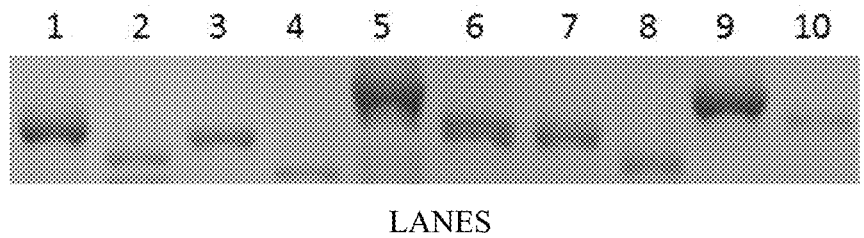
FIG. 2 shows the molecular weight of non-natural reverse transcriptases on a protein gel.

The present disclosure provides compositions comprising non-natural chimeric RTs, methods for conducting reverse transcription using the non-natural RTs, methods for designing and generating the non-natural RTs and kits comprising the non-natural RTs. Generally, the non-natural RTs provided herein comprise at least two domains selected to impart certain benefits on the molecule (or complex of molecules, referred to interchangeably as "molecule complex") as a whole. The resulting molecule (or molecule complex) may have features such as particularly high thermal stability, specific activity, sensitivity, efficiency, reaction speed, or any combination thereof. Such features may also be particularly robust in comparison to naturally-occurring RTs.

In some examples, a RT provided herein comprises (a) a reverse transcriptase domain specifically selected from a species of virus known to have some amount of RNA-dependent DNA polymerase activity (e.g., weak, moderate, or high) and (b) a RNase domain (e.g., RNase H domain) selected from a species of bacteria or archaea known to have high temperature tolerance or other attributes (e.g., extremophile bacterial RNase H, extremophile archaean RNase H). In some examples, a RT provided herein comprises (a) a reverse transcriptase domain specifically selected from a species of virus known to have efficient RNA-dependent DNA polymerase activity (e.g., M-MLV) and (b) a RNase domain (e.g., RNase H domain) selected from a species of bacteria or archaea known to have high temperature tolerance or other attributes (e.g., extremophile bacterial RNase H, extremophile archaean RNase H). The RNA-dependent DNA polymerase activity may be determined by any suitable assay or comparison to any accepted standard or metric, for example, a specific activity measurement. In some cases, the endogenous RNase domain of the RT may possess RNase activity (e.g., RNase H activity); while, in others, the RT possesses minimal or no RNase activity. A decrease or lack of RNase activity in an RT can result, for example, from inactivating mutations introduced into the RNase domain. An RT provided herein may also possess DNA-dependent DNA polymerase activity; while, in other cases, the RT possesses minimal or no DNA-dependent polymerase activity. In some cases, the non-natural RT possesses both RNA-dependent and DNA-dependent polymerase activity. In some cases, the RT possesses RNA-dependent DNA polymerase activity but not DNA-dependent polymerase activity.

The RTs provided herein may have robust thermal stability, which may provide a number of advantages. Thermal stability can refer to the stability of the structure or activity of a protein as a function of temperature. Generally, increases in temperature can result in changes to the structure of a protein which consequently may change properties of the protein related to its structure, for example enzymatic activity in the case of enzymes and/or the ability to interact with binding partners. RTs with increased thermal stability, for example, may enable reduction of the number of steps required to complete reverse transcription, thereby reducing the total reaction time, or the time from single-stranded RNA to double-stranded cDNA. RNA templates, particularly RNA templates with high degrees of secondary structure, may require a pre-incubation step at an elevated temperature in order to denature the RNA, followed by a cooling step in order to cool the sample to a temperature that would not interfere with the function of a non-thermally stable RT. In contrast, a thermal-stable RT provided herein can be included with a sample during the pre-incubation step; and the cooling step may be skipped since the RT can still function at the higher temperature. Another advantage of the RTs provided herein is that they may be used to conduct reverse transcription at elevated temperatures.

The non-natural RTs provided herein may have particularly high RNA-directed DNA polymerase specific activity. For example, a non-natural RT provided herein may have a RNA-directed DNA polymerase specific activity of at least 450 U/µg. In some cases, a non-natural RT provided herein may have a RNA-directed DNA polymerase specific activity of at least 100 U/µg, at least 500 U/µg, at least 1,000 U/µg, at least 5,000 U/µg, at least 10,000 U/µg, at least 15,000 U/µg, at least 20,000 U/µg, at least 25,000 U/µg, at least 30,000 U/µg, or greater. In some cases, the specific activity may be particularly high in comparison to a naturally-occurring RT. For example, a non-natural RT provided herein may have greater than 3-fold specific activity compared to its wild-type form. In some cases, a non-natural RT provided herein may have at least 5-fold, 10-fold, 20-fold, 30-fold, 40-fold, 50-fold, at least 100-fold, at least 150-fold, or greater specific activity compared to its wild-type form.

The non-natural RTs provided herein may also display highly efficient reverse transcription or the conversion of RNA into cDNA. The non-natural RTs may more efficiently convert mRNA into cDNA in reverse transcription due to enhanced thermal stability, decreased ribonuclease activity and/or increased polymerase activity compared to wild-type RTs. In some cases, a non-natural or chimeric reverse transcriptase provided herein may have an efficiency that is at least about 0.1-fold, 0.2-fold, 0.3-fold, 0.4-fold, 0.5-fold, 1-fold, 2-fold, 3-fold, 4-fold, 5-fold, 10-fold or greater than 10-fold the efficiency of its wild-type or natural form. In some cases, a non-natural or chimeric reverse transcriptase provided herein may have an efficiency that is at least about 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 250-fold, 300-fold, 350-fold, 400-fold, 450-fold, 500-fold, or greater than 500-fold the efficiency of its wild-type or natural form. In some cases, a non-natural or chimeric reverse transcriptase provided herein may have an efficiency that is between 5-fold and 400-fold the efficiency of its wild-type of natural form.

The compositions provided herein include compositions comprising nucleic acids encoding a non-natural chimeric RT provided herein. In some cases, the nucleic acids encode an entire RT protein. In some cases, the nucleic acids encode a domain (e.g., polymerase domain, RNase domain) of an RT protein.

Domains

Generally, the non-natural chimeric RTs provided herein comprise at least two domains, such as at least one DNA polymerase domain (e.g., DNA-dependent DNA polymerase or RNA-dependent DNA polymerase) and at least one RNase domain. The term "domain," as used herein, generally refers to a discrete set or sequence of units (e.g., nucleic acids, amino acids, etc) within a polymer such as a polynucleotide, polypeptide or other macromolecule. The discrete set of units can be a consecutive sequence of units (e.g., units at positions 4-10 of a macromolecule). In some cases, the discrete set may also comprise units (e.g., amino acids) that are disparately or sporadically positioned within the macromolecule (e.g, positioned at positions 4, 7, 8, 9, 11, and 12 of the macromolecule). A domain may also refer to a region of a macromolecule that is close together in three-dimensional space (e.g., a binding domain), often due to folding (e.g., protein folding); such region may or may not be associated with a specific sequence of units, e.g., amino acid sequence. A domain often may be associated with a particular activity or function, such as DNA polymerase activity or RNase activity. In some cases, a domain is associated with more than one activity or function, e.g., both RNA-dependent DNA polymerase activity and DNA-dependent DNA polymerase activity. In some cases, a particular domain may refer to a discrete set or sequence of units (e.g., amino acids) with no particular function.

A polypeptide domain provided herein may be encoded by a single polynucleotide. A polypeptide domain can be encoded by a portion of a polynucleotide that encodes other domains within the polypeptide.

The RTs provided herein may have any number of domains, e.g., at least about 1 domain, at least about 2 domains, at least about 3 domains, at least about 4 domains, at least about 5 domains, at least about 6 domains, at least about 7 domains, at least about 8 domains, at least about 9 domains, at least about 10 domains, at least about 20 domains, or more than 20 domains. In some cases, two or more domains within the RT are identical. In some cases, two or more domains within the RT have >50% sequence identity. In some cases, two or more domains in the RT have a different function, sequence, and/or structure.

Two or more domains within a RT provided herein may be present within a single polypeptide (e.g., as a monomeric polypeptide). In some cases, two or more domains of an RT provided herein are present within multiple polypeptides, or multiple subunits. For example, at least one domain within a RT provided herein is present in one subunit of the RT and at least one domain within the RT is located in a different subunit. The subunits can associate together to form a single complex. However, in some cases, the subunits are located in different complexes. For example, a DNA polymerase domain (e.g., RNA-dependent DNA polymerase) may be present in one unit of a complex and the RNase domain may be present in a different unit within a complex, or in a separate molecule or complex altogether.

Chimeric Reverse Transcriptases

The non-natural RTs provided herein are generally chimeric proteins and thus may be referred to as "chimeric RTs". As used herein, the terms "chimeric protein" or "chimeric polypeptide" may be used interchangeably to refer to a protein comprising two or more polypeptide sequences or domains that are not naturally present in the same polypeptide. In some cases, the two or more polypeptide sequences or domains may be from the same type of organism. In some cases, the two or more polypeptide sequences or domains may be from at least two different types of organisms. In some cases, the two or more polypeptide sequences or domains may be derived from two polypeptide domains that occur in nature, except that one or more of the peptides is altered so as not to markedly resemble a naturally-occurring domain (e.g., by mutation). For example, the altered peptide can be less than 100%, less than 90%, less than 80%, less than 70%, less than 60%, less than 50%, less than 40%, less than 30%, less than 20%, less than 10% or less than 5% identical to the naturally-occurring domain. In some examples, the two or more polypeptide sequences or domains are derived from a virus. In some instances, the two or more polypeptide sequences or domains derived from a virus are derived from the same family of virus (e.g., retrovirus), or the same genus of virus (e.g., gammaretrovirus), or the same type of virus (e.g., Murine Leukemia Virus (MLV)); or the same strain or subtype of virus (e.g., Moloney Murine Leukemia Virus (M-MLV or M-MuLV)). In some cases, the two or more polypeptide sequences or domains are derived from the same domain (e.g., biological classification, phylogeny) (e.g., Archaea). In some cases, the two or more polypeptide sequences or domains are derived from the same kingdom (e.g., Euryarchaeota). In some cases, the two or more polypeptide sequences or domains are derived from the same family (e.g., Thermaceae, Thermococcaceae); from the same genus (e.g., *Thermus, Thermococcus*); or from the same species (e.g., *Thermus thermophilus, Thermococcus litoralis*). In some cases, the two or more polypeptide sequences or domains are derived from the same class (e.g., Deinococci, Thermocci); or from the same order (e.g., Thermales, Thermococcales).

In some embodiments, the two or more polypeptide sequences or domains within the RTs provided herein are derived from different organisms (e.g., one may be from a virus, the other from a bacterium or archaeon). In some cases, the two or more polypeptide sequences or domains are derived from different kingdoms; from different phylums; from different classes; from different orders; from different families; from different genuses; from different species; from different strains; or from different subtypes.

In some cases, the RTs provided herein comprise at least one domain or sequence derived from a retrovirus (e.g., MLV, M-MLV, AMV) and at least one domain or sequence derived from a bacterium or archaeon (e.g., extremophile bacterium, extremophile archaeon, *Thermus* bacterium, *Thermococcus archaea, T. thermophilus, T. thermophilus* HB8, *T. litoralis*, etc), in any combination thereof. In various embodiments, the DNA polymerase domain (or domains) is derived from a virus and the RNase domain (or domains) is derived from a bacterium or archaeon. The RT may comprise an M-MLV domain (e.g., an M-MLV DNA polymerase domain) and an extremophile domain (e.g., RNase domain from an extremophilic bacterium or from an extremophilic archaeon). In some cases, the RT may comprise a MLV domain (e.g., an MLV DNA polymerase domain, an M-MLV DNA polymerase domain) and a *Thermus* bacterium domain (e.g., RNase from *T. Thermophilus*). In some embodiments, the RTs provided herein comprise at least one domain or sequence derived from a virus (e.g., retrovirus, e.g., MLV, M-MLV, AMV) and at least one domain or sequence derived from an archaeon (e.g., extremophile archaeon, *T. litoralis*) in any combination. Generally, the DNA polymerase domain (or domains) is derived from a virus. Generally, the RNase domain (or domains) is derived from a bacterium or archaeon organism. For example, the RT may comprise a MLV domain (e.g., an MLV DNA polymerase domain, particularly an M-MLV DNA polymerase domain) and an RNase domain derived from a *Thermus* bacterium (e.g., RNaseH domain from *T. Thermophilus*). For further example, the RTs provided herein may comprise a MLV domain (e.g., an MLV DNA polymerase domain) and an RNase domain derived from a *Thermococcus* archaeon (e.g., RNaseH domain from *T. litoralis*).

An RNase domain within an RT provided herein may be selected because it is known or suspected to share certain structural and/or functional features with an RNase from a different organism (or strain, species, genus, family, order, class, domain, etc.). In some cases, the RNase domain is derived from an organism (or strain, species, genus, family, order, class, domain, etc.) different from the DNA polymerase domain within the RT but is known or suspected to share certain structural and/or functional features with the RNase of the wild-type or natural RT. In some instances, a *T. thermophilus* RNase H may be homologous to an RNase (e.g., RNase H) domain from M-MLV in terms of sequence and/or structure (e.g., 3D structure). For example, the RNase (e.g., RNase H) domain of an RT provided herein may be a *T. thermophilus* RNase and the DNA polymerase domain of the RT may be from M-MLV. In another example, the *T. thermophilus* RNase may be combined with an HIV DNA polymerase, or other DNA polymerase provided herein. In still another example, an *E. Coli* RNase may be combined with an M-MLV or HIV DNA polymerase.

In some cases, an RNase domain within an RT provided herein may be selected because it is known or suspected to possess dissimilar structural and/or functional features compared to an RNase from a different organism (or strain, species, genus, family, order, class, domain, etc.). In some cases, the RNase domain is derived from an organism (or strain, species, genus, family, order, class, domain, etc.) different from the DNA polymerase domain within the RT but is known or suspected to possess dissimilar structural and/or functional features with the RNase of the wild-type or natural RT. For example, *T. litoralis* RNase H II may lack homology to an RNase H from M-MLV or HIV in terms of sequence and/or structure (e.g., 3D structure). For example, the RNase H domain of an RT provided herein may be a *T. litoralis* RNase H II and the DNA polymerase domain of the RT may be from M-MLV or HIV.

An RT provided herein may comprise a retroviral DNA polymerase domain and an RNase domain derived from a cellular microorganism that exhibits a certain feature, such as heat tolerance or thermal stability. The microorganism may be a thermophilic microorganism such as a thermophilic bacterium or archaeon (e.g., *T. thermophilus* or *T. litoralis*). The resulting chimeric RT may have enhanced thermostability when compared to a naturally-occurring RT, or to a RT in which all of the domains are derived from a retrovirus. Additional thermostable microorganisms include, but are not limited to, *Thermococcus gammatolerans, Thermus flavus, Thermus ruber, Thermus thermophilus, Bacillus stearothermophilus, Thermus lacteus, Thermus rubens, Thermotoga maritima,* and *Methanothermus fervidus*. In some cases, the thermostable microorganism is radiation-resistant.

In some cases, a chimeric reverse transcriptase may comprise at least two domains that are derived from viruses. For example, the RT may comprise the polymerase domain of M-MLV RT linked to the ribonuclease domain of HIV-1 RT. Conversely, a chimeric RT may comprise the polymerase domain of HIV-1 RT linked to the ribonuclease domain of M-MLV RT or AMV RT. In another example, a chimeric reverse transcriptase may comprise the polymerase domain of AMV RT linked to the ribonuclease domain of M-MLV RT or HIV-1 RT.

In some cases, the polymerase domain and/or the ribonuclease domain can be truncated at either an N-terminus or a C-terminus. Certain amino acids at the N-terminus or C-terminus of a domain may not be necessary for function and/or structure, and removal of these amino acids may help with, for example, formation (e.g., folding) of the chimeric protein while minimally affecting the function of the chimeric protein. In some cases, the polymerase domain and/or the ribonuclease domain can be truncated at the N-terminus relative to the wild-type sequence of the domain. The polymerase domain and/or ribonuclease domain derived from a viral reverse transcriptase can be truncated by at least 1 amino acid (e.g., at least 2, 3, 4, 5, 6, 7, 8 amino acids or more than 8 amino acids) at the N-terminus relative to the wild-type sequence of the domain. The ribonuclease domain derived from a bacterial or archaeal RNase can be truncated by at least 1 amino acid (e.g., at least 2, 3, 4, 5, 6, 7, 8 amino acids or more than 8 amino acids) at the N-terminus relative to the wild-type sequence of the domain. In some cases, the polymerase domain and/or the ribonuclease domain can be truncated at the C-terminus relative to the wild-type sequence of the domain. In some cases, the polymerase domain and/or ribonuclease domain derived from a viral reverse transcriptase can be truncated by at least 1 amino acid (e.g., at least 2, 3, 4, 5, 6, 7, 8 amino acids or more than 8 amino acids) at the C-terminus relative to the wild-type sequence of the domain. In some cases, the ribonuclease domain derived from a bacterial or archaeal RNase can be truncated by at least 1 amino acid (e.g., at least 2, 3, 4, 5, 6, 7, 8 amino acids or more than 8 amino acids) at the C-terminus relative to the wild-type sequence of the domain. Truncated polymerase and/or ribonuclease domains derived from viral reverse transcriptases may help with the folding of a chimeric RT disclosed herein while minimally affecting the activity and/or function of the protein.

In some embodiments, a non-natural reverse transcriptase may comprise mutations in one or more domains in order to enhance or reduce certain enzymatic activities. In some cases, at least 1 mutation (e.g., at least 2, 3, 4, 5, 6, 7, 8, 9, 10 or greater than 10 mutations) is present in one or more domains of a non-natural (e.g., chimeric) RT, for example in a polymerase domain or ribonuclease domain. Mutations in the one or more domains may be any mutation or variation known in the art including amino acid insertions, deletions, or substitutions, in the respective domains. A desired property of the RT, for example, may be increased efficiency of cDNA generation. Increased efficiency of cDNA generation can be accomplished, in some cases, by a reduction of ribonuclease activity. Increased efficiency of cDNA generation can be accomplished, in some cases, by an increase in DNA polymerase activity. A chimeric RT of the disclosure may have reduced or substantially reduced ribonuclease activity (e.g., RNase H activity) or in some cases, may completely lack ribonuclease activity. The reduction in ribonuclease activity can result from one or more mutations in an active site of the domain. A chimeric RT of the disclosure may have increased DNA polymerase activity. The increase in polymerase activity can result from one or more mutations in an active site of the domain. Active sites generally refer to a region of an enzyme where a substrate molecule binds and undergoes a chemical reaction. Active sites generally contain residues that form non-covalent and/or covalent interactions with substrates which are important for enzymatic activity. Changes at the interface of the active site can, in some cases, reduce or diminish enzymatic activities. Alternatively, mutations made in active sites may enhance or increase enzymatic activities depending on the type of mutation (e.g., conservative or non-conservative mutations). In some cases, at least one mutation is present in an active site. In some cases, mutations made to the domain other than at the active site can also result in changes in enzymatic activity. Such mutations may result in indirect changes to an active site, for example, changes to the conformation of the active such that it has decreased or increased ability to bind to a substrate.

A viral polymerase domain and/or a viral ribonuclease domain of a chimeric construct described herein may have one or more mutations compared to the natural or wild-type sequence of the domain. In some cases, the polymerase domain comprises at least 1 mutation (e.g., at least 2, 3, 4, 5, 6, 7, 8 mutations or more than 8 mutations) relative to the wild-type sequence of the domain. In some cases, the ribonuclease domain comprises at least 1 mutation (e.g., at least 2, 3, 4, 5, 6, 7, 8 mutations or more than 8 mutations) relative to the native sequence. For example, an M-MLV RT may comprise a D524G, E562Q, and/or D583N mutation as described in U.S. Pat. No. 8,753,845, which is herein incorporated in its entirety for all purposes. Such mutations may reduce RNase H activity.

The RTs provided herein may possess at least one non-mutated domain and at least one mutated domain in any combination. In some cases, the mutated domain is an RNase domain having a mutation that reduces or eliminates ribonuclease activity. For example, a non-natural RT provided herein (SEQ ID NO: 9) may comprise a mutated variant of a ribonuclease domain from *T. thermophilus* (e.g., SEQ ID NO: 21) linked to a polymerase domain from M-MLV RT (e.g., SEQ ID NO: 2). In some embodiments, the ribonuclease domain is not mutated (e.g., wild-type sequence). In some embodiments, a non-natural (e.g., chimeric) RT provided herein (SEQ ID NO: 10) comprises a mutated variant of a ribonuclease domain from *T. litoralis* (e.g., RNase H II) (e.g., SEQ ID NO: 22) linked to a polymerase domain from M-MLV RT (e.g., SEQ ID NO: 2). In some embodiments, the ribonuclease domain is not mutated (e.g., wild-type sequence). In some embodiments, a non-natural (e.g., chimeric) RT provided herein comprises a mutated variant of a ribonuclease domain from *Thermococcus gammatolerans* (*T. gammatolerans*) linked to a polymerase domain from M-MLV RT (SEQ ID NO: 10). In some embodiments, the ribonuclease domain is not mutated (e.g., wild-type sequence). In some embodiments, a non-natural (e.g., chimeric) reverse transcriptase (SEQ ID NO: 11) comprises a mutated variant of a ribonuclease domain from *T. thermophilus* (e.g. SEQ ID NO: 21) linked to a polymerase domain from HIV-1 RT (e.g., SEQ ID NO: 5). In some embodiments, the ribonuclease domain is not mutated (e.g., wild-type sequence). In some embodiments, a non-natural (e.g., chimeric) reverse transcriptase (SEQ ID NO: 12) comprises a mutated variant of a ribonuclease domain from *T. litoralis* (e.g., RNase H II) (e.g., SEQ ID NO: 22) linked to a polymerase domain from HIV-1 RT (e.g., SEQ ID NO: 5). In some embodiments, the ribonuclease domain is not mutated (e.g., wild-type sequence), In some embodiments, a non-natural (e.g., chimeric) RT provided herein comprises a mutated variant of a ribonuclease domain from *Thermococcus gammatolerans* (*T. gammatolerans*) linked to a polymerase domain from HIV-1 RT (SEQ ID NO: 11). In some embodiments, the ribonuclease domain is not mutated (e.g., wild-type sequence). In some embodiments, the mutations described herein result in a mutated variant having reduced ribonuclease activity. In some embodiments, the mutations described herein result in a mutated variant having no discernable ribonuclease activity.

In some cases, a chimeric reverse transcriptase may comprise an amino acid sequence of any of SEQ ID NOs: 9-12. In some cases, a chimeric reverse transcriptase may comprise an amino acid sequence at least 75%, at least 80%, at least 85%, at least 90%, at least 91%, at least 92%, at least 93%, at least 94%, at least 95%, at least 96%, at least 97%, at least 98%, or at least 99% identical to of any of SEQ ID NOs: 9-12.

Polymerase Domain

A polymerase domain of an RT provided herein may comprise any polymerase or polymerase activity, e.g., DNA polymerase, RNA polymerase, DNA-dependent DNA polymerase, or RNA-dependent DNA polymerase. In some embodiments, the polymerase domain is a DNA polymerase. In some cases, the polymerase domain has one or more activities, e.g., DNA-dependent DNA polymerase activity and/or RNA-dependent DNA polymerase activity. In some cases, the polymerase domain has RNA-dependent DNA polymerase activity but not DNA-dependent DNA polymerase activity or limited DNA-dependent DNA polymerase activity.

In some cases, a polymerase domain within a non-natural RT provided herein may be at least about 80% identical (e.g., at least about 85%, 90%, 95% identical or 100% identical) to the polymerase domain of a viral reverse transcriptase, such as a Moloney Murine Leukemia Virus Reverse Transcriptase (M-MLV RT), Human Immunodeficiency Virus-1 Reverse Transcriptase (HIV-1 RT), or Avian Myeloblastosis Virus Reverse Transcriptase (AMV RT).

The activity of a polymerase domain within an RT provided herein may be increased, for example, by mutation (or genetic modification). A polymerase domain with increased polymerase activity may have at least about 2.5%, at least about 5%, at least about 7.5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% greater activity than the corresponding unmutated polymerase. In some cases, the polymerase domain may have decreased polymerase activity. Decreased polymerase activity can be acceptable, for example, if there are other improvements in the domain (e.g., improved folding, etc). In some embodiments, a chimeric RT of the disclosure may not contain a modification or mutation in the polymerase domain and may not contain a modification which increases or decreases polymerase activity.

A polymerase domain in a non-natural RT provided herein may comprise one or more truncations. For example, it may be truncated at the N-terminus, e.g., by at least 1 amino acid (e.g., at least 2, 3, 4, 5, 6, 7, 8 amino acids or more than 8 amino acids). In some cases, the polymerase domain within a non-natural RT provided herein may be truncated at the C-terminus (e.g., at least 2, 3, 4, 5, 6, 7, 8 amino acids or more than 8 amino acids).

A polymerase domain within in a non-natural RT provided herein may comprise one or more mutations compared to the wild-type sequence of the domain. In some cases, the polymerase domain comprises at least 1 mutation (e.g., at least 2, 3, 4, 5, 6, 7, 8 mutations or more than 8 mutations). In some cases, the ribonuclease domain may be at least 60% identical (e.g., at least 65%, 70%, 75%, 80%, 85%, 90%, or 95% identical) and less than 100% identical to a wild-type RNase domain.

In some cases, the polymerase domain is derived from one or more of the following proteins: retroviral reverse transcriptase, lentiviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase, Tne DNA polymerase, Tma DNA polymerase, and any mutant, fragment, variant or derivative thereof. Reverse transcriptases having polymerase domains include retroviral RTs such as Moloney Murine Leukemia Virus (M-MLV or M-MuLV) RT, Human Immunodeficiency Virus (e.g., HIV-1 and HIV-2) RT, Simian Immunodeficiency Virus (SIV) RT, Avian Sarcoma-Leukosis Virus (ASLV) RT, and Avian Myeloblastosis Virus (AMV) RT. Examples of ASLV RTs include, but are not limited to, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT. Table 1 provides several examples of retroviral proteins comprising reverse transcriptase domains (e.g., RSV, AMV type 1, AMV type 2, and RAV type 2) (reverse transcriptase domains indicated in bold font).

TABLE 1

| SEQ ID NO: | Description | Amino Acid Sequence |
|---|---|---|
| 23 | RSV, pol | TVALHLAIPLKWKPDHTPVWIDQWPLPEGKLVALT QLVEKELQLGHIVPSLSCWNTPVFVIRKASGSYRL LHDLRAVNAKLVPFGAVQQGAPVLSALPRGWPL MVLDLKDCFFSIPLAEQDREAFAFTLPSVNNQAPA RRFQWKVLPQGMTCSPTICQLVVGQVLEPLRLK HPSLCMLHYMDDLLLAASSHDGLEAAGEEVISTL ERAGFTISPDKVQREPGVQYLGYKLGSTYVAPVGL VAEPRIATLWDVQKLVGSLQWLRPALGIPPRLMGPF YEQLRGSDPNEAREWNLDMKMAWREIVQLSTTAAL ERWDPALPLEGAVARCEQGAIGVLGQGLSTHPRPCL WLFSTQPTKAFTAWLEVLTLLITKLRASAVRTFGKEV DILLLPACFREDLPLPEGILLALKGFAGKIRSSDTPSIF DIARPLHVSLKVRVTDHPVPGPTVFTDASSSTHKGVV VWREGPRWEIKEIADLGASVQQLEARAVAMALLLW PTAPTNVVTDSAFVAKMLLKMGQEGVPSTAAAFILE DALSQRSAMAAVLHVRSHSEVPGFFTEGNDVADSK ATFQAYPLREAKDLHTALHIGPRALSKACNISMQQA REVVQTCPHCNSAPALEAGVNPRGLGPLQIWQTDFT LEPRMAPRSWLAVTVDTASSAIVVTQHGRVTSVAAQ HHWATAIAVLGRPKAIKTDNGSCFTSKSTREWLARW GIAHTTGIPGNSQGQAMVERANRLLKDRIRVLAEGD GFMKRIPTSKQGELLAKAMYALNHFERGENTKTPIQ KHWRPTVLTEGPPVKIRIETGEWEKGWNVLVWGRG YAAVKNRDTDKVIWVPSRKVKPDITQKDEVTKKDE ASPLFAGISDWIPWEDEQEGLQGETASNKQERPGEDT LAANES |

TABLE 1-continued

| SEQ ID NO: | Description | Amino Acid Sequence |
|---|---|---|
| 24 | AMV type 1, partial pol | RATVLTVALHLAIPLKWKPNHTPVWIDQWPLPEGK LVALTQLVEKELQLGHIEPSLSCWNTPVFVIRKAS GSYRLLHDLRAVNAKLVPFGAVQQGAPVLSALPR GWPLMVLDLKDCFFSIPLAEQDREAFAFTLPSVNN QAPARRFQWKVLPQGMTCSPTICQLIVGQILEPLR LKHPSLRMLHYMDDLLLAASSHDGLEAAGEEVIS TLERAGFTISPDKVQREPGVQYLGYKLGSTYVAPV GLVAEPRIATLWDVQKLVGSLQSVRPALGIPPRLMGP FYEQLRGSDPNEAREWNLDMKMAWREIVQLSTTAA LERWDPALPLEGAVARCEQGAIGVLGQGLSTHPRPC LWLFSTQPTKAFTAWLEVLTLLITKLRASAVRTFGKE VDILLLPACFREDLPLPEGILLALRGFAGKIRSSDTPSI FDIARPLHVSLKVRVTDHPVPGPTVFTDASSSTHKGV VVWREGPRWEIKEIADLGASVQQLEARAVAMALLL WPTTPTNVVTDSAFVAKMLLKMGQEGVPSTAAAFIL EDALSQRSAMAAVLHVRSHSEVPGFFTEGNDVADSQ ATFQAYPLREAKDLHTALHIGPRALSKACNISMQQA REVVQTCPHCNSAPALEAGVNPRGLGPLQIWQTDFT LEPRMAPRSWLAVTVDTASSAIVVTQHGRVTSVAAQ HHWATAIAVLGRPKAIKTDNGSCFTSKSTREWLARW GIAHTTGIPGNSQGQAMVERANRLLKDKIRVLAEGD GFMKRIPTSKQGELLAKAMYALNHFERGENTKTPIQ KHWRPTVLTEGPPVKIRIETGEWEKGWNVLVWGRG YAAVKNRDTDKVIWVPSRKVKPDITQKDEVTKKDE ASPLFAGISDWAPWEGEQEGLQEETASNKQERPGED TPAANES |
| 25 | AMV type 2, partial pol | GRATVFTVALHLAIPLKWKPDHTPVWIDQWPLPEG KLVALTQLVEKELQLGHIEPSLSCWNTPVFVIRKA SGSYRLLHDLRAVNAKLVPFGAVQQGAPVLSALP RGWPLMVLDLKDCFFSIPLAEQDREAFAFTLPSVN NQAPARRFQWKVLPQGMTCSPTICQLIVGQILEPL RLKHPSLRMLHYMDDLLLAASSHDGLEAAGEEVI STLERAGFTISPDKVQKEPGVQYLGYKLGSTYVAP VGLVAEPRIATLWDVQKLVGSLQSVRPALGIPPRLM GPFYEQLRGSDPNEAREWNLDMKMAWREIVQLSTT AALERWDPALPLEGAVARCEQGAIGVLGQGLSTHPR PCLWLFSTQPTKAFTAWLEVLTLLITKLRASAVRTFG KEVDILLLPACFREDLPLPEGILLALRGFAGKIRSSDTP SIFDIARPLHVSLKVRVTDHPVPGPTVFTDASSSTHKG VVVWREGPRWEIKEIADLGASVQQLEARAVAMALL LWPTTPTNVVTDSAFVAKMLLKMGQEGVPSTAAAFI LEDALSQRSAMAAVLHVRSHSEVPGFFTEGNDVADS QATFQAYPLREAKDLHTALHIGPRALSKACNISMQQ AREVVQTCPHCNSAPALEAGVNPRGLGPLQIWQTDF TLEPRMAPRSWLAVTVDTASSAIVVTQHGRVTSVAA QHHWATAIAVLGRPKAIKTDNGSCFTSKSTREWLAR WGIAHTTGIPGNSQGQAMVERANRLLKDKIRVLAEG DGFMKRIPTSKQGELLAKAVYALNHFERGENTKTPI QKHWRPTVLTEGPPVKIRIETGEWEKGWNVLVWGR GYAAVKNRDTDKVIWVPSRKVKPDITQKDEVTKRD EASPLFAGISDWAPWEGEQEGLQEETASNKQERPGE DTLAANES |
| 26 | Rous-associated virus type 2, partial RT | TVALHLAIPLKWKPDHTPVWIDQWPLPEGKLVAVT QLVEKELQLGHIEPSLSCWNTPVFVIRKASGSYRL LHDLRAVNAKLVPFGAVQQGAPVLSALPRGWPL MVLDLKDCFFSIPLAEQDREAFAFTLPSVNNQAPA RRFQWKVLPQGMTCSPTICQLVVGQVLEPLRLK HPALRMLHYMDDLLLAASSHDGLEAAGKEVIGTL ERAGFTISPDKIQREPGVQYLGYKLGSTYVAPVGL VAEPRIATLWDVQKLVGSLQWLRPALGIPPRLMGPF YEQLRGSDPNEAREWNLDMKMAWREIVQLSTTAAL ERWDPAQPLEGAVARCEQGAIGVLGQGLSTHPRPCL WLFSTQPTKAFTAWLEVLTLLITKLRASAVRTFGKEV DILLLPACFREDLPLPEGILLALRGFAGKIRSSDTPSIF DIARPLHVSLKVRVTDHPVPGPTVFTDASSSTHKGVV VWREGPRWEIKEIVDLGASVQQLEARAVAMALLLW PTTPTNVVTDSAFVAKMLLKMGQEGVPSTAAAFILE DALSQRSAMAAVLHVRSHSEVPGFFTEGNDVADSQ ATFQAYPLREAKDLHTALHIGPRALSKACNISMQQA REVVQTCPHCNSAPALEAGVNPRGLGPLQIWQTDFT LEPRMAPRSWLAVTVDTASSAIVVTQHGRVTSVAAQ HHWATAIAVLGRPKAIKTDNGSCFTSKSTREWLARW GIAHTTGIPGNSQGQAMVERANRLLKDKIRVLAEGD GFMKRIPASKQGELLAKAMYALNHFERGENTKTPVQ KHWRPTVLTEGPPVKIRIETGEWEKGWNVLVWGRG |

TABLE 1-continued

| SEQ ID NO: | Description | Amino Acid Sequence |
|---|---|---|
| | | YAAVKNRDTDKVIWVPSRKVKPDITQKDEVTKKDE ASPLFAGSSDWIPWGDEQEGLQEEAASNKQEGPGED TLAANES |

In some instances, the polymerase domain of a chimeric RT provided herein comprises a polymerase identical to or derived from M-MLV. M-MLV RT (SEQ ID NO: 1) contains a single subunit of ~75 kDa that comprises a RNA-dependent DNA polymerase domain (SEQ ID NO: 2) (~510 amino acids in length) and a RNase H domain (SEQ ID NO: 3). In some instances, a non-natural RT provided herein comprises a domain derived from a M-MLV polymerase domain (e.g., SEQ ID NO: 2). In some instances, the domain derived from a M-MLV polymerase domain comprises an active site domain comprising 109 (R), 118 (N), 149 (D), 187 (L), 188 (P), 189 (Q), 190 (G), 221 (Y), 223 (D), and 224 (D) of SEQ ID NO: 2. In some instances, a non-natural RT provided herein comprising a domain derived from a M-MLV polymerase domain comprises at least one mutation at an active site residue, for example, at one of residues 109 (R), 118 (N), 149 (D), 187 (L), 188 (P), 189 (Q), 190 (G), 221 (Y), 223 (D), and 224 (D) of SEQ ID NO: 2. In some embodiments, the mutation at the active site residue is a conservative mutation (e.g., a mutation to an amino acid with similar biochemical and/or physicochemical properties (e.g. charge, hydrophobicity, size, positively charged, negatively charged, etc.)). The conservative mutation of the active site residue of the polymerase domain of a chimeric RT can result in a change to an amino acid having the same or similar properties (e.g., hydrophobic, hydrophilic, polar, non-polar, positively charged, negatively charged, etc.) as the original, unmutated residue. In some embodiments, the conservative mutation of the active site residue results in a change (e.g., increase or decrease) in the activity (e.g., enzymatic activity) of the M-MLV polymerase domain. For example, the conservative mutation in the active site can increase the activity of the domain by improving the binding ability and/or affinity of the polymerase domain to a binding partner. In some embodiments, the mutation at the active site residue can be a non-conservative mutation (e.g., a mutation to an amino acid with dissimilar biochemical and/or physicochemical properties (e.g., charge, hydrophobicity, size, etc.)). The non-conservative mutation in the active site residue of a polymerase domain of a chimeric RT can result in a change to an amino acid having different or dissimilar properties as the unmutated residue (e.g., hydrophobic, hydrophilic, polar, non-polar, etc.). In some embodiments, the non-conservative mutation of the active site residue results in a change (e.g., increase or decrease) in the activity (e.g., enzymatic activity) of the M-MLV polymerase domain. For example, the non-conservative mutation in the active site can decrease the activity of the domain by decreasing the ability of the polymerase domain to bind to a binding partner. The effect on enzymatic activity of certain mutations in the active site can, in some cases, be predicted based on computational modeling and/or empirical observations. However, in some cases, the effect of mutations in the active site may not be accurately predicted. Mutations at active sites can be optimized by various experimental methods, including high-throughput screening of variant libraries.

In some embodiments, a non-natural RT provided herein comprises a polymerase domain derived from a M-MLV polymerase domain (e.g., SEQ ID NO: 2), and the polymerase domain comprises at least one conservative mutation at one of residues 109 (R), 118 (N), 149 (D), 187 (L), 188 (P), 189 (Q), 190 (G), 221 (Y), 223 (D), and 224 (D) of SEQ ID NO: 2. In some embodiments, a non-natural RT provided herein comprises a polymerase domain derived from a M-MLV polymerase domain (e.g., SEQ ID NO: 2), and the polymerase domain comprises at least one non-conservative mutation at one of residues 109 (R), 118 (N), 149 (D), 187 (L), 188 (P), 189 (Q), 190 (G), 221 (Y), 223 (D), and 224 (D) of SEQ ID NO: 2. In certain embodiments, at least one mutation at an active site residue (e.g., 109 (R), 118 (N), 149 (D), 187 (L), 188 (P), 189 (Q), 190 (G), 221 (Y), 223 (D), and 224 (D) of SEQ ID NO: 2) results in increased activity of the domain. In certain embodiments, at least one mutation at an active site residue (e.g., 109 (R), 118 (N), 149 (D), 187 (L), 188 (P), 189 (Q), 190 (G), 221 (Y), 223 (D), and 224 (D) of SEQ ID NO: 2) results in decreased activity of the domain. In some embodiments, the mutation in the polymerase domain is at an amino acid residue other than an active site residue. A mutation at an amino acid residue other than an active site residue can, in some cases, affect the active site (e.g., conformation of the active site) and consequently affect the activity of the polymerase domain.

In some instances, the polymerase domain is an HIV polymerase domain. Human Immunodeficiency Virus-1 (e.g., HIV-1) RT exists as a heterodimer of p66 and p51 subunits in which the smaller subunit (p51, ~51 kDa) is derived from the larger subunit (p66, ~66 kDa) by proteolytic cleavage. The larger subunit of the RT heterodimer, p66 (SEQ ID NO: 4), contains the active sites for both of the enzymatic activities of RT (e.g., polymerase and RNase H). A polymerase domain of a non-natural RT provided herein may thus comprise a polymerase domain such as amino acids 1-437 of SEQ ID NO: 4 (SEQ ID NO: 5) or a domain derived from SEQ ID NO: 5. A non-natural RT may also comprise a structure sub-unit, such as a sub-unit derived from p51 of HIV.

Avian Sarcoma-Leukosis Virus (ASLV) RT can also be found as a heterodimer of two subunits, alpha which is ~62 kDa and beta which is ~94 kDa. The alpha subunit is derived from the beta subunit by proteolytic cleavage.

Ribonuclease Domain

A non-natural RT provided herein can comprise an RNase domain that exhibits RNase activity. The RNase can be identical to, or derived from, a naturally-occurring RNase domain. In some embodiments, the RNase domain is structurally similar to a natural RNase. In some cases, the RNase domain does not exhibit RNase activity or exhibits reduced RNase activity. Generally, the RNase activity catalyzes the degradation of RNA into smaller components. The RNase activity can be RNase H activity. The RNase domain may cleave RNA (e.g., mRNA) in a DNA/RNA duplex to produce ssDNA. In some cases, the RNase activity is non-specific. In some cases, the RNase activity is an endonuclease activity; in some cases it may cleave RNA via a hydrolytic mechanism, sometimes with the aid of an enzyme-bound divalent metal ion. Generally, the RNase domain does not hydrolyze the phosphodiester bonds within single-stranded and double-stranded DNA or RNA.

In some instances, an RNase domain within a non-natural RT provided herein may be derived from a virus (e.g., retrovirus, HIV, HIV1, HIV2), a lentivirus, a bacterium (e.g., an extremophilic or thermophilic bacterium), an archaea (e.g., an extremophilic or thermophilic bacterium), microorganism, eukaryote, or multicellular organism (e.g, human). In some cases, the RNase domain is identical to, or derived from RNase H, RNase H1, RNase HII, or RNase HIII.

The three-dimensional structure of RNase within a non-natural RT provided herein may be identical to, or similar to that of a natural RNase. For example, a RNase domain provided herein may comprise a 5-stranded β-sheet surrounded by a distribution of α-helices. In some cases, the RNase H does not comprise one or more helices (e.g, a C-helix).

An RT provided herein may comprise an RNase derived from an organism with high levels of thermal stability. For example, the RNase may be derived from a bacterial or archaeal RNase that can function at temperatures of at least 30° C. (e.g., at least about 32° C., at least about 34° C., at least about 36° C., at least about 38° C., at least about 40° C., at least about 42° C., at least about 45° C., at least about 50° C., at least about 55° C., at least about 60° C., at least about 65° C., at least about 70° C., at least about 75° C., at least about 80° C., at least about 85° C., or at least about 90° C.). In some cases, the RNase may be derived from a bacterial or archaeal RNase that can function at temperatures of at least 40° C. In some examples, the RNase within an RT provided herein may be derived from a extremophilic (e.g. thermophilic) bacterium (e.g., *T. thermophilus*, SEQ ID NO: 7) that can grow optimally at temperatures of about 66° C.-68° C. or an extremophilic (e.g. thermophilic) archaeon (e.g., *T. litoralis*, SEQ ID NO: 8) that can grow optimally at temperatures of about 85° C.-88° C.

In some cases, the RNase domain is derived from an M-MLV RT RNase domain, e.g., (SEQ ID NO: 3). In some cases, the RNase domain is derived from an HIV RT RNase (e.g., SEQ ID NO: 6).

The function or structure of an RNase within an RT provided herein may be reduced or increased, for example by mutation (or genetic modification). A ribonuclease domain with reduced ribonuclease activity may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 7.5%, less than about 5%, or less than about 2.5% of the ribonuclease activity of the corresponding unmutated ribonuclease, such as the ribonuclease domain of a wild-type viral RT (e.g., M-MLV RT, HIV-1 RT, AMV RT, RSV RT), or the ribonuclease activity of an unmutated cellular RNase H (e.g., bacterial or archaeal RNase H, thermophilic RNase H). In some cases, the chimeric RTs of the disclosure may have at least 50% (e.g., at least 55%, at least 60%, at least 65%, at least 70%, at least 75%, at least 80%, at least 85%, at least 90%, or at least 95%) of the RNase H activity compared to the corresponding wild-type RT and/or un-mutated ribonuclease domain. In some cases, the chimeric RTs of the disclosure may have at least 50% and less than 100% of the RNase H activity compared to the corresponding wild-type RT and/or un-mutated ribonuclease domain. In contrast, in some embodiments, a chimeric RT of the disclosure may not contain a modification or mutation in the RNase H domain and may not contain a modification which reduces RNase H activity.

A ribonuclease domain in a non-natural RT provided herein may comprise one or more truncations. For example, it may be truncated at the N-terminus, e.g., by at least 1 amino acid (e.g., at least 2, 3, 4, 5, 6, 7, 8 amino acids or more than 8 amino acids). In some cases, the ribonuclease domain within a non-natural RT provided herein may be truncated at the C-terminus, e.g., by at least 1 amino acid (e.g., at least 2, 3, 4, 5, 6, 7, 8 amino acids or more than 8 amino acids).

A ribonuclease domain within in a non-natural RT provided herein may comprise one or more mutations compared to the wild-type sequence of the domain. In some cases, the ribonuclease domain comprises at least 1 mutation (e.g., at least 2, 3, 4, 5, 6, 7, 8 mutations or more than 8 mutations). In some cases, the ribonuclease domain may be at least 60% identical (e.g., at least 65%, 70%, 75%, 80%, 85%, 90%, or 95% identical) and less than 100% identical to a wild-type RNase domain.

A non-natural RT provided herein can comprise a thermophilic ribonuclease domain. For example, the thermophilic ribonuclease domain may be identical to or derived from *T. thermophilus* (SEQ ID NO: 7) or *T. litoralis* (SEQ ID NO: 8). In specific examples, such ribonuclease domain comprises a truncation or mutation (e.g., SEQ ID NO: 21 and SEQ ID NO: 22).

In some particular examples, the ribonuclease domain derived from a thermophile, e.g., SEQ ID NO: 7 and SEQ ID NO: 8, may have one or more mutations compared to the wild-type sequence of the domain, e.g., SEQ ID NO: 21 and SEQ ID NO: 22. A mutation compared to the wild-type sequence of the domain may be an active site mutation. In some cases, the ribonuclease domain comprises at least 1 mutation (e.g., at least 2, 3, 4, 5, 6, 7, 8 mutations or more than 8 mutations) relative to the wild-type sequence of the domain. In some cases, the ribonuclease domain may be at least 60% identical (e.g., at least 65%, 70%, 75%, 80%, 85%, 90%, or 95% identical) and less than 100% identical to wild-type Tth RNase H (SEQ ID NO: 7) or wild-type Tli RNase H (SEQ ID NO: 8). In some cases, the ribonuclease domain may be at least 50% identical and less than 100% identical to SEQ ID NO: 7 or SEQ ID NO: 8. In some cases, the ribonuclease domain may be at least 50% identical and less than 99.9% identical to SEQ ID NO: 7 or SEQ ID NO: 8; less than 99.8% identical to SEQ ID NO: 7 or SEQ ID NO: 8; less than 99.7% identical to SEQ ID NO: 7 or SEQ ID NO: 8; less than 99.6% identical to SEQ ID NO: 7 or SEQ ID NO: 8; less than 99.5% identical to SEQ ID NO: 7 or SEQ ID NO: 8; less than 99.4% identical to SEQ ID NO: 7 or SEQ ID NO: 8; less than 99.3% identical to SEQ ID NO: 7 or SEQ ID NO: 8; or less than 99% identical to SEQ ID NO: 7 or SEQ ID NO: 8. In some cases, the ribonuclease domain may be at least 75% identical and less than 99.8% identical to wild-type Tth RNase H (SEQ ID NO: 7) or wild-type Tli RNase H (SEQ ID NO: 8).

Mutations such as, for example, substitutions at an active site can be introduced to affect the enzymatic activity of the domain. Homologous proteins that are similar at the sequence level, at the structural level, and/or at the functional level may have similar active sites, for example in terms of 3D structure, amino acid characteristics (e.g., sequence), and other biochemical properties. RNase H's generally have an active site centered on a conserved sequence motif composed of aspartate and glutamate residues, often referred to as the DEDD motif. These residues interact with catalytically required magnesium ions and mutation of these residues and the corresponding homologous residues in related proteins may result in RNases with increased or reduced enzymatic activities. The DEDD motif, can be found in *T. thermophilus* (SEQ ID NO: 7) at, for example, residues 14 (D), 52 (E), 74 (D) and 139 (D). The DEDD motif, can be found in *T. litoralis* (SEQ ID NO: 8) at, for example, residues 7 (D), 8 (E), 105 (D) and 135 (D).

In some embodiments, a non-natural RT provided herein comprises a ribonuclease domain derived from *T. thermophilus* (SEQ ID NO: 7). In some embodiments, a non-natural RT provided herein comprising a domain derived from *T. thermophilus* comprises at least one mutation at an active site residue, for example, at one of residues 14 (D), 52 (E), 74 (D) and 139 (D) of SEQ ID NO: 7. In some embodiments, the mutation at the active site residue is a conservative mutation (e.g., a mutation to an amino acid with similar biochemical and/or physicochemical properties (e.g., charge, hydrophobicity, size, etc.)). The conservative mutation of the active site residue of the ribonuclease domain of a chimeric RT can result in a change to an amino acid having the same or similar properties (e.g., hydrophobic, hydrophilic, polar, non-polar, positively charged, negatively charged etc.) as the original, unmutated residue. In some embodiments, the conservative mutation of the active site residue results in a change (e.g., increase or decrease) in the activity (e.g., enzymatic activity) of the *T. thermophilus* ribonuclease domain. For example, the conservative mutation in the active site can increase the activity of the domain by improving the binding ability and/or affinity of the ribonuclease domain to a binding partner. In some embodiments, the mutation at the active site residue is a non-conservative mutation (e.g., a mutation to an amino acid amino acid having different or dissimilar properties as the unmutated residue (e.g., hydrophobic, hydrophilic, polar, non-polar, positively charged, negatively charged, etc.)). In some embodiments, the non-conservative mutation of the active site residue results in a change (e.g., increase or decrease) in the activity (e.g., enzymatic activity) of the ribonuclease domain. For example, the non-conservative mutation in the active site can decrease the activity of the domain by decreasing the ability of the ribonuclease domain to bind a binding partner. The effect on enzymatic activity of certain mutations in the active site can, in some cases, be predicted based on computational modeling and/or empirical observations. However, in some cases, the effect of mutations in the active site may not be accurately predicted. Mutations at active sites can be optimized by various experimental methods, including high-throughput screening of variant libraries.

In some embodiments, a non-natural RT provided herein comprises a ribonuclease domain derived from a *T. thermophilus* RNase H domain (e.g., SEQ ID NO: 7), and the ribonuclease domain comprises at least one conservative mutation at one of residues 14 (D), 52 (E), 74 (D) and 139 (D) of SEQ ID NO: 7. In some embodiments, a non-natural RT provided herein comprises a ribonuclease domain derived from a *T. thermophilus* RNase H domain (e.g., SEQ ID NO: 7), and the ribonuclease domain comprises at least one non-conservative mutation at one of residues 14 (D), 52 (E), 74 (D) and 139 (D) of SEQ ID NO: 7. In certain embodiments, at least one mutation at an active site residue (e.g., 14 (D), 52 (E), 74 (D) and 139 (D) of SEQ ID NO: 7) results in increased ribonuclease activity of the domain. In certain embodiments, at least one mutation at an active site residue (e.g., 14 (D), 52 (E), 74 (D) and 139 (D) of SEQ ID NO: 7) results in decreased ribonuclease activity of the domain. In some embodiments, the mutation in the ribonuclease domain is at an amino acid residue other than an active site residue. A mutation at an amino acid residue other than an active site residue can, in some cases, affect the active site (e.g., conformation of the active site) and consequently affect the activity of the ribonuclease domain. In some embodiments, an amino acid mutation from the amino acid Asp (D) to the amino acid Asn (N) at residue 14 of SEQ ID NO: 7 (SEQ ID NO: 21), which may be an active site residue, decreases and/or eliminates the enzymatic activity of this domain. Such modification may minimize degradation of RNA, for example during first strand synthesis, thereby possibly increasing cDNA yield.

In some embodiments, a non-natural RT provided herein comprises a ribonuclease domain derived from *T. litoralis* (SEQ ID NO: 8). In some embodiments, a non-natural RT provided herein comprising a domain derived from *T. litoralis* comprises at least one mutation at an active site residue, for example at one of residues 7 (D), 8 (E), 105 (D) and 135 (D) of SEQ ID NO: 8. In some embodiments, the mutation at the active site residue is a conservative mutation (e.g., a mutation to an amino acid with similar biochemical and/or physicochemical properties (e.g., charge, hydrophobicity, size, etc.)). The conservative mutation in the active site residue of the ribonuclease domain of a chimeric RT can result in a change to an amino acid having the same or similar properties (e.g., hydrophobic, hydrophilic, polar, non-polar, positively charged, negatively charged, etc.) as the original, unmutated residue. In some embodiments, the conservative mutation of the active site residues results in a change (e.g., increase or decrease) in the activity (e.g., enzymatic activity) of the *T. litoralis* ribonuclease domain. For example, the conservative mutation in the active site can increase the activity of the domain by improving the binding ability and/or affinity of the ribonuclease domain to a binding partner. In some embodiments, the mutation at the active site residue can be a non-conservative mutation (e.g., a mutation to an amino acid with dissimilar biochemical and/or physicochemical properties (e.g., charge, hydrophobicity, size, etc.)). The non-conservation mutation of the active site residue of a ribonuclease domain of a chimeric RT can result in a change to an amino acid having different or dissimilar properties as the unmutated residue (e.g., hydrophobic, hydrophilic, polar, non-polar, positively charged, negatively charged, etc.). In some embodiments, the non-conservative mutation of the active site residue results in a change (e.g., increase or decrease) in the activity (e.g., enzymatic activity) of the ribonuclease domain. For example, the non-conservative mutation in the active site can decrease the activity of the domain by decreasing the ability of the ribonuclease domain to bind a binding partner. The effect on enzymatic activity of certain mutations in the active site can, in some cases, be predicted based on computational modeling and/or empirical observations. However, in some cases, the effect of mutations in the active site may not be accurately predicted. Mutations at active sites can be optimized by various experimental methods, including high-throughput screening of variant libraries.

In some embodiments, a non-natural RT provided herein comprises a ribonuclease domain derived from a *T. litoralis* RNase H domain (e.g., SEQ ID NO: 8), and the ribonuclease domain comprises at least one conservative mutation at one of residues 7 (D), 8 (E), 105 (D) and 135 (D) of SEQ ID NO: 8. In some embodiments, a non-natural RT provided herein comprises a ribonuclease domain derived from a *T. litoralis* RNase H domain (e.g., SEQ ID NO: 8), and the ribonuclease domain comprises at least one non-conservative mutation at one of residues 7 (D), 8 (E), 105 (D) and 135 (D) of SEQ ID NO: 8. In certain embodiments, at least one mutation at an active site residue (e.g., 7 (D), 8 (E), 105 (D) and 135 (D) of SEQ ID NO: 8) results in increased ribonuclease activity of the domain. In certain embodiments, at least one mutation at an active site residue (e.g., 7 (D), 8 (E), 105 (D) and 135 (D) of SEQ ID NO: 8) results in decreased ribonuclease activity of the domain. In some embodiments, the mutation in the ribonuclease domain is at an amino acid residue other than an active site residue. A mutation at an amino acid residue other than an active site residue can, for example, affect the active site (e.g., conformation of the active site) and consequently affect the activity of the ribonuclease domain. In some embodiments, the domain comprises two amino acid mutations—from Asp (D) to Asn (N) at residue 7 and Glu (E) to Gln (Q) at residue 8 of SEQ ID NO: 8 (SEQ ID NO: 22). Two or more mutations can result in decreased enzymatic activity (e.g., ribonuclease activity) of the ribonuclease domain. Such modification may minimize RNA degradation.

TABLE 2

Amino acid sequences

| SEQ ID NO: | Description | Amino Acid Sequence |
|---|---|---|
| 1 | wt M-MLV RT (pol domain and RNase H domain) | LNIEDEHRLHETSKEPDVSLGSTWLSDFPQAWAETGG MGLAVRQAPLIIPLKATSTPVSIKQYPMSQEARLGIKP HIQRLLDQGILVPCQSPWNTPLLPVKKPGTNDYRPVQ DLREVNKRVEDIHPTVPNPYNLLSGLPPSHQWYTVLD LKDAFFCLRLHPTSQPLFAFEWRDPEMGISGQLTWTR LPQGFKNSPTLFDEALHRDLADFRIQHPDLILLQYVD DLLLAATSELDCQQGTRALLQTLGNLGYRASAKKAQ ICQKQVKYLGYLLKEGQRWLTEARKETVMGQPTPKT PRQLREFLGTAGFCRLWIPGFAEMAAPLYPLTKTGTL FNWGPDQQKAYQEIKQALLTAPALGLPDLTKPFELFV DEKQGYAKGVLTQKLGPWRRPVAYLSKKLDPVAAG WPPCLRMVAAIAVLTKDAGKLTMGQPLVILAPHAVE ALVKQPPDRWLSNARMTHYQALLLDTDRVQFGPVV ALNPATLLPLPEEGLQHNCLDILAEAHGTRPDLTDQP LPDADHTWYTDGSSLLQEGQRKAGAAVTTETEVI WAKALPAGTSAQRAELIALTQALKMAEGKKLNV YTDSRYAFATAHIHGEIYRRRGLLTSEGKEIKNKD EILALLKALFLPKRLSIIHCPGHQKGHSAEARGNR MADQAARKAAITETPDTSTLLI |
| 2 | wt M-MLV pol domain | LNIEDEHRLHETSKEPDVSLGSTWLSDFPQAWAETGG MGLAVRQAPLIIPLKATSTPVSIKQYPMSQEARLGIKPH IQRLLDQGILVPCQSPWNTPLLPVKKPGTNDYRPVQDL REVNKRVEDIHPTVPNPYNLLSGLPPSHQWYTVLDLK DAFFCLRLHPTSQPLFAFEWRDPEMGISGQLTWTRLPQ GFKNSPTLFDEALHRDLADFRIQHPDLILLQYVDDLLL AATSELDCQQGTRALLQTLGNLGYRASAKKAQICQKQ VKYLGYLLKEGQRWLTEARKETVMGQPTPKTPRQLR EFLGTAGFCRLWIPGFAEMAAPLYPLTKTGTLFNWGP DQQKAYQEIKQALLTAPALGLPDLTKPFELFVDEKQG YAKGVLTQKLGPWRRPVAYLSKKLDPVAAGWPPCLR MVAAIAVLTKDAGKLTMGQPLVILAPHAVEALVKQPP DRWLSNARMTHYQALLLDTDRVQFGPVVALNPATLL PLPEEGLQHNCLDILAEAHGTRPDLTD |
| 3 | wt M-MLV RNase H domain | QPLPDADHTWYTDGSSLLQEGQRKAGAAVTTETEVIW AKALPAGTSAQRAELIALTQALKMAEGKKLNVYTDSR YAFATAHIHGEIYRRRGLLTSEGKEIKNKDEILALLKAL FLPKRLSIIHCPGHQKGHSAEARGNRMADQAARKAAIT ETPDTSTLLI |
| 4 | wt HIV-1 RT (pol domain and RNase H domain) | NFPISPIETVPVKLKPGMDGPKVKQWPLTEEKIKALVEI CTEMEKEGKISKIGPENPYNTPVFAIKKKDSTKWRKLV DFRELNKRTQDFWEVQLGIPHPAGLKKKKSVTVLDVG DAYFSVPLDEDFRKYTAFTIPSINNETPGIRYQYNVLPQ GWKGSPAIFQSSMTKILEPFRKQNPDIVIYQYMDDLYV GSDLEIGQHRTKIEELRQHLLRWGLTTPDKKHQKEPPF LWMGYELHPDKWTVQPIVLPEKDSWTVNDIQKLVGK LNWASQIYPGIKVRQLCKLLRGTKALTEVIPLTEEAELE LAENREILKEPVHGVYYDPSKDLIAEIQKQGQGQWTY QIYQEPFKNLKTGKYARMRGAHTNDVKQLTEAVQKIT TESIVIWGKTPKFKLPIQKETWETWWTEYWQATWIPE WEFVNTPPLVKLWYQLEKEPIVGAETFYVDGAANRE TKLGKAGYVTNRGRQKVVTLTDTTNQKTELQAIYL ALQDSGLEVNIVTDSQYALGIIQAQPDQSESELVNQI IEQLIKKEKVYLAWVPAHKGIGGNEQVDKLVSAGI RKVL |

TABLE 2-continued

Amino acid sequences

| SEQ ID NO: | Description | Amino Acid Sequence |
|---|---|---|
| 5 | wt HIV-1 pol domain | NFPISPIETVPVKLKPGMDGPKVKQWPLTEEKIKALVEI CTEMEKEGKISKIGPENPYNTPVFAIKKKDSTKWRKLV DFRELNKRTQDFWEVQLGIPHPAGLKKKKSVTVLDVG DAYFSVPLDEDFRKYTAFTIPSINNETPGIRYQYNVLPQ GWKGSPAIFQSSMTKILEPFRKQNPDIVIYQYMDDLYV GSDLEIGQHRTKIEELRQHLLRWGLTTPDKKHQKEPPF LWMGYELHPDKWTVQPIVLPEKDSWTVNDIQKLVGK LNWASQIYPGIKVRQLCKLLRGTKALTEVIPLTEEAELE LAENREILKEPVHGVYYDPSKDLIAEIQKQGQGQWTY QIYQEPFKNLKTGKYARMRGAHTNDVKQLTEAVQKIT TESIVIWGKTPKFKLPIQKETWETWWTEYWQATWIPE WEFVNTPPLVKLWYQLEKEPIV |
| 6 | wt HIV-1 RNase H domain | GAETFYVDGAANRETKLGKAGYVTNRGRQKVVTLTD TTNQKTELQAIYLALQDSGLEVNIVTDSQYALGIIQAQP DQSESELVNQIIEQLIKKEKVYLAWVPAHKGIGGNEQV DKLVSAGIRKVL |
| 7 | wt Tth RNase H | MNPSPRKRVALFTDGACLGNPGPGGWAALLRFHAHE KLLSGGEACTTNNRMELKAAIEGLKALKEPCEVDLYT DSHYLKKAFTEGWLEGWRKRGWRTAEGKPVKNRDL WEALLLAMAPHRVRFHFVKGHTGHPENERVDREARR QAQSQAKTPCPPRAPTLFHEEA |
| 8 | Wt Tli RNase H II | MNLGGIDEAGRGPVIGPLVIAAVVVDESRMQELEALG VKDSKKLTPKRREELFEEIVQIVDDHVIIQLSPEEIDGRD GTMNELEIENFAKALNSLKVKPDVLYIDAADVKEKRF GDIIGERLSFSPKIIAEHKADSKYIPVAAASILAKVTRDR AIEKLKELYGEIGSGYPSDPNTRRFLEEYYKAHGEFPPI VRKSWKTLRKIEEKLKAKKTQPTILDFLKKP |
| 21 | Tth RNase H- | MNPSPRKRVALFTNGACLGNPGPGGWAALLRFHAHE KLLSGGEACTTNNRMELKAAIEGLKALKEPCEVDLYT DSHYLKKAFTEGWLEGWRKRGWRTAEGKPVKNRDL WEALLLAMAPHRVRFHFVKGHTGHPENERVDREARR QAQSQAKTPCPPRAPTLFHEEA |
| 22 | Tli RNase H II- | MNLGGINQAGRGPVIGPLVIAAVVVDESRMQELEALG VKDSKKLTPKRREELFEEIVQIVDDHVIIQLSPEEIDGRD GTMNELEIENFAKALNSLKVKPDVLYIDAADVKEKRF GDIIGERLSFSPKIIAEHKADSKYIPVAAASILAKVTRDR AIEKLKELYGEIGSGYPSDPNTRRFLEEYYKAHGEFPPI VRKSWKTLRKIEEKLKAKKTQPTILDFLKKP |
| 9 | wt M-MLV pol domain - Tth RNase H- (D10N in active site) | LNIEDEHRLHETSKEPDVSLGSTWLSDFPQAWAETGG MGLAVRQAPLIIPLKATSTPVSIKQYPMSQEARLGIKPH IQRLLDQGILVPCQSPWNTPLLPVKKPGTNDYRPVQDL REVNKRVEDIHPTVPNPYNLLSGLPPSHQWYTVLDLK DAFFCLRLHPTSQPLFAFEWRDPEMGISGQLTWTRLPQ GFKNSPTLFDEALHRDLADFRIQHPDLILLQYVDDLLL AATSELDCQQGTRALLQTLGNLGYRASAKKAQICQKQ VKYLGYLLKEGQRWLTEARKETVMGQPTPKTPRQLR EFLGTAGFCRLWIPGFAEMAAPLYPLTKTGTLFNWGP DQQKAYQEIKQALLTAPALGLPDLTKPFELFVDEKQG YAKGVLTQKLGPWRRPVAYLSKKLDPVAAGWPPCLR MVAAIAVLTKDAGKLTMGQPLVILAPHAVEALVKQPP DRWLSNARMTHYQALLLDTDRVQFGPVVALNPATLL PLPEEGLQHNCLDILAEAHGTRPDLTQPLPDNPSPRK RVALFTNGACLGNPGPGGWAALLRFHAHEKLLSG GEACTTNNRMELKAAIEGLKALKEPCEVDLYTDSH YLKKAFTEGWLEGWRKRGWRTAEGKPVKNRDLW EALLLAMAPHRVRFHFVKGHTGHPENERVDREAR RQAQSQAKTPCPPRAPTLFHEEA |
| 10 | wt M-MLV pol domain - Tli Rnase H II- | LNIEDEHRLHETSKEPDVSLGSTWLSDFPQAWAETGG MGLAVRQAPLIIPLKATSTPVSIKQYPMSQEARLGIKPH IQRLLDQGILVPCQSPWNTPLLPVKKPGTNDYRPVQDL REVNKRVEDIHPTVPNPYNLLSGLPPSHQWYTVLDLK DAFFCLRLHPTSQPLFAFEWRDPEMGISGQLTWTRLPQ GFKNSPTLFDEALHRDLADFRIQHPDLILLQYVDDLLL AATSELDCQQGTRALLQTLGNLGYRASAKKAQICQKQ VKYLGYLLKEGQRWLTEARKETVMGQPTPKTPRQLR EFLGTAGFCRLWIPGFAEMAAPLYPLTKTGTLFNWGP DQQKAYQEIKQALLTAPALGLPDLTKPFELFVDEKQG |

TABLE 2-continued

Amino acid sequences

| SEQ ID NO: | Description | Amino Acid Sequence |
|---|---|---|
| | | YAKGVLTQKLGPWRRPVAYLSKKLDPVAAGWPPCLR<br>MVAAIAVLTKDAGKLTMGQPLVILAPHAVEALVKQPP<br>DRWLSNARMTHYQALLLDTDRVQFGPVVALNPATLL<br>PLPEEGLQHNCLDILAEAHGTRPDLTDQPLPDKLGGIN<br>QAGRGPVIGPLVIAAVVVDESRMQELEALGVKDSK<br>KLTPKRREELFEEIVQIVDDHVIIQLSPEEIDGRDGT<br>MNELEIENFAKALNSLKVKPDVLYIDAADVKEKRF<br>GDIIGERLSFSPKIIAEHKADSKYIPVAAASILAKVTR<br>DRAIEKLKELYGEIGSGYPSDPNTRRFLEEYYKAHG<br>EFPPIVRKSWKTLRKIEEKLKAKKTQPTILDFLKKP |
| 11 | wt HIV-1 pol domain -<br>Tth Rnase H⁻ | NFPISPIETVPVKLKPGMDGPKVKQWPLTEEKIKALVEI<br>CTEMEKEGKISKIGPENPYNTPVFAIKKKDSTKWRKLV<br>DFRELNKRTQDFWEVQLGIPHPAGLKKKKSVTVLDVG<br>DAYFSVPLDEDFRKYTAFTIPSINNETPGIRYQYNVLPQ<br>GWKGSPAIFQSSMTKILEPFRKQNPDIVIYQYMDDLYV<br>GSDLEIGQHRTKIEELRQHLLRWGLTTPDKKHQKEPPF<br>LWMGYELHPDKWTVQPIVLPEKDSWTVNDIQKLVGK<br>LNWASQIYPGIKVRQLCKLLRGTKALTEVIPLTEEAELE<br>LAENREILKEPVHGVYYDPSKDLIAEIQKQGQGQWTY<br>QIYQEPFKNLKTGKYARMRGAHTNDVKQLTEAVQKIT<br>TESIVIWGKTPKFKLPIQKETWETWWTEYWQATWIPE<br>WEFVNTPPLVKLWYQLEKEPIVNPSPRKRVALFTNGA<br>CLGNPGPGGWAALLRFHAHEKLLSGGEACTTNNR<br>MELKAAIEGLKALKEPCEVDLYTDSHYLKKAFTEG<br>WLEGWRKRGWRTAEGKPVKNRDLWEALLLAMAP<br>HRVRFHFVKGHTGHPENERVDREARRQAQSQAKT<br>PCPPRAPTLFHEEA |
| 12 | wt HIV-1 pol domain -<br>Tli Rnase H II⁻ | NFPISPIETVPVKLKPGMDGPKVKQWPLTEEKIKALVEI<br>CTEMEKEGKISKIGPENPYNTPVFAIKKKDSTKWRKLV<br>DFRELNKRTQDFWEVQLGIPHPAGLKKKKSVTVLDVG<br>DAYFSVPLDEDFRKYTAFTIPSINNETPGIRYQYNVLPQ<br>GWKGSPAIFQSSMTKILEPFRKQNPDIVIYQYMDDLYV<br>GSDLEIGQHRTKIEELRQHLLRWGLTTPDKKHQKEPPF<br>LWMGYELHPDKWTVQPIVLPEKDSWTVNDIQKLVGK<br>LNWASQIYPGIKVRQLCKLLRGTKALTEVIPLTEEAELE<br>LAENREILKEPVHGVYYDPSKDLIAEIQKQGQGQWTY<br>QIYQEPFKNLKTGKYARMRGAHTNDVKQLTEAVQKIT<br>TESIVIWGKTPKFKLPIQKETWETWWTEYWQATWIPE<br>WEFVNTPPLVKLWYQLEKEPIVKLGGINQAGRGPVIG<br>PLVIAAVVVDESRMQELEALGVKDSKKLTPKRREE<br>LFEEIVQIVDDHVIIQLSPEEIDGRDGTMNELEIENFA<br>KALNSLKVKPDVLYIDAADVKEKRFGDIIGERLSFSP<br>KIIAEHKADSKYIPVAAASILAKVTRDRAIEKLKELY<br>GEIGSGYPSDPNTRRFLEEYYKAHGEFPPIVRKSWK<br>TLRKIEEKLKAKKTQPTILDFLKKP |

Linkers

The domains of a chimeric protein, for example the polymerase domain and the ribonuclease domain of a chimeric reverse transcriptase, can be joined by a linker. The domains may be covalently linked or non-covalently linked. As used herein, the term "linker" refers to a molecule that joins at least two other molecules, either covalently or non-covalently, e.g., through hydrogen bonds, ionic or van der Waals interactions, e.g., a nucleic acid molecule that hybridizes to one complementary sequence at the 5' end and to another complementary sequence at the 3' end, thus joining two non-complementary sequences. A linker can connect a first polypeptide with at least a second polypeptide. The linker may be a peptide linker or a chemical linker.

Linkers may be of 3 general categories—flexible linkers, rigid linkers, and in vivo cleavable linkers. In addition to linking functional domains together (e.g., flexible and rigid linkers) or releasing free functional domains in vivo (e.g., cleavable linkers), linkers may offer other advantages (e.g., improving biological activity, increasing expression yield, and achieving desirable pharmacokinetic profiles). "Peptide linkers" generally refer to an amino acid sequence or peptide that connects a first polypeptide with a second polypeptide. A peptide linker may be a synthetic sequence (e.g., not naturally occurring in the native polypeptide or protein) or may be a linker sequence native to the protein. The peptide linker can be connected to the first polypeptide and to the second polypeptide by peptide bonds. A peptide linker can be of any suitable length. For example, a peptide linker may be between about 1 and 100 amino acids in length (e.g. between about 10 and 90, about 20 and 80, about 30 and 70, or about 40 and 60 amino acids in length). A peptide linker can be at least 100 amino acids in length (e.g., at least 125, 150, 175, 200, 300, 400, 500 amino acids or longer).

A flexible linker, e.g., a flexible peptide linker, may be used to join domains requiring a certain degree of movement or interaction. For example, a peptide linker may comprise predominantly glycine (G) and serine (S) amino acids, e.g., (GGS)$_n$ or (GSG)$_n$ where n represents any suitable number of repeats. Glycine and serine are relatively small, non-polar amino acids that have shown little interaction with linked proteins and can lack secondary structure, thereby having minimal or no effect on the structure and the function of the linked proteins. In some cases, rigid linkers may be preferred to provide desired orientations and separation of the linked domains, maintaining the independent functions of each peptide. Rigid linkers may form secondary structure, e.g., alpha helices. For example, a linker comprising primarily proline residues or the sequence (EAAAK), where n represents any suitable number of repeats, may be used to provide a more rigid linker compared to glycine and serine based linkers. In some cases, a cleavable linker may be preferred to release the functional domains in vivo. The in vivo cleavage of the linkers in fusion polypeptides may be carried out by proteases that are expressed in vivo under pathological conditions (e.g., cancer or inflammation), in specific cells or tissues, or constrained within certain cellular compartments.

Properties of Non-Natural RTs

A non-natural RT provided herein may be thermally stable at elevated temperatures (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 95° C., or higher). In some cases, a non-natural RT provided herein may be thermally stable at, for example, a temperature between 25° C. and 75° C., between 45° C. and 70° C., between 55° C. and 75° C., between 60° C. and 65° C., or between 60° C. and 70° C. In some cases, the non-natural RTs may retain a certain amount of RNA-dependent DNA polymerase specific activity at elevated temperatures or after incubation at an elevated temperature for at least about 1 minute, at least about 2 minutes, at least about 3 minutes, at least about 4 minutes, at least about 5 minutes, at least about 10 minutes, at least about 15 minutes, at least about 20 minutes, at least about 25 minutes, at least about 30 minutes, at least about 45 minutes, at least about an hour, at least about a day, at least about 2 days, at least about 3 days, at least about 4 days, at least about 5 days, at least about 6 days, at least about 1 week, at least about 2 weeks, at least about 3 weeks, at least about 1 month, at least about 2 months, at least about 3, at least about 4 months, at least about 5 months, at least about 6 months or longer. In some cases, such time period is between 30 minutes and 6 months, 30 minutes and 6 days, 30 minutes and 60 minutes, or other timeframe.

In some cases, a non-natural RT provided herein may retain at least about 5%, 10%, 15%, 20%, 25%, 30%, 35%, 40%, 45%, 50%, 55%, 60%, 65%, 70%, 75%, 80%, 85%, 90%, 95% or greater than 95% specific activity after incubation at an elevated temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.). In some cases, a non-natural RT provided herein may retain at least 50%-100% after incubation at an elevated temperature, e.g., a temperature between 25° C. and 90° C. or between 35° C. and 80° C. or other elevated temperature. In some cases, a non-natural RT provided herein may retain at least about 5%, 10%, 15%, 20%, 25%, 30%, 35%, 40%, 45%, 50%, 55%, 60%, 65%, 70%, 75%, 80%, 85%, 90%, 95% or greater than 95% specific activity after incubation at an elevated temperature for at least about 1 minute, at least about 2 minutes, at least about 3 minutes, at least about 4 minutes, at least about 5 minutes, at least about 10 minutes, at least about 15 minutes, at least about 20 minutes, at least about 25 minutes, at least about 30 minutes, at least about 45 minutes, at least about an hour, at least about a day, at least about 2 days, at least about 3 days, at least about 4 days, at least about 5 days, at least about 6 days, at least about 1 week, at least about 2 weeks, at least about 3 weeks, at least about 1 month, at least about 2 months, at least about 3, at least about 4 months, at least about 5 months, at least about 6 months, or longer. In some cases, the percentage of specific activity retained (e.g., 50%, 75%, etc.) is retained between about 10 minutes and about 30 minutes, between 10 minutes and 60 minutes, between 10 minutes and 6 hours, between 10 minutes and 6 months, or other timeframe. In some cases, a non-natural RT provided herein retains at least 25% specific activity after incubation at a temperature of at least about 50° C. for at least 15 minutes. In some cases, a non-natural RT provided herein retains at least 25% specific activity after incubation at a temperature of at least about 50° C. for at least 30 minutes. In some cases, a non-natural RT provided herein retains at least 25% specific activity after incubation at a temperature of at least about 50° C. for at least 45 minutes. In some cases, a non-natural RT provided herein retains at least 25% specific activity after incubation at a temperature of at least about 50° C. for at least 1 hour. In some cases, a non-natural RT provided herein retains at least 25% specific activity after incubation at a temperature of at least about 50° C. for at least 2 hours. In some cases, a non-natural RT provided herein retains at least 25% specific activity after incubation at a temperature of at least about 50° C. for at least 3 hours. In some cases, a non-natural RT provided herein retains at least 25% specific activity after incubation at a temperature of at least about 50° C. for at least 6 hours. In some cases, a non-natural RT provided herein retains at least 50% specific activity after incubation at a temperature of at least about 50° C. for at least 15 minutes. In some cases, a non-natural RT provided herein retains at least 50% specific activity after incubation at a temperature of at least about 50° C. for at least 30 minutes. In some cases, a non-natural RT provided herein retains at least 50% specific activity after incubation at a temperature of at least about 50° C. for at least 45 minutes. In some cases, a non-natural RT provided herein retains at least 50% specific activity after incubation at a temperature of at least about 50° C. for at least 1 hour. In some cases, a non-natural RT provided herein retains at least 50% specific activity after incubation at a temperature of at least about 50° C. for at least 2 hours. In some cases, a non-natural RT provided herein retains at least 50% specific activity after incubation at a temperature of at least about 50° C. for at least 3 hours. In some cases, a non-natural RT provided herein retains at least 50% specific activity after incubation at a temperature of at least about 50° C. for at least 6 hours. In some cases, a non-natural RT provided herein retains at least 75% specific activity after incubation at a temperature of at least about 50° C. for at least 15 minutes. In some cases, a non-natural RT provided herein retains at least 75% specific activity after incubation at a temperature of at least about 50° C. for at least 30 minutes. In some cases, a non-natural RT provided herein retains at least 75% specific activity after incubation at a temperature of at least about 50° C. for at least 45 minutes. In some cases, a non-natural RT provided herein retains at least 75% specific activity after incubation at a temperature of at least about 50° C. for at least 1 hour. In some cases, a non-natural RT provided herein retains at least 75% specific activity after incubation at a temperature of at least about 50° C. for at least 2 hours. In some cases, a non-natural RT provided herein retains at least 75% specific activity after incubation at a temperature of at least about 50° C. for at least 3 hours. In some cases, a non-natural RT provided herein retains at least 75% specific activity after incubation at a temperature of at least about 50° C. for at least 6 hours. In some cases, a non-natural RT provided herein retains at least 25% specific activity after incubation at a temperature of at least about 55° C. for at least 15 minutes. In some cases, a non-natural RT provided herein retains at least 25% specific activity after incubation at a temperature of at least about 55° C. for at least 30 minutes. In some cases, a non-natural RT provided herein retains at least 25% specific activity after incubation at a temperature of at least about 55° C. for at least 45 minutes. In some cases, a non-natural RT provided herein retains at least 25% specific activity after incubation at a temperature of at least about 55° C. for at least 1 hour. In some cases, a non-natural RT provided herein retains at least 25% specific activity after incubation at a temperature of at least about 55° C. for at least 2 hours. In some cases, a non-natural RT provided herein retains at least 25% specific activity after incubation at a temperature of at least about 55° C. for at least 3 hours. In some cases, a non-natural RT provided herein retains at least 25% specific activity after incubation at a temperature of at least about 55° C. for at least 6 hours. In some cases, a non-natural RT provided herein retains at least 50% specific activity after incubation at a temperature of at least about 55° C. for at least 15 minutes. In some cases, a non-natural RT provided herein retains at least 50% specific activity after incubation at a temperature of at least about 55° C. for at least 30 minutes. In some cases, a non-natural RT provided herein retains at least 50% specific activity after incubation at a temperature of at least about 55° C. for at least 45 minutes. In some cases, a non-natural RT provided herein retains at least 50% specific activity after incubation at a temperature of at least about 55° C. for at least 1 hour. In some cases, a non-natural RT provided herein retains at least 50% specific activity after incubation at a temperature of at least about 55° C. for at least 2 hours. In some cases, a non-natural RT provided herein retains at least 50% specific activity after incubation at a temperature of at least about 55° C. for at least 3 hours. In some cases, a non-natural RT provided herein retains at least 50% specific activity after incubation at a temperature of at least about 55° C. for at least 6 hours. In some cases, a non-natural RT provided herein retains at least 75% specific activity after incubation at a temperature of at least about 55° C. for at least 15 minutes. In some cases, a non-natural RT provided herein retains at least 75% specific activity after incubation at a temperature of at least about 55° C. for at least 30 minutes. In some cases, a non-natural RT provided herein retains at least 75% specific activity after incubation at a temperature of at least about 55° C. for at least 45 minutes. In some cases, a non-natural RT provided herein retains at least 75% specific activity after incubation at a temperature of at least about 55° C. for at least 1 hour. In some cases, a non-natural RT provided herein retains at least 75% specific activity after incubation at a temperature of at least about 55° C. for at least 2 hours. In some cases, a non-natural RT provided herein retains at least 75% specific activity after incubation at a temperature of at least about 55° C. for at least 3 hours. In some cases, a non-natural RT provided herein retains at least 75% specific activity after incubation at a temperature of at least about 55° C. for at least 6 hours. In some cases, a non-natural RT provided herein retains at least 25% specific activity after incubation at a temperature of at least about 60° C. for at least 15 minutes. In some cases, a non-natural RT provided herein retains at least 25% specific activity after incubation at a temperature of at least about 60° C. for at least 30 minutes. In some cases, a non-natural RT provided herein retains at least 25% specific activity after incubation at a temperature of at least about 60° C. for at least 45 minutes. In some cases, a non-natural RT provided herein retains at least 25% specific activity after incubation at a temperature of at least about 60° C. for at least 1 hour. In some cases, a non-natural RT provided herein retains at least 25% specific activity after incubation at a temperature of at least about 60° C. for at least 2 hours. In some cases, a non-natural RT provided herein retains at least 25% specific activity after incubation at a temperature of at least about 60° C. for at least 3 hours. In some cases, a non-natural RT provided herein retains at least 25% specific activity after incubation at a temperature of at least about 60° C. for at least 6 hours. In some cases, a non-natural RT provided herein retains at least 50% specific activity after incubation at a temperature of at least about 60° C. for at least 15 minutes. In some cases, a non-natural RT provided herein retains at least 50% specific activity after incubation at a temperature of at least about 60° C. for at least 30 minutes. In some cases, a non-natural RT provided herein retains at least 50% specific activity after incubation at a temperature of at least about 60° C. for at least 45 minutes. In some cases, a non-natural RT provided herein retains at least 50% specific activity after incubation at a temperature of at least about 60° C. for at least 1 hour. In some cases, a non-natural RT provided herein retains at least 50% specific activity after incubation at a temperature of at least about 60° C. for at least 2 hours. In some cases, a non-natural RT provided herein retains at least 50% specific activity after incubation at a temperature of at least about 60° C. for at least 3 hours. In some cases, a non-natural RT provided herein retains at least 50% specific activity after incubation at a temperature of at least about 60° C. for at least 6 hours. In some cases, a non-natural RT provided herein retains at least 75% specific activity after incubation at a temperature of at least about 60° C. for at least 15 minutes. In some cases, a non-natural RT provided herein retains at least 75% specific activity after incubation at a temperature of at least about 60° C. for at least 30 minutes. In some cases, a non-natural RT provided herein retains at least 75% specific activity after incubation at a temperature of at least about 60° C. for at least 45 minutes. In some cases, a non-natural RT provided herein retains at least 75% specific activity after incubation at a temperature of at least about 60° C. for at least 1 hour. In some cases, a non-natural RT provided herein retains at least 75% specific activity after incubation at a temperature of at least about 60° C. for at least 2 hours. In some cases, a non-natural RT provided herein retains at least 75% specific activity after incubation at a temperature of at least about 60° C. for at least 3 hours. In some cases, a non-natural RT provided herein retains at least 75% specific activity after incubation at a temperature of at least about 60° C. for at least 6 hours.

In some cases, a non-natural RT provided herein may retain at least about 5%, 10%, 15%, 20%, 25%, 30%, 35%, 40%, 45%, 50%, 55%, 60%, 65%, 70%, 75%, 80%, 85%, 90%, 95% or greater than 95% specific activity when conducting a reverse transcription reaction at an elevated temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.). In some cases, a non-natural RT provided herein may retain at least about 5%, 10%, 15%, 20%, 25%, 30%, 35%, 40%, 45%, 50%, 55%, 60%, 65%, 70%, 75%, 80%, 85%, 90%, 95% or greater than 95% specific activity when conducting a reverse transcription reaction at an elevated temperature for at least about 1 minute, at least about 2 minutes, at least about 3 minutes, at least about 4 minutes, at least about 5 minutes, at least about 10 minutes, at least about 15 minutes, at least about 20 minutes, at least about 25 minutes, at least about 30 minutes, at least about 45 minutes, at least about an hour, at least about a day, at least about 2 days, at least about 3 days, at least about 4 days, at least about 5 days, at least about 6 days, or at least about 1 week. For example, such timeframe may be between 30 minutes and 1 day, 30 minutes and 75 minute, etc. In some cases, a non-natural RT provided herein retains at least 25% specific activity when conducting reverse transcription at a temperature of at least about 37° C. for at least 15 minutes. In some cases, a non-natural RT provided herein retains at least 25% specific activity when conducting reverse transcription at a temperature of at least about 37° C. for at least 30 minutes. In some cases, a non-natural RT provided herein retains at least 25% specific activity when conducting reverse transcription at a temperature of at least about 37° C. for at least 45 minutes. In some cases, a non-natural RT provided herein retains at least 25% specific activity when conducting reverse transcription at a temperature of at least about 37° C. for at least 1 hour. In some cases, a non-natural RT provided herein retains at least 25% specific activity when conducting reverse transcription at a temperature of at least about 37° C. for at least 2 hours. In some cases, a non-natural RT provided herein retains at least 25% specific activity when conducting reverse transcription at a temperature of at least about 37° C. for at least 3 hours. In some cases, a non-natural RT provided herein retains at least 25% specific activity when conducting reverse transcription at a temperature of at least about 37° C. for at least 6 hours. In some cases, a non-natural RT provided herein retains at least 50% specific activity when conducting reverse transcription at a temperature of at least about 37° C. for at least 15 minutes. In some cases, a non-natural RT provided herein retains at least 50% specific activity when conducting reverse transcription at a temperature of at least about 37° C. for at least 30 minutes. In some cases, a non-natural RT provided herein retains at least 50% specific activity when conducting reverse transcription at a temperature of at least about 37° C. for at least 45 minutes. In some cases, a non-natural RT provided herein retains at least 50% specific activity when conducting reverse transcription at a temperature of at least about 37° C. for at least 1 hour. In some cases, a non-natural RT provided herein retains at least 50% specific activity when conducting reverse transcription at a temperature of at least about 37° C. for at least 2 hours. In some cases, a non-natural RT provided herein retains at least 50% specific activity when conducting reverse transcription at a temperature of at least about 37° C. for at least 3 hours. In some cases, a non-natural RT provided herein retains at least 50% specific activity when conducting reverse transcription at a temperature of at least about 37° C. for at least 6 hours. In some cases, a non-natural RT provided herein retains at least 75% specific activity when conducting reverse transcription at a temperature of at least about 37° C. for at least 15 minutes. In some cases, a non-natural RT provided herein retains at least 75% specific activity when conducting reverse transcription at a temperature of at least about 37° C. for at least 30 minutes. In some cases, a non-natural RT provided herein retains at least 75% specific activity when conducting reverse transcription at a temperature of at least about 37° C. for at least 45 minutes. In some cases, a non-natural RT provided herein retains at least 75% specific activity when conducting reverse transcription at a temperature of at least about 37° C. for at least 1 hour. In some cases, a non-natural RT provided herein retains at least 75% specific activity when conducting reverse transcription at a temperature of at least about 37° C. for at least 2 hours. In some cases, a non-natural RT provided herein retains at least 75% specific activity when conducting reverse transcription at a temperature of at least about 37° C. for at least 3 hours. In some cases, a non-natural RT provided herein retains at least 75% specific activity when conducting reverse transcription at a temperature of at least about 37° C. for at least 6 hours. In some cases, a non-natural RT provided herein has at least 100% or greater specific activity when conducting reverse transcription at a temperature of at least about 37° C. for at least 15 minutes. In some cases, a non-natural RT provided herein has at least 100% or greater specific activity when conducting reverse transcription at a temperature of at least about 37° C. for at least 30 minutes. In some cases, a non-natural RT provided herein has at least 100% or greater specific activity when conducting reverse transcription at a temperature of at least about 37° C. for at least 45 minutes. In some cases, a non-natural RT provided herein has at least 100% or greater specific activity when conducting reverse transcription at a temperature of at least about 37° C. for at least 1 hour. In some cases, a non-natural RT provided herein has at least 100% or greater specific activity when conducting reverse transcription at a temperature of at least about 37° C. for at least 2 hours. In some cases, a non-natural RT provided herein has at least 100% or greater specific activity when conducting reverse transcription at a temperature of at least about 37° C. for at least 3 hours. In some cases, a non-natural RT provided herein retains has at least 100% or greater specific activity when conducting reverse transcription at a temperature of at least about 37° C. for at least 6 hours. In some cases, a non-natural RT provided herein has at least 150% or greater specific activity when conducting reverse transcription at a temperature of at least about 37° C. for at least 15 minutes. In some cases, a non-natural RT provided herein has at least 150% or greater specific activity when conducting reverse transcription at a temperature of at least about 37° C. for at least 30 minutes. In some cases, a non-natural RT provided herein has at least 150% or greater specific activity when conducting reverse transcription at a temperature of at least about 37° C. for at least 45 minutes. In some cases, a non-natural RT provided herein has at least 150% or greater specific activity when conducting reverse transcription at a temperature of at least about 37° C. for at least 1 hour. In some cases, a non-natural RT provided herein has at least 150% or greater specific activity when conducting reverse transcription at a temperature of at least about 37° C. for at least 2 hours. In some cases, a non-natural RT provided herein has at least 150% or greater specific activity when conducting reverse transcription at a temperature of at least about 37° C.

for at least 3 hours. In some cases, a non-natural RT provided herein retains has at least 150% or greater specific activity when conducting reverse transcription at a temperature of at least about 37° C. for at least 6 hours.

A non-natural RT provided herein may generate a high yield of cDNA when conducting reverse transcription at elevated temperatures (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.). In some cases, such temperature is between 65° C. and 75° C. For example, at elevated temperatures, a non-natural RT of the disclosure may generate a quantity of cDNA transcript (e.g, partial and/or full-length) that is at least about 25%, 30%, 35%, 40%, 45%, 50%, 55%, 60%, 65%, 70%, 75%, 80%, 85%, 90%, 95%, 100%, 150%, 200%, 250%, or at least about 300% of the amount of cDNA transcript (e.g., partial and/or full-length) produced by the same non-natural RT at a lower temperature (e.g., less than 37° C., less than 35° C.). In some cases, a non-natural RT of the disclosure may produce about the same amount of cDNA transcript at a lower temperature compared to the amount of cDNA product made by the same non-natural RT at the higher temperature. In some embodiments, a non-natural RT of the disclosure generates at least about 25% of the amount cDNA transcript (e.g., partial and/or full-length) produced by the same non-natural RT at a lower temperature (e.g., less than 37° C.). In some embodiments, a non-natural RT of the disclosure generates at least about 50% of the amount cDNA transcript (e.g., partial and/or full-length) produced by the same non-natural RT at a lower temperature (e.g., less than 37° C.). In some embodiments, a non-natural RT of the disclosure generates at least about 75% of the amount cDNA transcript (e.g., partial and/or full-length) produced by the same non-natural RT at a lower temperature (e.g., less than 37° C.). In some embodiments, a non-natural RT of the disclosure generates about 100% of the amount cDNA transcript (e.g., partial and/or full-length) produced by the same non-natural RT at a lower temperature (e.g., less than 37° C.).

The quantity of cDNA produced by a non-natural RT (e.g., chimeric) at an elevated temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.) may also be superior to that produced by a natural RT during a similar timeframe. In some cases, the amount of partial and/or full length cDNA transcript produced by a non-natural RT of the present disclosure at elevated reaction temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.) may be at least about 1.5-fold, 2-fold, 5-fold, 10-fold, 50-fold, 100-fold, 150-fold, 200-fold, 250-fold, 300-fold, 350-fold, 400-fold, 450-fold, 500-fold or greater than the amount of full-length product synthesized by a natural RT under similar conditions. In some cases, the amount of cDNA transcript (e.g., partial and/or full length) produced by a non-natural RT of the present disclosure at a reaction temperature of at least about 37° C. is at least about 50-fold greater than the amount of full-length product synthesized by a natural RT under similar conditions. In some cases, the amount of cDNA transcript (e.g., partial and/or full length) produced by a non-natural RT of the present disclosure at a reaction temperature of at least about 37° C. is at least about 100-fold greater than the amount of full-length product synthesized by a natural RT under similar conditions. In some cases, the amount of cDNA transcript (e.g., partial and/or full length) produced by a non-natural RT of the present disclosure at a reaction temperature of at least about 37° C. is at least about 150-fold greater than the amount of full-length product synthesized by a natural RT under similar conditions. In some cases, the amount of cDNA transcript (e.g., partial and/or full length) produced by a non-natural RT of the present disclosure at a reaction temperature of at least about 42° C. is at least about 50-fold greater than the amount of full-length product synthesized by a natural RT under similar conditions. In some cases, the amount of cDNA transcript (e.g., partial and/or full length) produced by a non-natural RT of the present disclosure at a reaction temperature of at least about 42° C. is at least about 100-fold greater than the amount of full-length product synthesized by a natural RT under similar conditions. In some cases, the amount of cDNA transcript (e.g., partial and/or full length) produced by a non-natural RT of the present disclosure at a reaction temperature of at least about 42° C. is at least about 150-fold greater than the amount of full-length product synthesized by a natural RT under similar conditions.

Non-natural (e.g., chimeric) RTs of the present disclosure may exhibit increased thermostability in the presence or absence of an RNA template. In some instances, chimeric RTs of the disclosure may show an increased thermostability in both the presence and absence of an RNA template. The increase in thermostability may be measured by comparing suitable parameters of the chimeric RTs to those of a corresponding non-chimeric RTs.

In some cases, thermostability can be determined by pre-incubating the non-natural or chimeric RT at elevated temperatures (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.) and subsequently determining the ability of the non-natural RTs to produce partial and/or full length cDNA product at a certain reaction temperature, for example a reaction temperature which is lower than the pre-incubation temperature. Pre-incubation steps may be used, for example, during reverse transcription to reduce the presence of RNA secondary structure since reduction of secondary structure may increase the cDNA yield or reduce errors. The duration of a pre-incubation step can be any reasonable period of time (e.g., at least about 5 minutes, at least about 10 minutes, at least about 15 minutes, at least about 20 minutes, at least about 25 minutes, at least about 30 minutes, at least about 45 minutes, at least about an hour or longer than an hour). Following the pre-incubation and reverse transcription, the cDNA can be amplified, for example by PCR amplification and then analyzed.

Thermal stability of proteins can be investigated using various other methods including but not limited to fluorescence analysis, biochemical assays, circular dichroism, hydrogen exchange-mass spectroscopy, protein crystallization, and/or differential scanning calorimetry. Thermal stability may also be determined, for example in the case of enzymatic proteins, by assaying for enzymatic activity at varying temperatures.

A non-natural RT provided herein may exhibit particularly high specific activity. As used herein, the term specific activity is generally described in units/mg (U/mg) or units/μg (U/μg) wherein one unit (U) refers to the amount of enzyme that incorporates 1 nmol of dTTP in a RNA-directed DNA polymerization reaction using a poly(rA) as a template and an oligo(dT) as a primer in about 10 minutes at a reaction temperature of about 37° C. Various methods for measuring RT activity are available and include for example, radioactive nucleotide or fluorophore-labeled nucleotide incorporation assays.

In some embodiments, a non-natural RT provided herein may have a RNA-directed DNA polymerase specific activity of at least about 150 U/μg, at least about 200 U/μg, at least about 250 U/μg, at least about 300 U/μg, at least about 350 U/μg, at least about 400 U/μg, at least about 450 U/μg, at least about 500 U/μg, at least about 550 U/μg, at least about 600 U/μg, at least about 650 U/μg, at least about 700 U/μg, at least about 750 U/μg, at least about 800 U/μg, at least about 850 U/μg, at least about 900 U/μg, at least about 950 U/μg, at least about 1,000 U/μg, at least about 1,100 U/μg, at least about 1,200 U/μg, at least about 1,300 U/μg, at least about 1,400 U/μg, at least about 1,500 U/μg, at least about 1,600 U/μg, at least about 1,700 U/μg, at least about 1,800 U/μg, at least about 1,900 U/μg, at least about 2,000 U/μg, at least about 2,500 U/μg, at least about 3,000 U/μg, at least about 3,500 U/μg, at least about 4,000 U/μg, at least about 5,000 U/μg, at least about 6,000 U/μg, at least about 7,000 U/μg, at least about 8,000 U/μg, at least about 9,000 U/μg, at least about 10,000 U/μg, at least about 11,000 U/μg, at least about 12,000 U/μg, at least about 13,000 U/μg, at least about 14,000 U/μg, at least about 15,000 U/μg, at least about 16,000 U/μg, at least about 17,000 U/μg, at least about 18,000 U/μg, at least about 19,000 U/μg, at least about 20,000 U/μg, at least about 21,000 U/μg, at least about 22,000 U/μg, at least about 23,000 U/μg, at least about 24,000 U/μg, at least about 25,000 U/μg, at least about 26,000 U/μg, at least about 27,000 U/μg, at least about 28,000 U/μg, at least about 29,000 U/μg, at least about 30,000 U/μg, at least about 31,000 U/μg, at least about 32,000 U/μg, at least about 33,000 U/μg, at least about 34,000 U/μg, at least about 35,000 U/μg, at least about 36,000 U/μg, at least about 37,000 U/μg, at least about 38,000 U/μg, at least about 39,000 U/μg, at least about 40,000 U/μg, at least about 41,000 U/μg, at least about 42,000 U/μg, at least about 43,000 U/μg, at least about 44,000 U/μg, at least about 45,000 U/μg, at least about 50,000 U/μg, at least about 100,000 U/μg, at least about 150,000 U/μg, at least about 200,000 U/μg, or at least about 250,000 U/μg. In some instances, the non-natural RT exhibits a specific activity of at least about 250 U/μg. In some examples, the non-natural RT exhibits a specific activity of at least about 450 U/μg. In some instances, the non-natural RT exhibits a specific activity of at least about 800 U/μg. In some instances, the non-natural RT exhibits a specific activity of at least about 1,000 U/μg. In some instances, the non-natural RT exhibits a specific activity of at least about 5,000 U/μg. In some instances, the non-natural RT exhibits a specific activity of at least about 10,000 U/μg. In some instances, the non-natural RT exhibits a specific activity of less than about 10,000 U/μg. In some instances, the non-natural RT exhibits a specific activity of at least about 15,000 U/μg. In some instances, the non-natural RT exhibits a specific activity of at least about 20,000 U/μg. In some instances, the non-natural RT exhibits a specific activity of less than about 20,000 U/μg. In some instances, the non-natural RT exhibits a specific activity of at least about 25,000 U/μg. In some instances, the non-natural RT exhibits a specific activity of at least about 30,000 U/μg. In some instances, the non-natural RT exhibits a specific activity of at least about 35,000 U/μg. In some instances, the non-natural RT exhibits a specific activity of at least about 40,000 U/μg. In some instances, the non-natural RT exhibits a specific activity of at least about 45,000 U/μg. In some instances, the non-natural RT exhibits a specific activity of at least about 10,000 U/μg to about 45,000 U/μg.

A non-natural RT disclosed herein may exhibit a high specific activity in comparison to a wild-type RT, particularly a natural or wild-type form of the RT. In some cases, a non-natural RT disclosed herein may have specific activity that is at least about 5% greater than its natural (e.g., wild-type or natural) form, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 150%, at least about 200%, at least about 250%, at least about 300%, at least about 350%, at least about 400%, or at least about 450% greater than its natural form. In some cases, a non-natural or chimeric reverse transcriptase may have specific activity that is at least about 0.1-fold, 0.2-fold, 0.3-fold, 0.4-fold, 0.5-fold, 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 250-fold, 300-fold, 350-fold, 400-fold, 450-fold, or 500-fold the specific activity of its wild-type form. A non-natural RT that has greater reverse transcriptase activity than a natural RT may be able to better generate cDNA product from RNA template that is of low quality and/or low quantity.

A non-natural RT provided herein may exhibit high processivity as it may promote the generation of cDNA (single-stranded or double-stranded) with a particularly long length. For example, a non-natural or chimeric RT provided herein may be able to synthesize partial and/or full length cDNA product at least about 500 bp (e.g., at least about 1 kb, at least about 2 kb, at least about 3 kb, at least about 4 kb, at least about 5 kb, at least about 6 kb, at least about 7 kb, at least about 8 kb, at least about 9 kb, at least about 10 kb or longer than 10 kb) in length. In some instances, a non-natural or chimeric RT provided herein may be able to synthesize cDNA product and/or full length cDNA product between about 500 bp and 15 kb in length (e.g., between about 750 bp and 12.5 kb in length, between about 1 kb and 10 kb in length, between about 2 kb and 9 kb in length, between about 3 kb and 8 kb in length, between about 4 kb and 7 kb in length, or between about 5 kb and 6 kb in length).

In some cases, a non-natural RT provided herein may exhibit high efficiency, high accuracy, high yield, high specificity and/or high fidelity, particularly when compared with a natural RT. Efficiency, for example, may be determined, by quantifying the cDNA yield from reverse transcription for a given amount of template RNA. Efficiency can be determined relative to a reference, for example the efficiency of a non-natural RT can be determined relative to the efficiency of a natural RT. In some cases, efficiency may refer to the proportion of full-length product to total product (e.g., full-length and partial product). In some cases, efficiency may refer to the ability of a RT to reverse transcribe low quality and/or low quantities of RNA template. Efficiency may be determined by quantifying cDNA yield during reverse transcription, for example using quantitative reverse transcription PCR or RT-qPCR, and/or at the completion of reverse transcription, for example using an agarose gel for quantification or other DNA detection method, such as with a spectrophotometer.

In some examples, the efficiency of the RTs described herein may be increased relative to non-chimeric RTs (e.g., natural, wild-type RTs), by at least 5%, 10%, 15%, 20%, 25%, 30%, 35%, 40%, 45%, 50%, 55%, 60%, 65%, 70%, 75%, 80%, 85%, 90%, 95% or greater than 95%. In some cases, a non-natural or chimeric reverse transcriptase may have an efficiency that is at least about 0.1-fold, 0.2-fold, 0.3-fold, 0.4-fold, 0.5-fold, 1-fold, 2-fold, 3-fold, 4-fold, 5-fold, 10-fold or greater than 10-fold the efficiency of its wild-type or natural form. In such examples in particular, the non-natural RT may exhibit a greater yield of cDNA product compared to, for example, a natural RT.

Peptide Tag

In some embodiments, at least one peptide tag is linked to non-natural (e.g., chimeric) RTs and other proteins (e.g., enzymes) of the disclosure. The at least one peptide tag may function as stability enhancing tag. The non-natural RTs herein may be linked to at least two (e.g., at least three, four, five or more) peptide tags which function as stability enhancing tags. Stability enhancing peptide tags may enhance the stability of proteins (e.g., thermostable enzymes, non-thermostable enzymes) following short-term or long-term exposure to a temperature between about −20° C. and about +65° C., between about −20° C. and about +60° C., between about −20° C. and about +55° C., between about −20° C. and about +50° C., between about −20° C. and about +45° C., between about −20° C. and about +40° C., between about −20° C. and about +35° C., between about −20° C. and about +30° C., between about −20° C. and about +25° C., between about −20° C. and about +20° C., between about −20° C. and about +15° C., between about −20° C. and about +10° C., between about −20° C. and about +5° C., between about −20° C. and about 0° C., between about −20° C. and about +65° C., between about −15° C. and about +65° C., between about −10° C. and about +65° C., between about −5° C. and about +65° C., between about 0° C. and about +65° C., between about 5° C. and about +65° C., between about 10° C. and about +65° C., between about 15° C. and about +65° C., between about 20° C. and about +65° C., between about 25° C. and about +65° C., between about 30° C. and about +65° C., between about 35° C. and about +65° C., between about 40° C. and about +65° C., between about 45° C. and about +65° C., between about 50° C. and about +65° C., between about 55° C. and about +65° C., or between about 60° C. and about +65° C. In some cases, the stability enhancing peptide tags can enhance the stability of proteins following exposure to various temperatures above room temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 45° C., at least about 50° C., at least about 55° C., at least about 60° C., at least about 65° C., at least about 70° C., at least about 75° C., at least about 80° C., at least about 85° C., or at least about 90° C.). The peptide tags may aid the retention of protein structure, stability, enzymatic activity, binding activity, any other property, or any combination thereof. In some embodiments, the chimeric RTs linked to stability enhancing peptide tags may demonstrate enhanced stability or enzymatic activity when compared to a similar protein that does not have the tag, especially after short-term or long-term exposure to a certain temperature (e.g., temperatures of room temperature or above).

In some cases, a stability enhancing peptide tag comprises a motif comprising at least one to six histidine residues. In some cases, a stability enhancing peptide comprises a protease cleavage site comprising the amino acid sequence DDDDK (SEQ ID NO: 19). A stability enhancing peptide can comprise the conserved sequence HHHHHHPWDYKDDDDKPRWNS (SEQ ID NO: 20), which includes six histidine residues and a protease cleavage site. A stability enhancing peptide tag may be of any suitable length, e.g., at least 20 amino acids, at least 25 amino acids, at least 30 amino acids, at least 35 amino acids, at least 40 amino acids, at least 45 amino acids, or at least 50 amino acids in length. In some cases, a stability enhancing peptide tag may comprise the sequence MIDLQRPQAATMDSRHHHHHHPWDYKDDDDKPRWNS (SEQ ID NO: 18). A stability enhancing tag may comprise a sequence that is at least 75%, 80%, 85%, 90%, 95%, 96%, 97%, 98%, or 99% identical to SEQ ID NO: 18 and comprises the sequence of SEQ ID NO: 20.

In some embodiments, a non-natural (e.g., chimeric) RT comprises a ribonuclease domain from *T. thermophilus* or a variant thereof (e.g., a variant having reduced ribonuclease activity) linked to a polymerase domain from M-MLV RT or a variant thereof which is further linked to a stability enhancing peptide tag (SEQ ID NO: 14, the peptide tag sequence is indicated by the underlined sequence). In some embodiments, a chimeric RT comprises a ribonuclease domain from *T. litoralis* (e.g., RNase H II) or a variant thereof (e.g., a variant having reduced ribonuclease activity) linked to a polymerase domain from M-MLV RT or a variant thereof which is further linked to a stability enhancing peptide tag (SEQ ID NO: 15, the peptide tag sequence is indicated by the underlined sequence). In some embodiments, a chimeric RT comprises a ribonuclease domain from *T. gammatolerans* or a variant thereof (e.g., a variant having reduced ribonuclease activity) linked to a polymerase domain from M-MLV RT or a variant thereof which is further linked to a stability enhancing peptide tag.

In some embodiments, a chimeric reverse transcriptase comprises a ribonuclease domain from *T. thermophilus* or a variant thereof (e.g. a variant having reduced ribonuclease activity) linked to a polymerase domain from HIV-1 RT or a variant thereof which is further linked to a stability enhancing peptide tag (SEQ ID NO: 16, the peptide tag sequence is indicated by the underlined sequence). In some embodiments, a chimeric RT comprises a ribonuclease domain from *T. litoralis* (e.g., RNase H II) or a variant thereof (e.g., a variant having reduced ribonuclease activity) linked to a polymerase domain from HIV-1 RT or a variant thereof which is further linked to a stability enhancing peptide tag (SEQ ID NO: 17, the peptide tag sequence is indicated by the underlined sequence). In some embodiments, a chimeric RT comprises a ribonuclease domain from *T. gammatolerans* or a variant thereof (e.g., a variant having reduced ribonuclease activity) linked to a polymerase domain from HIV-1 RT or a variant thereof which is further linked to a stability enhancing peptide tag.

In some cases, a chimeric reverse transcriptase may comprise an amino acid sequence of any of SEQ ID NOs: 14-17. In some cases, a chimeric reverse transcriptase may comprise an amino acid sequence at least 75%, at least 80%, at least 85%, at least 90%, at least 91%, at least 92%, at least 93%, at least 94%, at least 95%, at least 96%, at least 97%, at least 98%, or at least 99% identical to of any of SEQ ID NOs: 14-17.

TABLE 3

Amino acid sequence of chimeric RTs including stability enhancing peptide tag

| SEQ ID NO: | Description | Amino Acid Sequence |
|---|---|---|
| 13 | Tag - wt M-MLV | MIDLQRPQAATMDSRHHHHHHMPWDYKDDDDKPRWNSLN IEDEHRLHETSKEPDVSLGSTWLSDFPQAWAETGGMGLAV RQAPLIIPLKATSTPVSIKQYPMSQEARLGIKPHIQRLLDQGI LVPCQSPWNTPLLPVKKPGTNDYRPVQDLREVNKRVEDIH PTVPNPYNLLSGLPPSHQWYTVLDLKDAFFCLRLHPTSQPL FAFEWRDPEMGISGQLTWTRLPQGFKNSPTLFDEALHRDL ADFRIQHPDLILLQYVDDLLLAATSELDCQQGTRALLQTLG NLGYRASAKKAQICQKQVKYLGYLLKEGQRWLTEARKET VMGQPTPKTPRQLREFLGTAGFCRLWIPGFAEMAAPLYPL TKTGTLFNWGPDQQKAYQEIKQALLTAPALGLPDLTKPFE LFVDEKQGYAKGVLTQKLGPWRRPVAYLSKKLDPVAAG WPPCLRMVAAIAVLTKDAGKLTMGQPLVILAPHAVEALV KQPPDRWLSNARMTHYQALLLDTDRVQFGPVVALNPATL LPLPEEGLQHNCLDILAEAHGTRPDLTDQPLPDADHTWYT DGSSLLQEGQRKAGAAVTTETEVIWAKALPAGTSAQRAEL IALTQALKMAEGKKLNVYTDSRYAFATAHIHGEIYRRRGL LTSEGKEIKNKDEILALLKALFLPKRLSIIHCPGHQKGHSAE ARGNRMADQAARKAAITETPDTSTLLI |
| 14 | Tag - M-MLV pol domain - Tth RNase H⁻ | MIDLQRPQAATMDSRHHHHHHPWDYKDDDDKPRWNSLN IEDEHRLHETSKEPDVSLGSTWLSDFPQAWAETGGMGLAV RQAPLIIPLKATSTPVSIKQYPMSQEARLGIKPHIQRLLDQGI LVPCQSPWNTPLLPVKKPGTNDYRPVQDLREVNKRVEDIH PTVPNPYNLLSGLPPSHQWYTVLDLKDAFFCLRLHPTSQPL FAFEWRDPEMGISGQLTWTRLPQGFKNSPTLFDEALHRDL ADFRIQHPDLILLQYVDDLLLAATSELDCQQGTRALLQTLG NLGYRASAKKAQICQKQVKYLGYLLKEGQRWLTEARKET VMGQPTPKTPRQLREFLGTAGFCRLWIPGFAEMAAPLYPL TKTGTLFNWGPDQQKAYQEIKQALLTAPALGLPDLTKPFE LFVDEKQGYAKGVLTQKLGPWRRPVAYLSKKLDPVAAG WPPCLRMVAAIAVLTKDAGKLTMGQPLVILAPHAVEALV KQPPDRWLSNARMTHYQALLLDTDRVQFGPVVALNPATL LPLPEEGLQHNCLDILAEAHGTRPDLTDQPLPDNPSPRKRV ALFTNGACLGNPGPGGWAALLRFHAHEKLLSGGEACT TNNRMELKAAIEGLKALKEPCEVDLYTDSHYLKKAFTE GWLEGWRKRGWRTAEGKPVKNRDLWEALLLAMAPH RVRFHFVKGHTGHPENERVDREARRQAQSQAKTPCPP RAPTLFHEEA |
| 15 | Tag - M-MLV pol domain - Tli Rnase H II⁻ | MIDLQRPQAATMDSRHHHHHHPWDYKDDDDKPRWNSLN IEDEHRLHETSKEPDVSLGSTWLSDFPQAWAETGGMGLAV RQAPLIIPLKATSTPVSIKQYPMSQEARLGIKPHIQRLLDQGI LVPCQSPWNTPLLPVKKPGTNDYRPVQDLREVNKRVEDIH PTVPNPYNLLSGLPPSHQWYTVLDLKDAFFCLRLHPTSQPL FAFEWRDPEMGISGQLTWTRLPQGFKNSPTLFDEALHRDL ADFRIQHPDLILLQYVDDLLLAATSELDCQQGTRALLQTLG NLGYRASAKKAQICQKQVKYLGYLLKEGQRWLTEARKET VMGQPTPKTPRQLREFLGTAGFCRLWIPGFAEMAAPLYPL TKTGTLFNWGPDQQKAYQEIKQALLTAPALGLPDLTKPFE LFVDEKQGYAKGVLTQKLGPWRRPVAYLSKKLDPVAAG WPPCLRMVAAIAVLTKDAGKLTMGQPLVILAPHAVEALV KQPPDRWLSNARMTHYQALLLDTDRVQFGPVVALNPATL LPLPEEGLQHNCLDILAEAHGTRPDLTDQPLPDKLGGINQ AGRGPVIGPLVIAAVVVDESRMQELEALGVKDSKKLTP KRREELFEEIVQIVDDHVIIQLSPEEIDGRDGTMNELEIE NFAKALNSLKVKPDVLYIDAADVKEKRFGDIIGERLSFS PKIIAEHKADSKYIPVAAASILAKVTRDRAIEKLKELYGE IGSGYPSDPNTRRFLEEYYKAHGEFPPIVRKSWKTLRKI EEKLKAKKTQPTILDFLKKP |

TABLE 3-continued

Amino acid sequence of chimeric RTs including stability enhancing peptide tag

| SEQ ID NO: | Description | Amino Acid Sequence |
|---|---|---|
| 16 | Tag - HIV-1 pol domain - Tth Rnase H⁻ | MIDLQRPQAATMDSRHHHHHHPWDYKDDDDKPRWNSNF PISPIETVPVKLKPGMDGPKVKQWPLTEEKIKALVEICTEM EKEGKISKIGPENPYNTPVFAIKKKDSTKWRKLVDFRELNK RTQDFWEVQLGIPHPAGLKKKKSVTVLDVGDAYFSVPLDE DFRKYTAFTIPSINNETPGIRYQYNVLPQGWKGSPAIFQSSM TKILEPFRKQNPDIVIYQYMDDLYVGSDLEIGQHRTKIEELR QHLLRWGLTTPDKKHQKEPPFLWMGYELHPDKWTVQPIV LPEKDSWTVNDIQKLVGKLNWASQIYPGIKVRQLCKLLRG TKALTEVIPLTEEAELELAENREILKEPVHGVYYDPSKDLIA EIQKQGQGQWTYQIYQEPFKNLKTGKYARMRGAHTNDVK QLTEAVQKITTESIVIWGKTPKFKLPIQKETWETWWTEYW QATWIPEWEFVNTPPLVKLWYQLEKEPIVNPSPRKRVALF TNGACLGNPGPGGWAALLRFHAHEKLLSGGEACTTNN RMELKAAIEGLKALKEPCEVDLYTDSHYLKKAFTEGW LEGWRKRGWRTAEGKPVKNRDLWEALLLAMAPHRV RFHFVKGHTGHPENERVDREARRQAQSQAKTPCPPRA PTLFHEEA |
| 17 | Tag - HIV-1 pol domain - Tli Rnase H II⁻ | MIDLQRPQAATMDSRHHHHHHPWDYKDDDDKPRWNSNF PISPIETVPVKLKPGMDGPKVKQWPLTEEKIKALVEICTEM EKEGKISKIGPENPYNTPVFAIKKKDSTKWRKLVDFRELNK RTQDFWEVQLGIPHPAGLKKKKSVTVLDVGDAYFSVPLDE DFRKYTAFTIPSINNETPGIRYQYNVLPQGWKGSPAIFQSSM TKILEPFRKQNPDIVIYQYMDDLYVGSDLEIGQHRTKIEELR QHLLRWGLTTPDKKHQKEPPFLWMGYELHPDKWTVQPIV LPEKDSWTVNDIQKLVGKLNWASQIYPGIKVRQLCKLLRG TKALTEVIPLTEEAELELAENREILKEPVHGVYYDPSKDLIA EIQKQGQGQWTYQIYQEPFKNLKTGKYARMRGAHTNDVK QLTEAVQKITTESIVIWGKTPKFKLPIQKETWETWWTEYW QATWIPEWEFVNTPPLVKLWYQLEKEPIVKLGGINQAGR GPVIGPLVIAAVVVDESRMQELEALGVKDSKKLTPKRR EELFEEIVQIVDDHVIIQLSPEEIDGRDGTMNELEIENFA KALNSLKVKPDVLYIDAADVKEKRFGDIIGERLSFSPKII AEHKADSKYIPVAAASILAKVTRDRAIEKLKELYGEIGS GYPSDPNTRRFLEEYYKAHGEFPPIVRKSWKTLRKIEE KLKAKKTQPTILDFLKKP |
| 18 | Tag | MIDLQRPQAATMDSRHHHHHHPWDYKDDDDKPRWNS |
| 19 | Protease cleavage site | DDDDK |
| 20 | Peptide tag | HHHHHHPWDYKDDDDKPRWNS |

Kits

In some embodiments, the present disclosure provides kits comprising one or more non-natural (e.g., chimeric) RTs disclosed herein. The chimeric RTs may be directly formulated into compositions and provided in kits for conducting assays involving reverse transcription. A kit comprising non-natural RTs disclosed herein may include the chimeric RTs formulated as a solution (for example an aqueous solution, a glycerol solution, etc) or as a lyophilized powder which is reconstituted prior to use or according to other instructions provided with the kit. A kit may include a first container (e.g., tube, vial, ampule) that contains one or more non-natural (e.g., chimeric) RTs disclosed herein and at least a second container containing one or more other components (e.g., polymerase, DNA polymerase, DNA-dependent DNA polymerase, dNTPs, buffer for nucleic acid synthesis, reagent, dye). The individual components of the kit described herein can be present in separate containers, or some components may be present as a mixture in the same container. In preferred embodiments the kits provided herein contain a DNA-dependent DNA polymerase, which may, in some cases, be present in a separate container from the chimeric RT. In some cases, the DNA-dependent DNA polymerase is mixed with the chimeric RT in the same container. The DNA-dependent DNA polymerase may be present in solution or, for example, as a lyophilized powder.

Kits comprising non-natural, chimeric RTs for conducting assays involving reverse transcription may further comprise reaction media(s) or buffer(s) which can be optimized for reverse transcription or enzyme storage. Appropriate reaction media or buffers for kits comprising chimeric RTs may permit reverse transcription with a pre-incubation step and/or at elevated reaction temperatures, and optionally nucleic acid amplification according to the methods provided herein (e.g., in 1 step RT-PCR or 2 step RT-PCR reactions). The pH of the media or buffer may be from about pH 5 to about pH 11, from about pH 6 to about pH 10, from about pH 7 to about pH 9, or from about pH 7.5 to about pH 8.5. More acidic and alkaline buffers may also be used. The pH of the media or buffer can be adjusted, for example, to optimize the enzymatic activity of either the chimeric RT and/or a DNA polymerase, if one is provided. The media or buffer may comprise Tris(hydroxymethyl)aminomethane (Tris). In some embodiments, the media or buffer can include about 50-80 mM Tris (e.g., at a pH of about pH 8.3 to pH 9.0) and about 10-20 mM $(NH_4)_2SO_4$ or about 30-50 mM KCl.

Other media or buffers may also be used, e.g., so long as the components are non-inhibitory to the enzyme components of the kit or minimally inhibit the enzyme components of the kit or can be removed before using the enzyme.

A kit may comprise reaction medium or buffer having bivalent metal ions such as Mg2+ or Mn2+. The final concentration of free ions may be within a range of from about 0.01 mM to about 15 mM, or from about 1 mM to about 10 mM. In some embodiments, the reaction medium or buffer comprises MgCl2 (e.g, at least about 1 mM, 1.5 mM, 2 mM, 5 mM, 7.5 mM, 10 mM, 15 mM, 20 mM, 25 mM, 30 mM, 40 mM or 50 mM of MgCl2 or greater than 50 mM of MgCl2). In some embodiments, the reaction medium or buffer can also include additional salts such as KCl and/or NaCl. Additional salts may contribute to the total ionic strength of the medium. For example, the range of a salt such as KCl may be from about 0 mM to about 125 mM (e.g., from about 0 mM to about 100 mM, from about 0 mM to about 75 mM, or from about 0 mM to about 50 mM). For example, the range of a salt such as NaCl may be from about 0 mM to about 125 mM (e.g., from about 0 mM to about 100 mM, from about 0 mM to about 75 mM, or from about 0 mM to about 50 mM). The reaction medium or buffer can further include additives that could affect reverse transcription and/or amplification. Such additives include, but are not limited to, proteins such as bovine serum albumin (BSA), single strand binding proteins, and non-ionic detergents such as NP40 or Triton.

Kits comprising non-natural RTs provided herein may also comprise reagents (e.g., dithiothreitol or DTT), that are capable of maintaining enzyme activities. In some embodiments, the kits comprising non-natural RTs provided herein can include a linear polyacrylamide (LPA), which can increase the specificity and sensitivity of an enzyme.

In some embodiments, a kit comprises at least one primer for synthesizing cDNA from a template RNA. Primers for synthesizing cDNA from a template RNA may be provided in solution. A primer for synthesizing cDNA from a template RNA may not be limited to a specific sequence so long as the nucleotide sequence of the primer is complementary (e.g., partially or fully) to that of the template RNA and can anneal to the template RNA under desired reaction conditions. In some cases, the primer comprises an oligo(dT), or an oligonucleotide comprising 'T' bases. An oligo(dT) can hybridize to poly-A sequences such as, for example, those found on mRNA. In some cases, the primer comprises an oligonucleotide having a random sequence (e.g., a random primer). In some cases, the primer comprises an oligonucleotide having a gene-specific sequence. A kit may further include oligonucleotide primers for amplification processes other than reverse transcription, for example for cDNA amplification. Primers for amplification processes other than reverse transcription can be provided in solution. In some embodiments, oligonucleotides provided in kits disclosed herein may be modified, for example with labels such as fluorophores, fluorescent moieties, and dyes.

In some embodiments, a composition of a kit may also comprise nucleotides, such as deoxynucleotide triphosphates (dNTPs) and/or dideoxynucleotide triphosphates (ddNTPs) (e.g., at least about 1 mM, 1.5 mM, 2 mM, 5 mM, 7.5 mM, 10 mM, 15 mM, 20 mM, 25 mM, 30 mM, 40 mM or 50 mM dNTPs or ddNTPs). The dNTPs may be ultrapure dNTPs. The dNTPs may comprise dATP, dGTP, dCTP, dTTP, dUTP, or any combination thereof. The dNTPs provided in a kit may be modified dNTPs or dNTP analogs. In some cases, dNTPs and ddNTPs can include "labels" which can be used, either directly or in combination with other molecules such as reporter molecules, for the detection of cDNA and/or amplification products (e.g., in RT-qPCR or quantitative reverse transcription PCR). Labels can comprise molecular structures that, once attached to a nucleic acid, provide a distinct characteristic that is not inherent to the dNTPs, ddNTPs, cDNA or amplified polynucleotides. In some cases, nucleotide and nucleotide analogs, including ddNTPs, can comprise fluorophores or fluorescent moieties (e.g., dyes) as labels.

The kits disclosed herein may comprise a DNA-binding dye, such as dyes that bind double-stranded DNA and emit a signal (e.g., a fluorescent signal). Non-limiting examples of DNA binding dyes include EvaGreen™, described in U.S. Pat. No. 7,601,498; LC Green; SYTO9; Chromofy; BEBO; and SYBR Green. Such dyes may be useful for quantitative PCR (qPCR) applications. The kits may, in some cases, comprise a reference dye (e.g., ROX dye), or a quencher dye (e.g., TAMRA). In some embodiments, the above mentioned reference dyes can be used in a variety of reactions, including reactions for real-time quantitative PCR including RT-qPCR.

A kit may further comprise an RNase inhibitor. An RNase inhibitor provided in a kit may inhibit RNases A, B, C, or any combination thereof. A RNase inhibitor provided in a kit may inhibit RNase 1, RNase T1, Si Nuclease, RNase H, RNase from *Aspergillus*, or any combination thereof. An RNase inhibitor provided in a kit may minimally inhibit the polymerase and/or RNase activity of the chimeric RT of the kit. Using an RNase inhibitor provided in a kit which does not inhibit or minimally inhibits the polymerase and/or RNase activity of the chimeric RT can prevent the premature degradation of RNA, e.g., mRNA, for example, before reverse transcription is completed or before a desired quantity of cDNA is obtained.

In some embodiments, the kits disclosed herein comprise a Uracil N-Glycosylase. In PCR assays, for example real-time PCR, UNG can reduce the potential for false positive reactions due to amplicon carryover. Uracil N-Glycosylase (UNG), which cleaves the uracil base from the phosphodiester backbone of uracil-containing DNA, but has no effect on natural (i.e., thymine-containing) DNA, can be used to eliminate carry-over PCR products in real-time PCR. When performing real-time PCR, dUTP can be provided instead of dTTP and the resulting amplicons from amplification can be distinguished from the starting template by the presence of uracil (vs. thymine). Prior to any subsequent amplification, uracil DNA-glycosylase (UNG) can be used to cleave these bases from any contaminating DNA, and therefore only the thymine-containing template remains intact and can be amplified.

In some embodiments, a kit provided herein comprises a DNA polymerase. The DNA polymerase may be provided in the same formulation as the chimeric RT, for example for use in a 1 step RT-PCR reaction. In some embodiments, the DNA polymerase is provided in a formulation different from the chimeric RT, for example for use in a 2 step RT-PCR reaction. In some embodiments, kits disclosed herein may include at least two polymerases. A kit, for example, may contain a main polymerase and a proof-reading polymerase. The main polymerase may be provided at a concentration of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, which may be wt %, vol %, or mol %, or a percentage of the total polymerase in the mix on a molar, mass, or volume basis. The composition may also contain a proof-reading polymerase (e.g., a Tgo based polymerase). The proof-reading polymerase may be present at a concentration of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, which may be wt %, vol %, or mol %, or a percentage of the total polymerase in the mix on a molar, mass, or volume basis. A variety of DNA polymerases are useful in accordance with the present disclosure. Such polymerases include, but are not limited to, *Thermus thermophilus* (Tth) DNA polymerase, *Thermus aquaticus* (Taq) DNA polymerase, *Thermotoga* neapolitana (Tne) DNA polymerase, *Thermotoga maritima* (Tma) DNA polymerase, *Thermococcus litoralis* (Tli or VENT™) DNA polymerase, *Thermococcus kodakaraensis* KOD1 DNA Polymerase, *Pyrococcus furiosis* (Pfu) DNA polymerase, *Pyrococcus* species GB-D (DEEPVENT™) DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* spp. DNA polymerase (Mtb, Mlep), and mutants, variants and derivatives thereof.

A kit provided herein may comprise a chimeric RT linked to a peptide tag, for example a peptide tag (e.g., SEQ ID NO: 18) that confers thermal stability to the chimeric RT. A DNA polymerase optionally provided in the kit may be linked to a peptide tag (e.g., SEQ ID NO: 18) that confers thermal stability to the DNA polymerase. An RNase inhibitor optionally provided in a kit may be linked to a peptide tag that confers thermal stability to the RNase inhibitor. A UNG optionally provided in a kit may also be linked to a peptide tag that confers thermal stability to the UNG. Peptide tags that confer thermal stability may allow kits comprising various combinations of the aforementioned components to be stored at room temperature or temperatures higher than room temperature (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., or at least about 40° C.) for certain periods of time, such as at least 1 day, 2 days, 3 days, 4 days, 5 days, 6 days, 1 week, 2 weeks, 3 weeks, 1 month, 2 months, 3 months, 4 months, 5 months, 6 months or longer than 6 months.

Any of the aforementioned components of a kit can be formulated as a master mix which is ready for use. The master mix can be provided in a single container, e.g., tube. The master mix, in some cases, is provided as a concentrated solution and is ready for use following the appropriate dilutions. For example, the solution may be about 1×, 2×, 3×, 4×, 5×, 10×, or greater than 15× concentration. Solutions formulated at concentrations greater than about 1× can be diluted prior to use. In some embodiments, a master mix for conducting reverse transcription can contain a chimeric reverse transcriptase and optionally a DNA polymerase (e.g., for amplification), optionally an additive (for example, bovine serum albumin or BSA), optionally a DNA tracking dye (for example, Bromophenol blue), optionally a DNA sample loading component (for example, glycerol), optionally a RNase inhibitor, and optionally a UNG. In some embodiments, the components are formulated as at least two master mixes which can be mixed together prior to use. The at least two master mixes can be provided in separate containers, e.g., tubes. Multiple master mixes may, for example, optimize the storage conditions for the various components of the kit.

A kit may further comprise instructions instructing the use of the various components. The instructions may include directions for formulating the reaction sample (including the relevant concentration of chimeric RT, DNA polymerase, RNase inhibitor, UNG, template, primers (reverse and forward), dNTPs, BSA, dyes, and H2O). The instructions may also include recommendations for running the reverse transcription and/or PCR cycle, such as the pre-incubation, denaturation, annealing, and elongation phases. Such instructions may include the temperature conditions and amount of time, temperature ramp rate, and/or number of cycles for each phase. In some embodiments, the foregoing components are added simultaneously at the initiation of the (optional) pre-incubation phase or combined reverse transcription and amplification phase. In some embodiments, components are added in any order prior to or after appropriate time points during the reverse transcription and amplification phases, as required and/or permitted by the reverse transcription and amplification reaction. The enzymes used for nucleic acid amplification can be added to the reaction mixture either prior to the target nucleic acid denaturation step (e.g., a pre-incubation step), following the denaturation step, or following hybridization of the primer to the target RNA or DNA, as determined by their thermal stability and/or other considerations.

Applications

This disclosure provides methods and compositions for conducting reverse transcription using the RTs provided herein. In some cases, the reverse transcription may include the following steps: (a) in an optional pre-incubation step, RNA template is incubated at an elevated temperature, optionally in the presence of a non-natural RT provided herein; (b) a DNA polymerase domain within a non-natural RT catalyzes the synthesis of cDNA from the RNA template; (c) optionally, RNase within the non-natural RT degrades the RNA in the resulting RNA-DNA hybrids; and (d) DNA-dependent DNA polymerase (either within the non-natural RT or separately added) catalyzes the synthesis of double-stranded DNA.

In some embodiments, reverse transcription is conducted using a chimeric RT provided herein and a DNA polymerase. The DNA polymerase may be provided in the same formulation as the chimeric RT, for example for use in a 1 step RT-PCR reaction. In some embodiments, the DNA polymerase is provided in a formulation different from the chimeric RT, for example for use in a 2 step RT-PCR reaction.

In some embodiments, a composition for conducting 1 step RT-PCR comprises at least two polymerases. The composition, for example, may comprise a chimeric RT and a DNA polymerase. The chimeric RT may be provided at a concentration of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, which may be wt %, vol %, or mol %, or a percentage of the total polymerase in the mix on a molar, mass, or volume basis. DNA polymerase may be present at a concentration of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, which may be wt %, vol %, or mol %, or a percentage of the total polymerase in the mix on a molar, mass, or volume basis. A variety of DNA polymerases are useful in accordance with the present disclosure. Such polymerases include, but are not limited to,

*Thermus thermophilus* (Tth) DNA polymerase, *Thermus aquaticus* (Taq) DNA polymerase, *Thermotoga* neapolitana (Tne) DNA polymerase, *Thermotoga maritima* (Tma) DNA polymerase, *Thermococcus litoralis* (Tli or VENT™) DNA polymerase, *Thermococcus kodakaraensis* KOD1 DNA Polymerase, *Pyrococcus furiosis* (Pfu) DNA polymerase, *Pyrococcus* species GB-D (DEEPVENT™) DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium* thermoautotrophicum (Mth) DNA polymerase, *Mycobacterium* spp. DNA polymerase (Mtb, Mlep), and mutants, variants and derivatives thereof.

cDNA molecules (single-stranded or double-stranded) may be produced from a variety of nucleic acid template molecules using non-natural (e.g., chimeric) RTs described herein. For example, nucleic acid template molecules may include single-stranded or double-stranded RNA (e.g., messenger RNA (mRNA), transfer RNA (tRNA) and ribosomal RNA (rRNA) molecules), as well as double-stranded DNA: RNA hybrids. Prior to reverse transcription and amplification, double-stranded molecules can be treated, for example by heat denaturation, to yield single-stranded molecules.

Nucleic acid template (e.g., RNA template) may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi, plants, protozoans and other parasites, and animals including insects, nematodes, and mammals such as human cells).

In some cases, nucleic acid template is obtained or derived from mammalian somatic cells. Mammalian somatic cells that may be used as sources of nucleic acids include blood cells (e.g., reticulocytes and leukocytes), endothelial cells, epithelial cells, neuronal cells (e.g., from the central or peripheral nervous systems), muscle cells (e.g., myocytes and myoblasts from skeletal, smooth or cardiac muscle), connective tissue cells (e.g., fibroblasts, adipocytes, chondrocytes, chondroblasts, osteocytes and osteoblasts) and other stromal cells (e.g., macrophages, dendritic cells, Schwann cells). In some cases, nucleic acid template is obtained or derived from mammalian germ cells (e.g., spermatocytes and oocytes). In some cases, nucleic acid template is obtained or derived from the progenitors, precursors and stem cells that give rise to the aforementioned somatic and germ cells. Nucleic acids can also be obtained or derived from mammalian tissues or organs such as the brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases such as those caused by bacteria, fungi or yeast, viruses (e.g., HIV, HTLV, herpes, hepatitis and the like) or parasites; in genetic or biochemical pathologies (e.g., cystic fibrosis, hemophilia, Alzheimer's disease, muscular dystrophy or multiple sclerosis); or in cancerous tissues.

In some embodiments, the RTs provided herein can be used to detect the presence of organisms in a sample, for example pathogenic organisms. The RTs provided herein may be thermal stable or have high specific activity, and may be particularly useful for clinical applications in hot or tropical climates, for example where temperatures are at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., or at least about 40° C.

The RTs provided herein may be thermally stable or have high specific activity, and may be particularly useful for cases where the RTs are to be transported and/or stored at elevated temperatures (e.g., temperatures of at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., or at least about 40° C.) for certain periods of time (e.g., for at least about a day, at least about 2 days, at least about 3 days, at least about 4 days, at least about 5 days, at least about 6 days, at least about 1 week, at least about 2 weeks, at least about 3 weeks, at least about 1 month, at least about 2 months, at least about 3, at least about 4 months, at least about 5 months, at least about 6 months or longer).

The RTs provided herein may be particularly useful in applications for detecting pathogenic microbes, e.g., disease-causing bacteria. Such bacteria that can cause disease include diphtheria (e.g., *Corynebacterium diphtheria*), pertussis (e.g., *Bordetella pertussis*), anthrax (e.g., *Bacillus anthracia*), typhoid, plague, shigellosis (e.g., *Shigella dysenteriae*), botulism (e.g., *Clostridium botulinum*), tetanus (e.g., *Clostridium tetani*), tuberculosis (e.g., *Mycobacterium tuberculosis*), bacterial pneumonias (e.g., *Haemophilus influenzae*), cholera (e.g., *Vibrio cholerae*), salmonellosis (e.g., *Salmonella typhi*), peptic ulcers (e.g., *Helicobacter pylori*), Legionnaire's Disease (e.g. *Legionella* spp.), and Lyme disease (e.g. *Borrelia burgdorferi*). Other pathogenic bacteria include *Clostridium perfringens, Clostridium difficile, Pseudomonas aeruginosa, Staphylococcus aureus*, and *Streptococcus pyogenes*. Further examples of bacteria include *Staphylococcus epidermidis, Staphylococcus* sp., *Streptococcus pneumoniae, Streptococcus agalactiae, Enterococcus* sp., *Bacillus cereus, Bifidobacterium bifidum, Lactobacillus* sp., *Listeria monocytogenes, Nocardia* sp *Rhodococcus equi, Erysipelothrix rhusiopathiae, Propionibacterium acnes, Actinomyces* sp., *Mobiluncus* sp., *Peptostreptococcus* sp *Neisseria gonorrhoeae, Neisseria meningitides, Moraxella catarrhalis, Veillonella* sp., *Actinobacillus actinomycetemcomitans, Acinetobacter baumannii, Brucella* sp *Campylobacter* sp., *Capnocytophaga* sp., *Cardiobacterium hominis, Eikenella corrodens, Francisella tularensis, Haemophilus ducreyi, Helicobacter pylori, Kingella kingae, Legionella pneumophila, Pasteurella multocida, Klebsiella granulomatis*, Enterobacteriaceae, *Citrobacter* sp., *Enterobacter* sp *Escherichia coli, Klebsiella pneumoniae, Proteus* sp., *Salmonella enteriditis, Salmonella typhi, Shigella* sp *Serratia marcescens, Yersinia enterocolitica, Yersinia pestis, Aeromonas* sp *Plesiomonas shigelloides, Vibrio cholerae, Vibrio parahaemolyticus,*

*Vibrio vulnificus, Acinetobacter* sp *Flavobacterium* sp., *Burkholderia cepacia, Burkholderia pseudomallei, Xanthomonas maltophilia, Stenotrophomonas maltophila, Bacteroides fragilis, Bacteroides* sp., *Prevotella* sp., *Fusobacterium*. sp., and *Spirillum minus*.

The non-natural RTs may also be used to detect disease-causing fungi. Fungi that can cause disease include *Acremoniuin* spp., *Aspergillus* spp., *Epidermophytoni* spp., *Exophiala jeanselmei, Exserohilunm* spp., *Fonsecaea compacta, Fonsecaea pedrosoi, Fusarium oxysporum, Basidiobolus* spp., *Bipolaris* spp., *Blastomyces derinatidis, Candida* spp., *Cladophialophora carrionii, Coccoidiodes immitis, Conidiobolus* spp., *Cryptococcus* spp., *Curvularia* spp., *Fusarium solani, Geotrichum candidum, Histoplasma capsulatum* var. *capsulatum, Histoplasma capsulatum* var. *duboisii, Hortaea werneckii, Lacazia loboi, Lasiodiplodia theobromas, Leptosphaeria senegalenisis, Piedra iahortae, Pityriasis versicolor, Pseudallesheria boydii, Pyrenochaeta romeroi, Rhizopus arrhizus, Scopulariopsis brevicaulis, Scytalidium dimidiatum, Sporothrix schenckii, Trichophyton* spp., *Trichosporon* spp., *Zygomcete fungi, Madurella grisea, Madurella mycetomatis, Malassezia furfur, Microsporum* spp., *Neotestudina rosatii, Onychocola canadensis, Paracoccidioides brasiliensis, Phialophora verrucosa, Piedraia hortae, Absidia coryinbifera, Rhizomucor pusillus*, and *Rhizopus arrhizus*.

The non-natural RTs may also be used to detect disease-causing viruses. Such viruses that can cause disease include, but are not limited to, Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16,18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, and Zika virus. In some embodiments, the non-natural RTs provided herein are used in assays to detect Zika virus.

The non-natural RTs may also be used to detect disease-causing protozoa. Illustrative examples of protozoa and other parasites that may cause disease can include, but are not limited to, malaria (e.g. *Plasmodium falciparum*), hookworm, tapeworms, helminths, whipworms, ringworms, roundworms, pinworms, ascarids, filarids, onchocerciasis (e.g., *Onchocerca volvulus*), schistosomiasis (e.g. *Schistosoma* spp.), toxoplasmosis (e.g. *Toxoplasma* spp.), trypanosomiasis (e.g. *Trypanosoma* spp.), leishmaniasis (*Leishmania* spp.), giardiasis (e.g., *Giardia lamblia*), amoebiasis (e.g., *Entamoeba histolytica*), filariasis (e.g., *Brugia malayi*), and trichinosis (e.g., *Trichinella spiralis*).

Uses of Synthesized cDNA

Following reverse transcription, the cDNA products (e.g., partial and/or full length product) may be used for further analysis or manipulation. The cDNA products can be optionally isolated and/or purified before proceeding. In some embodiments, cDNA produced using chimeric RTs provided herein may be further amplified, for example in one or more amplification reactions. Reverse transcription and nucleic acid amplification may be one-step (e.g., one-step RT-PCR) or two-step (e.g., two-step RT-PCR) reactions. A one-step RT-PCR type reaction may be accomplished in one tube, thereby lowering the possibility of contamination. Such one-step reactions may comprise (a) mixing a nucleic acid template (e.g., mRNA) with chimeric RT and a DNA polymerase and (b) incubating the mixture under conditions sufficient to permit cDNA synthesis and amplification. Two-step RT-PCR reactions may be accomplished in two separate steps. Such a method may comprise (a) mixing a nucleic acid template (e.g., mRNA) with a chimeric RT, (b) incubating the mixture under conditions sufficient to permit cDNA synthesis or first strand synthesis, (c) mixing the reaction mixture in (b) with one or more DNA polymerases and (d) incubating the mixture of step (c) under conditions sufficient to permit amplification. Optional pre-incubation steps may be used with one-step or two-step RT-PCR. For amplification of long nucleic acid molecules (e.g., greater than about 3-5 kb in length), a combination of DNA polymerases may be used, such as one DNA polymerase having 3'-5' exonuclease activity and another DNA polymerase being reduced in 3'-5' exonuclease activity.

Amplification methods which may be used include, but are not limited to, PCR, Strand Displacement Amplification (SDA), and Nucleic Acid Sequence-Based Amplification (NASBA). In some embodiments, amplification by PCR is preferred. In some embodiments, amplification may comprise isothermal amplification methods such as loop-mediated isothermal amplification (LAMP).

When RT-PCR is performed as two steps, the first step of reverse transcription can be conducted in a buffer optimized for RT activity and then a second step of PCR in another buffer condition optimized for PCR activity. Although these two steps can theoretically be combined, finding a single set of reaction conditions suitable for both steps can be challenging. For example, performing reverse transcription and amplification in one step may require an RT to have sufficient sensitivity and speed under conditions optimized for the amplification step; sufficient tolerance to high salt and to other potential inhibitors that may carry over from previous RNA sample preparation processes; and enhanced thermal stability. Performing reverse transcription at elevated temperatures with RTs having enhanced thermal stability may increase the sensitivity and/or speed of reverse transcription by minimizing RNA secondary structure.

As used herein, the terms "% identity" and "% identical" with reference to a sequence, such as a polynucleotide sequence or a polypeptide sequence, refer to comparisons among polynucleotides and polypeptides when the sequences are optimally aligned over a comparison window. The portion of the polynucleotide or polypeptide sequence in the comparison window may comprise additions or deletions (e.g., gaps) as compared to the reference sequence (which does not comprise additions or deletions) for optimal alignment of the two sequences. The percentage can be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology can be evaluated using any of the variety of available sequence comparison algorithms and programs. Such algorithms and programs include, but are not limited to, TBLASTN, BLASTP, FASTA, TFASTA, CLUSTALW, FASTDB. In some cases, protein and nucleic acid sequence homologies can be evaluated using the Basic Local Alignment Search Tool ("BLAST").

As used herein, the term "or" means "and/or" unless stated otherwise.

The term "about" as used herein, unless otherwise indicated, refers to a value that is no more than 10% above or below the value being modified by the term. For example, the term "about −20° C." means a range of from −22° C. to −18° C., including −22° C. and −18° C. As another example, "about 1 hour" means a range of from 54 minutes to 66 minutes, including 54 minutes and 66 minutes.

As used herein, the term "derived from" in connection with deriving a polypeptide (e.g., polypeptide domain) or a polynucleotide (e.g., polynucleotide domain) from a given source (e.g., a biological organism or microbe) may generally mean that the polypeptide or polynucleotide is identical to or a variant of (e.g., at least 50% identical) a polynucleotide or polypeptide sequence naturally present in the source organism. The term "derived from" is not meant to limit the method by which the molecule is made which can be, for example, by chemical synthesis or recombinant means and may, in many instances, occur without direct reference to the identity of the source organism.

EXAMPLES

Example 1—First Strand cDNA Synthesis

First strand cDNA synthesis was performed on 0.4 μg of total RNA with oligo(dT), at 37° C. for 60 minutes (min) using chimeric reverse transcriptases of the present disclosure. PCR amplification of cDNA was performed using DNA polymerase mix (HOT FIREPol® Blend Master Mix, Solis BioDyne) and β2M primers (~365 bp PCR product). The DNA product was examined on an agarose gel (FIG. 1).

Chimeric reverse transcriptases having a polymerase domain derived from M-MLV, both with and without a stabilizing peptide tag, possessed enzymatic activity (as indicated by the presence of amplification product on the agarose gel, lanes 3-6) whereas chimeric reverse transcriptases having a polymerase domain derived from HIV-1, both with and without a stabilizing peptide tag, exhibited diminished enzymatic activity (as indicated by minimal amplification product on the agarose gel, lanes 7-10).

Example 2—Molecular Weight Analysis of Chimeric Reverse Transcriptases

The molecular weight of chimeric reverse transcriptases disclosed herein was analyzed on a PageBlue stained 6% SDS-Polyacrylamide Gel (FIG. 2).

Example 3—Reverse Transcription Efficiency of Chimeric RTs Following Pre-Incubation Chimeric reverse transcriptases were pre-incubated for 15 minutes at 55° C., 60° C., 65° C. and 70° C. Pre-incubation can be used, for example, to minimize the presence of secondary structure that may be present in RNA template and interfere with reverse transcription. However, proteins, such as enzymes, that are not thermostable may lose their activity during pre-incubation.

Figure 3:
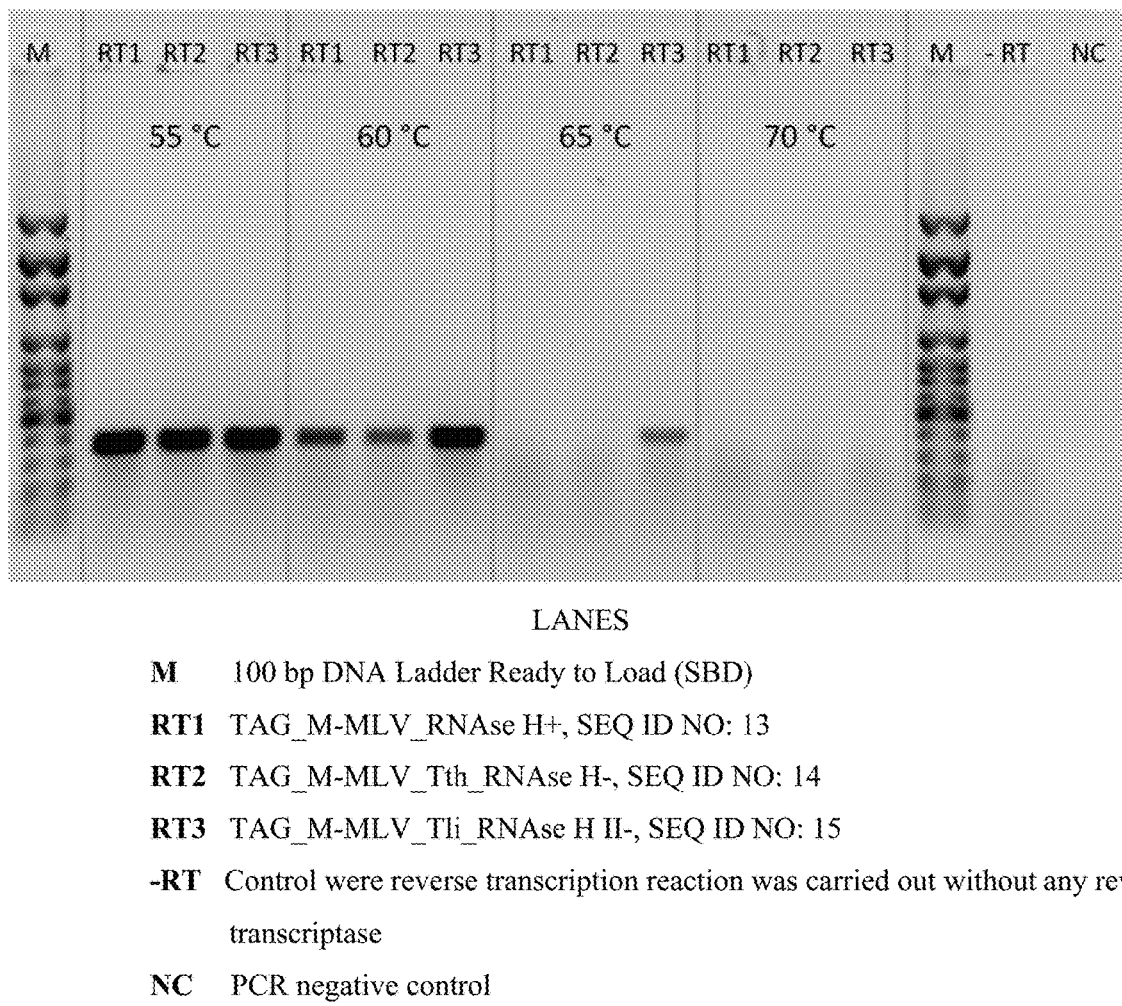
FIG. 3 shows DNA product from reverse transcription performed with non-natural reverse transcriptases following pre-incubation at elevated temperatures and subsequent amplification via a DNA polymerase.

After pre-incubation, first strand cDNA synthesis was performed on 0.4 μg of total RNA with oligo(dT) at 37° C. for 60 min. PCR amplification of cDNA was performed using DNA polymerase mix (HOT FIREPol® Blend Master Mix, Solis BioDyne) and β2M primers. The DNA product was examined on an agarose gel (FIG. 3).

Chimeric reverse transcriptases having a polymerase domain derived from M-MLV possessed enzymatic activity after pre-incubation at 55° C. and 60° C., as indicated by the presence of amplification product on the agarose gel. Chimeric reverse transcriptases having a polymerase domain derived from M-MLV and an RNase H II domain derived from *T. litoralis* possessed detectable enzymatic activity after pre-incubation at 65° C.

Example 4—Specific Activity of Chimeric RTs Compared to Wild-Type

In this example, a tagged, chimeric reverse transcriptase having a polymerase domain derived from M-MLV and an RNase H II domain derived from *T. litoralis* (TAG_M-MLV_Tli_RNase H II-, SEQ ID NO: 15) exhibited higher specific activity compared to tagged, wild-type M-MLV reverse transcriptase.

One unit of reverse transcriptase (RT) can refer to the amount of enzyme that incorporates 1 nanomol (nmol) of dTTP into acid-precipitable material in 10 minutes at 37° C. using poly(rA)-oligo(dT) as template-primer in a total reaction volume of 50 μL. For wild-type M-MLV, 1 μg of enzyme usually corresponds to 200 U/μL of RT activity (~200 U/μg).

Figure 4A:
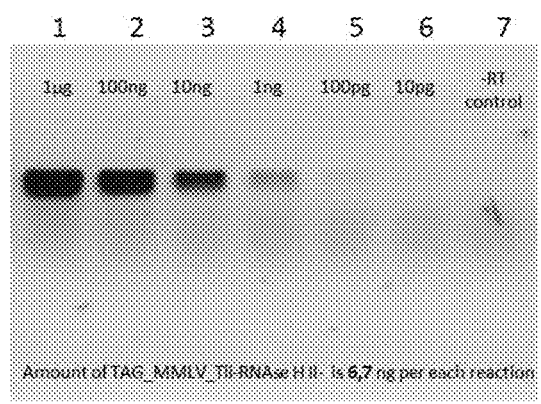
FIGS. 4A and 4B show the amplification product from first strand cDNA synthesis and PCR amplification using wild-type M-MLV RT and a chimeric RT disclosed herein with different amounts of template.
Figure 4B:
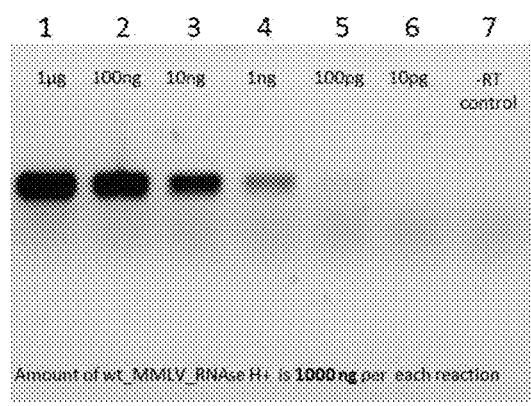

First strand cDNA synthesis was performed on a dilution series (10-fold) of total RNA with oligo(dT) at 37° C. for 60 minutes with wild-type M-MLV or the chimeric reverse transcriptase (SEQ ID NO: 15). PCR amplification of cDNA was performed using DNA polymerase mix (HOT FIREPol® Blend Master Mix, Solis BioDyne) and β2M primers. The PCR product (~365 bp) was examined on an agarose gel. For the same reaction conditions, first strand cDNA synthesis by ~6.7 ng of chimeric RT and then PCR amplification of cDNA is able to yield similar amounts of product (FIG. 4A) compared to first strand cDNA synthesis by 1000 ng of wild-type M-MLV (~150× the amount of chimeric RT used) and subsequent PCR amplification (FIG. 4B). The results of FIGS. 4A and 4B demonstrate that decreased amounts of chimeric RT has minimal effect on cDNA quantity and for a broad range of input RNA (e.g., from 10 pg to 1 μg). The specific activity of the chimeric RT of SEQ ID NO: 15 can be estimated to be about 200 U/μg×150≈30,000 U/μg.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for synthesizing complementary DNA (cDNA), comprising:
   (a) providing an RNA molecule template for cDNA synthesis,
   (b) providing a primer to initiate cDNA synthesis from the RNA molecule, and
   (c) synthesizing cDNA initiated by the primer from the RNA molecule template using a non-natural chimeric reverse transcriptase comprising:
      (i) a first domain comprising viral reverse transcriptase domain, and
      (ii) a second domain comprising a ribonuclease polypeptide having ribonuclease activity but not polymerase activity, wherein the ribonuclease polypeptide is an RNase polypeptide selected from the group consisting of: *Pyrococcus furiosus* RNase H, *Pyrococcus horikoshi* RNase H, *Thermococcus litoralis* RNase H II, *Thermus thermophilus* RNase H, and *Escherichia coli* RNase H;
   wherein the non-natural protein retains at least 25% of its reverse transcriptase activity at 37° C. after incubation at a temperature of at least 60° C. for at least 10 minutes.

2. The method of claim 1, wherein the ribonuclease polypeptide is an extremophile RNase polypeptide.

3. The method of claim 1, wherein the ribonuclease polypeptide is *Thermococcus litoralis* RNase H.

4. The method of claim 1, wherein the ribonuclease polypeptide comprises an RNase domain.

5. The method of claim 1, wherein the ribonuclease polypeptide comprises an RNase H II domain.

6. The method of claim 5, wherein the RNase H II domain comprises a mutated RNase H II domain.

7. The method of claim 1, wherein the ribonuclease polypeptide comprises an amino acid sequence at least 85% identical to SEQ ID NO: 22.

8. The method of claim 7, wherein the ribonuclease polypeptide comprises an amino acid sequence at least 95% identical to SEQ ID NO: 22.

9. The method of claim 1, wherein the non-natural protein comprises an amino acid sequence at least 85% identical to SEQ ID NO: 10, SEQ ID NO: 12, SEQ ID NO: 15, or SEQ ID NO: 17.

* * * * *

SEQUENCE LISTING

```
<160> NUMBER OF SEQ ID NOS: 27

<210> SEQ ID NO 1
<211> LENGTH: 671
<212> TYPE: PRT
<213> ORGANISM: Moloney murine leukemia virus

<400> SEQUENCE: 1

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
            20                  25                  30

Ala Glu Thr Gly Gly Met Gly Leu Ala Val Arg Gln Ala Pro Leu Ile
        35                  40                  45

Ile Pro Leu Lys Ala Thr Ser Thr Pro Val Ser Ile Lys Gln Tyr Pro
    50                  55                  60

Met Ser Gln Glu Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Gly Leu Pro Pro Ser His Gln Trp
    130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
            260                 265                 270

Lys Glu Gly Gln Arg Trp Leu Thr Glu Ala Arg Lys Glu Thr Val Met
        275                 280                 285

Gly Gln Pro Thr Pro Lys Thr Pro Arg Gln Leu Arg Glu Phe Leu Gly
    290                 295                 300
```

```
Thr Ala Gly Phe Cys Arg Leu Trp Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
                340                 345                 350

Ala Pro Ala Leu Gly Leu Pro Asp Leu Thr Lys Pro Phe Glu Leu Phe
            355                 360                 365

Val Asp Glu Lys Gln Gly Tyr Ala Lys Gly Val Leu Thr Gln Lys Leu
    370                 375                 380

Gly Pro Trp Arg Arg Pro Val Ala Tyr Leu Ser Lys Lys Leu Asp Pro
385                 390                 395                 400

Val Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Leu Ala Pro His Ala Val Glu Ala Leu Val Lys Gln Pro Pro Asp
        435                 440                 445

Arg Trp Leu Ser Asn Ala Arg Met Thr His Tyr Gln Ala Leu Leu Leu
450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp Gln Pro
            500                 505                 510

Leu Pro Asp Ala Asp His Thr Trp Tyr Thr Asp Gly Ser Ser Leu Leu
        515                 520                 525

Gln Glu Gly Gln Arg Lys Ala Gly Ala Ala Val Thr Thr Glu Thr Glu
    530                 535                 540

Val Ile Trp Ala Lys Ala Leu Pro Ala Gly Thr Ser Ala Gln Arg Ala
545                 550                 555                 560

Glu Leu Ile Ala Leu Thr Gln Ala Leu Lys Met Ala Glu Gly Lys Lys
                565                 570                 575

Leu Asn Val Tyr Thr Asp Ser Arg Tyr Ala Phe Ala Thr Ala His Ile
            580                 585                 590

His Gly Glu Ile Tyr Arg Arg Arg Gly Leu Leu Thr Ser Glu Gly Lys
        595                 600                 605

Glu Ile Lys Asn Lys Asp Glu Ile Leu Ala Leu Leu Lys Ala Leu Phe
    610                 615                 620

Leu Pro Lys Arg Leu Ser Ile Ile His Cys Pro Gly His Gln Lys Gly
625                 630                 635                 640

His Ser Ala Glu Ala Arg Gly Asn Arg Met Ala Asp Gln Ala Ala Arg
                645                 650                 655

Lys Ala Ala Ile Thr Glu Thr Pro Asp Thr Ser Thr Leu Leu Ile
            660                 665                 670

<210> SEQ ID NO 2
<211> LENGTH: 510
<212> TYPE: PRT
<213> ORGANISM: Moloney murine leukemia virus

<400> SEQUENCE: 2

Leu Asn Ile Glu Asp Glu His Arg Leu His Glu Thr Ser Lys Glu Pro
1               5                   10                  15
```

-continued

```
Asp Val Ser Leu Gly Ser Thr Trp Leu Ser Asp Phe Pro Gln Ala Trp
         20                  25                  30
Ala Glu Thr Gly Gly Met Gly Leu Ala Val Arg Gln Ala Pro Leu Ile
             35                  40                  45
Ile Pro Leu Lys Ala Thr Ser Thr Pro Val Ser Ile Lys Gln Tyr Pro
 50                  55                  60
Met Ser Gln Glu Ala Arg Leu Gly Ile Lys Pro His Ile Gln Arg Leu
 65                  70                  75                  80
Leu Asp Gln Gly Ile Leu Val Pro Cys Gln Ser Pro Trp Asn Thr Pro
                 85                  90                  95
Leu Leu Pro Val Lys Lys Pro Gly Thr Asn Asp Tyr Arg Pro Val Gln
            100                 105                 110
Asp Leu Arg Glu Val Asn Lys Arg Val Glu Asp Ile His Pro Thr Val
            115                 120                 125
Pro Asn Pro Tyr Asn Leu Leu Ser Gly Leu Pro Pro Ser His Gln Trp
130                 135                 140
Tyr Thr Val Leu Asp Leu Lys Asp Ala Phe Phe Cys Leu Arg Leu His
145                 150                 155                 160
Pro Thr Ser Gln Pro Leu Phe Ala Phe Glu Trp Arg Asp Pro Glu Met
                165                 170                 175
Gly Ile Ser Gly Gln Leu Thr Trp Thr Arg Leu Pro Gln Gly Phe Lys
            180                 185                 190
Asn Ser Pro Thr Leu Phe Asp Glu Ala Leu His Arg Asp Leu Ala Asp
        195                 200                 205
Phe Arg Ile Gln His Pro Asp Leu Ile Leu Leu Gln Tyr Val Asp Asp
210                 215                 220
Leu Leu Leu Ala Ala Thr Ser Glu Leu Asp Cys Gln Gln Gly Thr Arg
225                 230                 235                 240
Ala Leu Leu Gln Thr Leu Gly Asn Leu Gly Tyr Arg Ala Ser Ala Lys
                245                 250                 255
Lys Ala Gln Ile Cys Gln Lys Gln Val Lys Tyr Leu Gly Tyr Leu Leu
            260                 265                 270
Lys Glu Gly Gln Arg Trp Leu Thr Glu Ala Arg Lys Glu Thr Val Met
            275                 280                 285
Gly Gln Pro Thr Pro Lys Thr Pro Arg Gln Leu Arg Glu Phe Leu Gly
290                 295                 300
Thr Ala Gly Phe Cys Arg Leu Trp Ile Pro Gly Phe Ala Glu Met Ala
305                 310                 315                 320
Ala Pro Leu Tyr Pro Leu Thr Lys Thr Gly Thr Leu Phe Asn Trp Gly
                325                 330                 335
Pro Asp Gln Gln Lys Ala Tyr Gln Glu Ile Lys Gln Ala Leu Leu Thr
            340                 345                 350
Ala Pro Ala Leu Gly Leu Pro Asp Leu Thr Lys Pro Phe Glu Leu Phe
            355                 360                 365
Val Asp Glu Lys Gln Gly Tyr Ala Lys Gly Val Leu Thr Gln Lys Leu
            370                 375                 380
Gly Pro Trp Arg Arg Pro Val Ala Tyr Leu Ser Lys Lys Leu Asp Pro
385                 390                 395                 400
Val Ala Ala Gly Trp Pro Pro Cys Leu Arg Met Val Ala Ala Ile Ala
                405                 410                 415
Val Leu Thr Lys Asp Ala Gly Lys Leu Thr Met Gly Gln Pro Leu Val
            420                 425                 430
```

```
Ile Leu Ala Pro His Ala Val Glu Ala Leu Val Lys Gln Pro Pro Asp
            435                 440                 445

Arg Trp Leu Ser Asn Ala Arg Met Thr His Tyr Gln Ala Leu Leu Leu
450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp
            500                 505                 510

<210> SEQ ID NO 3
<211> LENGTH: 161
<212> TYPE: PRT
<213> ORGANISM: Moloney murine leukemia virus

<400> SEQUENCE: 3

Gln Pro Leu Pro Asp Ala Asp His Thr Trp Tyr Thr Asp Gly Ser Ser
1               5                   10                  15

Leu Leu Gln Glu Gly Gln Arg Lys Ala Gly Ala Ala Val Thr Thr Glu
                20                  25                  30

Thr Glu Val Ile Trp Ala Lys Ala Leu Pro Ala Gly Thr Ser Ala Gln
            35                  40                  45

Arg Ala Glu Leu Ile Ala Leu Thr Gln Ala Leu Lys Met Ala Glu Gly
50                  55                  60

Lys Lys Leu Asn Val Tyr Thr Asp Ser Arg Tyr Ala Phe Ala Thr Ala
65                  70                  75                  80

His Ile His Gly Glu Ile Tyr Arg Arg Arg Gly Leu Leu Thr Ser Glu
                85                  90                  95

Gly Lys Glu Ile Lys Asn Lys Asp Glu Ile Leu Ala Leu Leu Lys Ala
            100                 105                 110

Leu Phe Leu Pro Lys Arg Leu Ser Ile Ile His Cys Pro Gly His Gln
        115                 120                 125

Lys Gly His Ser Ala Glu Ala Arg Gly Asn Arg Met Ala Asp Gln Ala
130                 135                 140

Ala Arg Lys Ala Ala Ile Thr Glu Thr Pro Asp Thr Ser Thr Leu Leu
145                 150                 155                 160

Ile

<210> SEQ ID NO 4
<211> LENGTH: 562
<212> TYPE: PRT
<213> ORGANISM: Human immunodeficiency virus 1

<400> SEQUENCE: 4

Asn Phe Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
                20                  25                  30

Ile Lys Ala Leu Val Glu Ile Cys Thr Glu Met Glu Lys Glu Gly Lys
            35                  40                  45

Ile Ser Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
```

```
                    85                  90                  95
Pro His Pro Ala Gly Leu Lys Lys Lys Ser Val Thr Val Leu Asp
                100                 105                 110

Val Gly Asp Ala Tyr Phe Ser Val Pro Leu Asp Glu Asp Phe Arg Lys
                115                 120                 125

Tyr Thr Ala Phe Thr Ile Pro Ser Ile Asn Asn Glu Thr Pro Gly Ile
            130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Asp Asp Leu Tyr Val Gly
                180                 185                 190

Ser Asp Leu Glu Ile Gly Gln His Arg Thr Lys Ile Glu Glu Leu Arg
                195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
                260                 265                 270

Tyr Pro Gly Ile Lys Val Arg Gln Leu Cys Lys Leu Leu Arg Gly Thr
            275                 280                 285

Lys Ala Leu Thr Glu Val Ile Pro Leu Thr Glu Glu Ala Glu Leu Glu
290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
                340                 345                 350

Thr Gly Lys Tyr Ala Arg Met Arg Gly Ala His Thr Asn Asp Val Lys
            355                 360                 365

Gln Leu Thr Glu Ala Val Gln Lys Ile Thr Thr Glu Ser Ile Val Ile
        370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Glu Pro Ile Val Gly Ala Glu Thr Phe Tyr Val Asp Gly Ala Ala
                435                 440                 445

Asn Arg Glu Thr Lys Leu Gly Lys Ala Gly Tyr Val Thr Asn Arg Gly
                450                 455                 460

Arg Gln Lys Val Val Thr Leu Thr Asp Thr Thr Asn Gln Lys Thr Glu
465                 470                 475                 480

Leu Gln Ala Ile Tyr Leu Ala Leu Gln Asp Ser Gly Leu Glu Val Asn
                485                 490                 495

Ile Val Thr Asp Ser Gln Tyr Ala Leu Gly Ile Ile Gln Ala Gln Pro
            500                 505                 510
```

Asp Gln Ser Glu Ser Glu Leu Val Asn Gln Ile Ile Glu Gln Leu Ile
             515                 520                 525

Lys Lys Glu Lys Val Tyr Leu Ala Trp Val Pro Ala His Lys Gly Ile
             530                 535                 540

Gly Gly Asn Glu Gln Val Asp Lys Leu Val Ser Ala Gly Ile Arg Lys
545                 550                 555                 560

Val Leu

<210> SEQ ID NO 5
<211> LENGTH: 437
<212> TYPE: PRT
<213> ORGANISM: Human immunodeficiency virus 1

<400> SEQUENCE: 5

Asn Phe Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Asp
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
        275                 280                 285

Lys Ala Leu Thr Glu Val Ile Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

```
Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val
        435

<210> SEQ ID NO 6
<211> LENGTH: 125
<212> TYPE: PRT
<213> ORGANISM: Human immunodeficiency virus 1

<400> SEQUENCE: 6

Gly Ala Glu Thr Phe Tyr Val Asp Gly Ala Ala Asn Arg Glu Thr Lys
1               5                   10                  15

Leu Gly Lys Ala Gly Tyr Val Thr Asn Arg Gly Arg Gln Lys Val Val
            20                  25                  30

Thr Leu Thr Asp Thr Thr Asn Gln Lys Thr Glu Leu Gln Ala Ile Tyr
        35                  40                  45

Leu Ala Leu Gln Asp Ser Gly Leu Glu Val Asn Ile Val Thr Asp Ser
    50                  55                  60

Gln Tyr Ala Leu Gly Ile Ile Gln Ala Gln Pro Asp Gln Ser Glu Ser
65                  70                  75                  80

Glu Leu Val Asn Gln Ile Ile Glu Gln Leu Ile Lys Lys Glu Lys Val
                85                  90                  95

Tyr Leu Ala Trp Val Pro Ala His Lys Gly Ile Gly Gly Asn Glu Gln
            100                 105                 110

Val Asp Lys Leu Val Ser Ala Gly Ile Arg Lys Val Leu
        115                 120                 125

<210> SEQ ID NO 7
<211> LENGTH: 166
<212> TYPE: PRT
<213> ORGANISM: Thermus thermophilus

<400> SEQUENCE: 7

Met Asn Pro Ser Pro Arg Lys Arg Val Ala Leu Phe Thr Asp Gly Ala
1               5                   10                  15

Cys Leu Gly Asn Pro Gly Pro Gly Gly Trp Ala Ala Leu Leu Arg Phe
            20                  25                  30

His Ala His Glu Lys Leu Leu Ser Gly Gly Glu Ala Cys Thr Thr Asn
        35                  40                  45

Asn Arg Met Glu Leu Lys Ala Ala Ile Glu Gly Leu Lys Ala Leu Lys
    50                  55                  60

Glu Pro Cys Glu Val Asp Leu Tyr Thr Asp Ser His Tyr Leu Lys Lys
65                  70                  75                  80
```

Ala Phe Thr Glu Gly Trp Leu Glu Gly Trp Arg Lys Arg Gly Trp Arg
                85                  90                  95

Thr Ala Glu Gly Lys Pro Val Lys Asn Arg Asp Leu Trp Glu Ala Leu
            100                 105                 110

Leu Leu Ala Met Ala Pro His Arg Val Arg Phe His Phe Val Lys Gly
        115                 120                 125

His Thr Gly His Pro Glu Asn Glu Arg Val Asp Arg Glu Ala Arg Arg
    130                 135                 140

Gln Ala Gln Ser Gln Ala Lys Thr Pro Cys Pro Pro Arg Ala Pro Thr
145                 150                 155                 160

Leu Phe His Glu Glu Ala
            165

<210> SEQ ID NO 8
<211> LENGTH: 224
<212> TYPE: PRT
<213> ORGANISM: Thermococcus litoralis

<400> SEQUENCE: 8

Met Asn Leu Gly Gly Ile Asp Glu Ala Gly Arg Gly Pro Val Ile Gly
1               5                   10                  15

Pro Leu Val Ile Ala Ala Val Val Asp Glu Ser Arg Met Gln Glu
            20                  25                  30

Leu Glu Ala Leu Gly Val Lys Asp Ser Lys Lys Leu Thr Pro Lys Arg
        35                  40                  45

Arg Glu Glu Leu Phe Glu Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
        115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
    210                 215                 220

<210> SEQ ID NO 9
<211> LENGTH: 680
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
            20                  25                  30

Ala Glu Thr Gly Gly Met Gly Leu Ala Val Arg Gln Ala Pro Leu Ile
        35                  40                  45

Ile Pro Leu Lys Ala Thr Ser Thr Pro Val Ser Ile Lys Gln Tyr Pro
    50                  55                  60

Met Ser Gln Glu Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Gly Leu Pro Pro Ser His Gln Trp
    130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
            260                 265                 270

Lys Glu Gly Gln Arg Trp Leu Thr Glu Ala Arg Lys Glu Thr Val Met
        275                 280                 285

Gly Gln Pro Thr Pro Lys Thr Pro Arg Gln Leu Arg Glu Phe Leu Gly
    290                 295                 300

Thr Ala Gly Phe Cys Arg Leu Trp Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
        355                 360                 365

Val Asp Glu Lys Gln Gly Tyr Ala Lys Gly Val Leu Thr Gln Lys Leu
    370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415
```

Val Leu Thr Lys Asp Ala Gly Lys Leu Thr Met Gly Gln Pro Leu Val
            420                 425                 430

Ile Leu Ala Pro His Ala Val Glu Ala Leu Val Lys Gln Pro Pro Asp
            435                 440                 445

Arg Trp Leu Ser Asn Ala Arg Met Thr His Tyr Gln Ala Leu Leu Leu
            450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
            485                 490                 495

Ile Leu Ala Glu Ala His Gly Thr Arg Pro Asp Leu Thr Asp Gln Pro
            500                 505                 510

Leu Pro Asp Asn Pro Ser Pro Arg Lys Arg Val Ala Leu Phe Thr Asn
            515                 520                 525

Gly Ala Cys Leu Gly Asn Pro Gly Pro Gly Gly Trp Ala Ala Leu Leu
            530                 535                 540

Arg Phe His Ala His Glu Lys Leu Leu Ser Gly Gly Glu Ala Cys Thr
545                 550                 555                 560

Thr Asn Asn Arg Met Glu Leu Lys Ala Ala Ile Glu Gly Leu Lys Ala
            565                 570                 575

Leu Lys Glu Pro Cys Glu Val Asp Leu Tyr Thr Asp Ser His Tyr Leu
            580                 585                 590

Lys Lys Ala Phe Thr Glu Gly Trp Leu Glu Gly Trp Arg Lys Arg Gly
            595                 600                 605

Trp Arg Thr Ala Glu Gly Lys Pro Val Lys Asn Arg Asp Leu Trp Glu
            610                 615                 620

Ala Leu Leu Leu Ala Met Ala Pro His Arg Val Arg Phe His Phe Val
625                 630                 635                 640

Lys Gly His Thr Gly His Pro Glu Asn Glu Arg Val Asp Arg Glu Ala
            645                 650                 655

Arg Arg Gln Ala Gln Ser Gln Ala Lys Thr Pro Cys Pro Pro Arg Ala
            660                 665                 670

Pro Thr Leu Phe His Glu Glu Ala
            675                 680

<210> SEQ ID NO 10
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
            20                  25                  30

Ala Glu Thr Gly Gly Met Gly Leu Ala Val Arg Gln Ala Pro Leu Ile
            35                  40                  45

Ile Pro Leu Lys Ala Thr Ser Thr Pro Val Ser Ile Lys Gln Tyr Pro
            50                  55                  60

Met Ser Gln Glu Ala Arg Leu Gly Ile Lys Pro His Ile Gln Arg Leu
65                  70                  75                  80

-continued

```
Leu Asp Gln Gly Ile Leu Val Pro Cys Gln Ser Pro Trp Asn Thr Pro
                    85                  90                  95

Leu Leu Pro Val Lys Lys Pro Gly Thr Asn Asp Tyr Arg Pro Val Gln
                100                 105                 110

Asp Leu Arg Glu Val Asn Lys Arg Val Glu Asp Ile His Pro Thr Val
            115                 120                 125

Pro Asn Pro Tyr Asn Leu Leu Ser Gly Leu Pro Pro Ser His Gln Trp
        130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
                180                 185                 190

Asn Ser Pro Thr Leu Phe Asp Glu Ala Leu His Arg Asp Leu Ala Asp
            195                 200                 205

Phe Arg Ile Gln His Pro Asp Leu Ile Leu Leu Gln Tyr Val Asp Asp
        210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
                260                 265                 270

Lys Glu Gly Gln Arg Trp Leu Thr Glu Ala Arg Lys Glu Thr Val Met
            275                 280                 285

Gly Gln Pro Thr Pro Lys Thr Pro Arg Gln Leu Arg Glu Phe Leu Gly
        290                 295                 300

Thr Ala Gly Phe Cys Arg Leu Trp Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
        355                 360                 365

Val Asp Glu Lys Gln Gly Tyr Ala Lys Gly Val Leu Thr Gln Lys Leu
            370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Leu Ala Pro His Ala Val Glu Ala Leu Val Lys Gln Pro Pro Asp
        435                 440                 445

Arg Trp Leu Ser Asn Ala Arg Met Thr His Tyr Gln Ala Leu Leu Leu
450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
            485                 490                 495

Ile Leu Ala Glu Ala His Gly Thr Arg Pro Asp Leu Thr Asp Gln Pro
```

```
                   500                 505                 510
Leu Pro Asp Lys Leu Gly Gly Ile Asn Gln Ala Gly Arg Gly Pro Val
            515                 520                 525

Ile Gly Pro Leu Val Ile Ala Ala Val Val Asp Glu Ser Arg Met
            530                 535                 540

Gln Glu Leu Glu Ala Leu Gly Val Lys Asp Ser Lys Lys Leu Thr Pro
545                 550                 555                 560

Lys Arg Arg Glu Glu Leu Phe Glu Ile Val Gln Ile Val Asp Asp
                    565                 570                 575

His Val Ile Ile Gln Leu Ser Pro Glu Glu Ile Asp Gly Arg Asp Gly
                580                 585                 590

Thr Met Asn Glu Leu Glu Ile Glu Asn Phe Ala Lys Ala Leu Asn Ser
            595                 600                 605

Leu Lys Val Lys Pro Asp Val Leu Tyr Ile Asp Ala Ala Asp Val Lys
            610                 615                 620

Glu Lys Arg Phe Gly Asp Ile Ile Gly Glu Arg Leu Ser Phe Ser Pro
625                 630                 635                 640

Lys Ile Ile Ala Glu His Lys Ala Asp Ser Lys Tyr Ile Pro Val Ala
                    645                 650                 655

Ala Ala Ser Ile Leu Ala Lys Val Thr Arg Asp Arg Ala Ile Glu Lys
                660                 665                 670

Leu Lys Glu Leu Tyr Gly Glu Ile Gly Ser Gly Tyr Pro Ser Asp Pro
            675                 680                 685

Asn Thr Arg Arg Phe Leu Glu Glu Tyr Tyr Lys Ala His Gly Glu Phe
            690                 695                 700

Pro Pro Ile Val Arg Lys Ser Trp Lys Thr Leu Arg Lys Ile Glu Glu
705                 710                 715                 720

Lys Leu Lys Ala Lys Lys Thr Gln Pro Thr Ile Leu Asp Phe Leu Lys
                    725                 730                 735

Lys Pro

<210> SEQ ID NO 11
<211> LENGTH: 602
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asn Phe Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
                20                  25                  30

Ile Lys Ala Leu Val Glu Ile Cys Thr Glu Met Glu Lys Glu Gly Lys
            35                  40                  45

Ile Ser Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Asp
                100                 105                 110
```

Val Gly Asp Ala Tyr Phe Ser Val Pro Leu Asp Glu Asp Phe Arg Lys
            115                 120                 125

Tyr Thr Ala Phe Thr Ile Pro Ser Ile Asn Asn Glu Thr Pro Gly Ile
130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
            165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
            195                 200                 205

Gln His Leu Leu Arg Trp Gly Leu Thr Thr Pro Asp Lys Lys His Gln
210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
            245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
            275                 280                 285

Lys Ala Leu Thr Glu Val Ile Pro Leu Thr Glu Glu Ala Glu Leu Glu
            290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
            325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
            355                 360                 365

Gln Leu Thr Glu Ala Val Gln Lys Ile Thr Thr Glu Ser Ile Val Ile
370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val Asn Pro Ser Pro Arg Lys Arg Val Ala Leu Phe
            435                 440                 445

Thr Asn Gly Ala Cys Leu Gly Asn Pro Gly Pro Gly Gly Trp Ala Ala
450                 455                 460

Leu Leu Arg Phe His Ala His Glu Lys Leu Leu Ser Gly Gly Glu Ala
465                 470                 475                 480

Cys Thr Thr Asn Asn Arg Met Glu Leu Lys Ala Ala Ile Glu Gly Leu
            485                 490                 495

Lys Ala Leu Lys Glu Pro Cys Glu Val Asp Leu Tyr Thr Asp Ser His
            500                 505                 510

Tyr Leu Lys Lys Ala Phe Thr Glu Gly Trp Leu Glu Gly Trp Arg Lys
            515                 520                 525

Arg Gly Trp Arg Thr Ala Glu Gly Lys Pro Val Lys Asn Arg Asp Leu

```
                    530                 535                 540

Trp Glu Ala Leu Leu Leu Ala Met Ala Pro His Arg Val Arg Phe His
545                 550                 555                 560

Phe Val Lys Gly His Thr Gly His Pro Glu Asn Glu Arg Val Asp Arg
                    565                 570                 575

Glu Ala Arg Arg Gln Ala Gln Ser Gln Ala Lys Thr Pro Cys Pro Pro
                580                 585                 590

Arg Ala Pro Thr Leu Phe His Glu Glu Ala
            595                 600

<210> SEQ ID NO 12
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asn Phe Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
                20                  25                  30

Ile Lys Ala Leu Val Glu Ile Cys Thr Glu Met Glu Lys Glu Gly Lys
            35                  40                  45

Ile Ser Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Asp
                100                 105                 110

Val Gly Asp Ala Tyr Phe Ser Val Pro Leu Asp Glu Asp Phe Arg Lys
            115                 120                 125

Tyr Thr Ala Phe Thr Ile Pro Ser Ile Asn Asn Glu Thr Pro Gly Ile
        130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
        275                 280                 285
```

Lys Ala Leu Thr Glu Val Ile Pro Leu Thr Glu Ala Glu Leu Glu
        290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val Lys Leu Gly Gly Ile Asn Gln Ala Gly Arg Gly
        435                 440                 445

Pro Val Ile Gly Pro Leu Val Ile Ala Ala Val Val Asp Glu Ser
450                 455                 460

Arg Met Gln Glu Leu Glu Ala Leu Gly Val Lys Asp Ser Lys Lys Leu
465                 470                 475                 480

Thr Pro Lys Arg Arg Glu Glu Leu Phe Glu Glu Ile Val Gln Ile Val
                485                 490                 495

Asp Asp His Val Ile Ile Gln Leu Ser Pro Glu Glu Ile Asp Gly Arg
            500                 505                 510

Asp Gly Thr Met Asn Glu Leu Glu Ile Glu Asn Phe Ala Lys Ala Leu
        515                 520                 525

Asn Ser Leu Lys Val Lys Pro Asp Val Leu Tyr Ile Asp Ala Ala Asp
    530                 535                 540

Val Lys Glu Lys Arg Phe Gly Asp Ile Ile Gly Glu Arg Leu Ser Phe
545                 550                 555                 560

Ser Pro Lys Ile Ile Ala Glu His Lys Ala Asp Ser Lys Tyr Ile Pro
                565                 570                 575

Val Ala Ala Ala Ser Ile Leu Ala Lys Val Thr Arg Asp Arg Ala Ile
            580                 585                 590

Glu Lys Leu Lys Glu Leu Tyr Gly Glu Ile Gly Ser Gly Tyr Pro Ser
        595                 600                 605

Asp Pro Asn Thr Arg Arg Phe Leu Glu Glu Tyr Tyr Lys Ala His Gly
    610                 615                 620

Glu Phe Pro Pro Ile Val Arg Lys Ser Trp Lys Thr Leu Arg Lys Ile
625                 630                 635                 640

Glu Glu Lys Leu Lys Ala Lys Lys Thr Gln Pro Thr Ile Leu Asp Phe
                645                 650                 655

Leu Lys Lys Pro
            660

<210> SEQ ID NO 13
<211> LENGTH: 707
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 13

```
Met Ile Asp Leu Gln Arg Pro Gln Ala Ala Thr Met Asp Ser Arg His
1               5                   10                  15

His His His His His Pro Trp Asp Tyr Lys Asp Asp Asp Asp Lys Pro
                20                  25                  30

Arg Trp Asn Ser Leu Asn Ile Glu Asp Glu His Arg Leu His Glu Thr
            35                  40                  45

Ser Lys Glu Pro Asp Val Ser Leu Gly Ser Thr Trp Leu Ser Asp Phe
    50                  55                  60

Pro Gln Ala Trp Ala Glu Thr Gly Gly Met Gly Leu Ala Val Arg Gln
65                  70                  75                  80

Ala Pro Leu Ile Ile Pro Leu Lys Ala Thr Ser Thr Pro Val Ser Ile
                85                  90                  95

Lys Gln Tyr Pro Met Ser Gln Glu Ala Arg Leu Gly Ile Lys Pro His
            100                 105                 110

Ile Gln Arg Leu Leu Asp Gln Gly Ile Leu Val Pro Cys Gln Ser Pro
        115                 120                 125

Trp Asn Thr Pro Leu Leu Pro Val Lys Lys Pro Gly Thr Asn Asp Tyr
    130                 135                 140

Arg Pro Val Gln Asp Leu Arg Glu Val Asn Lys Arg Val Glu Asp Ile
145                 150                 155                 160

His Pro Thr Val Pro Asn Pro Tyr Asn Leu Leu Ser Gly Leu Pro Pro
                165                 170                 175

Ser His Gln Trp Tyr Thr Val Leu Asp Leu Lys Asp Ala Phe Phe Cys
            180                 185                 190

Leu Arg Leu His Pro Thr Ser Gln Pro Leu Phe Ala Phe Glu Trp Arg
        195                 200                 205

Asp Pro Glu Met Gly Ile Ser Gly Gln Leu Thr Trp Thr Arg Leu Pro
    210                 215                 220

Gln Gly Phe Lys Asn Ser Pro Thr Leu Phe Asp Glu Ala Leu His Arg
225                 230                 235                 240

Asp Leu Ala Asp Phe Arg Ile Gln His Pro Asp Leu Ile Leu Leu Gln
                245                 250                 255

Tyr Val Asp Asp Leu Leu Leu Ala Ala Thr Ser Glu Leu Asp Cys Gln
            260                 265                 270

Gln Gly Thr Arg Ala Leu Leu Gln Thr Leu Gly Asn Leu Gly Tyr Arg
        275                 280                 285

Ala Ser Ala Lys Lys Ala Gln Ile Cys Gln Lys Gln Val Lys Tyr Leu
    290                 295                 300

Gly Tyr Leu Leu Lys Glu Gly Gln Arg Trp Leu Thr Glu Ala Arg Lys
305                 310                 315                 320

Glu Thr Val Met Gly Gln Pro Thr Pro Lys Thr Pro Arg Gln Leu Arg
                325                 330                 335

Glu Phe Leu Gly Thr Ala Gly Phe Cys Arg Leu Trp Ile Pro Gly Phe
            340                 345                 350

Ala Glu Met Ala Ala Pro Leu Tyr Pro Leu Thr Lys Thr Gly Thr Leu
        355                 360                 365

Phe Asn Trp Gly Pro Asp Gln Gln Lys Ala Tyr Gln Glu Ile Lys Gln
    370                 375                 380

Ala Leu Leu Thr Ala Pro Ala Leu Gly Leu Pro Asp Leu Thr Lys Pro
```

-continued

```
            385                 390                 395                 400
    Phe Glu Leu Phe Val Asp Glu Lys Gln Gly Tyr Ala Lys Gly Val Leu
                    405                 410                 415

Thr Gln Lys Leu Gly Pro Trp Arg Arg Pro Val Ala Tyr Leu Ser Lys
                420                 425                 430

Lys Leu Asp Pro Val Ala Ala Gly Trp Pro Pro Cys Leu Arg Met Val
                435                 440                 445

Ala Ala Ile Ala Val Leu Thr Lys Asp Ala Gly Lys Leu Thr Met Gly
    450                 455                 460

Gln Pro Leu Val Ile Leu Ala Pro His Ala Val Glu Ala Leu Val Lys
    465                 470                 475                 480

Gln Pro Pro Asp Arg Trp Leu Ser Asn Ala Arg Met Thr His Tyr Gln
                    485                 490                 495

Ala Leu Leu Leu Asp Thr Asp Arg Val Gln Phe Gly Pro Val Val Ala
                    500                 505                 510

Leu Asn Pro Ala Thr Leu Leu Pro Leu Pro Glu Glu Gly Leu Gln His
                515                 520                 525

Asn Cys Leu Asp Ile Leu Ala Glu Ala His Gly Thr Arg Pro Asp Leu
    530                 535                 540

Thr Asp Gln Pro Leu Pro Asp Ala Asp His Thr Trp Tyr Thr Asp Gly
    545                 550                 555                 560

Ser Ser Leu Leu Gln Glu Gly Gln Arg Lys Ala Gly Ala Ala Val Thr
                    565                 570                 575

Thr Glu Thr Glu Val Ile Trp Ala Lys Ala Leu Pro Ala Gly Thr Ser
                580                 585                 590

Ala Gln Arg Ala Glu Leu Ile Ala Leu Thr Gln Ala Leu Lys Met Ala
                595                 600                 605

Glu Gly Lys Lys Leu Asn Val Tyr Thr Asp Ser Arg Tyr Ala Phe Ala
    610                 615                 620

Thr Ala His Ile His Gly Glu Ile Tyr Arg Arg Arg Gly Leu Leu Thr
    625                 630                 635                 640

Ser Glu Gly Lys Glu Ile Lys Asn Lys Asp Glu Ile Leu Ala Leu Leu
                    645                 650                 655

Lys Ala Leu Phe Leu Pro Lys Arg Leu Ser Ile Ile His Cys Pro Gly
                660                 665                 670

His Gln Lys Gly His Ser Ala Glu Ala Arg Gly Asn Arg Met Ala Asp
                675                 680                 685

Gln Ala Ala Arg Lys Ala Ala Ile Thr Glu Thr Pro Asp Thr Ser Thr
    690                 695                 700

Leu Leu Ile
    705

<210> SEQ ID NO 14
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Ile Asp Leu Gln Arg Pro Gln Ala Ala Thr Met Asp Ser Arg His
1               5                   10                  15

His His His His Pro Trp Asp Tyr Lys Asp Asp Asp Lys Pro
            20                  25                  30
```

```
Arg Trp Asn Ser Leu Asn Ile Glu Asp Glu His Arg Leu His Glu Thr
         35                  40                  45

Ser Lys Glu Pro Asp Val Ser Leu Gly Ser Thr Trp Leu Ser Asp Phe
 50                  55                  60

Pro Gln Ala Trp Ala Glu Thr Gly Gly Met Gly Leu Ala Val Arg Gln
 65                  70                  75                  80

Ala Pro Leu Ile Ile Pro Leu Lys Ala Thr Ser Thr Pro Val Ser Ile
                 85                  90                  95

Lys Gln Tyr Pro Met Ser Gln Glu Ala Arg Leu Gly Ile Lys Pro His
             100                 105                 110

Ile Gln Arg Leu Leu Asp Gln Gly Ile Leu Val Pro Cys Gln Ser Pro
             115                 120                 125

Trp Asn Thr Pro Leu Leu Pro Val Lys Lys Pro Gly Thr Asn Asp Tyr
         130                 135                 140

Arg Pro Val Gln Asp Leu Arg Glu Val Asn Lys Arg Val Glu Asp Ile
145                 150                 155                 160

His Pro Thr Val Pro Asn Pro Tyr Asn Leu Leu Ser Gly Leu Pro Pro
                 165                 170                 175

Ser His Gln Trp Tyr Thr Val Leu Asp Leu Lys Asp Ala Phe Phe Cys
             180                 185                 190

Leu Arg Leu His Pro Thr Ser Gln Pro Leu Phe Ala Phe Glu Trp Arg
         195                 200                 205

Asp Pro Glu Met Gly Ile Ser Gly Gln Leu Thr Trp Thr Arg Leu Pro
210                 215                 220

Gln Gly Phe Lys Asn Ser Pro Thr Leu Phe Asp Glu Ala Leu His Arg
225                 230                 235                 240

Asp Leu Ala Asp Phe Arg Ile Gln His Pro Asp Leu Ile Leu Leu Gln
                 245                 250                 255

Tyr Val Asp Asp Leu Leu Leu Ala Ala Thr Ser Glu Leu Asp Cys Gln
             260                 265                 270

Gln Gly Thr Arg Ala Leu Leu Gln Thr Leu Gly Asn Leu Gly Tyr Arg
         275                 280                 285

Ala Ser Ala Lys Lys Ala Gln Ile Cys Gln Lys Gln Val Lys Tyr Leu
290                 295                 300

Gly Tyr Leu Leu Lys Glu Gly Gln Arg Trp Leu Thr Glu Ala Arg Lys
305                 310                 315                 320

Glu Thr Val Met Gly Gln Pro Thr Pro Lys Thr Pro Arg Gln Leu Arg
                 325                 330                 335

Glu Phe Leu Gly Thr Ala Gly Phe Cys Arg Leu Trp Ile Pro Gly Phe
             340                 345                 350

Ala Glu Met Ala Ala Pro Leu Tyr Pro Leu Thr Lys Thr Gly Thr Leu
         355                 360                 365

Phe Asn Trp Gly Pro Asp Gln Gln Lys Ala Tyr Gln Glu Ile Lys Gln
370                 375                 380

Ala Leu Leu Thr Ala Pro Ala Leu Gly Leu Pro Asp Leu Thr Lys Pro
385                 390                 395                 400

Phe Glu Leu Phe Val Asp Glu Lys Gln Gly Tyr Ala Lys Gly Val Leu
                 405                 410                 415

Thr Gln Lys Leu Gly Pro Trp Arg Arg Pro Val Ala Tyr Leu Ser Lys
             420                 425                 430

Lys Leu Asp Pro Val Ala Ala Gly Trp Pro Pro Cys Leu Arg Met Val
         435                 440                 445
```

```
Ala Ala Ile Ala Val Leu Thr Lys Asp Ala Gly Lys Leu Thr Met Gly
    450                 455                 460

Gln Pro Leu Val Ile Leu Ala Pro His Ala Val Glu Ala Leu Val Lys
465                 470                 475                 480

Gln Pro Pro Asp Arg Trp Leu Ser Asn Ala Arg Met Thr His Tyr Gln
                485                 490                 495

Ala Leu Leu Leu Asp Thr Asp Arg Val Gln Phe Gly Pro Val Val Ala
                500                 505                 510

Leu Asn Pro Ala Thr Leu Leu Pro Leu Pro Glu Glu Gly Leu Gln His
            515                 520                 525

Asn Cys Leu Asp Ile Leu Ala Glu Ala His Gly Thr Arg Pro Asp Leu
    530                 535                 540

Thr Asp Gln Pro Leu Pro Asp Asn Pro Ser Pro Arg Lys Arg Val Ala
545                 550                 555                 560

Leu Phe Thr Asn Gly Ala Cys Leu Gly Asn Pro Gly Pro Gly Gly Trp
                565                 570                 575

Ala Ala Leu Leu Arg Phe His Ala His Glu Lys Leu Leu Ser Gly Gly
                580                 585                 590

Glu Ala Cys Thr Thr Asn Asn Arg Met Glu Leu Lys Ala Ala Ile Glu
            595                 600                 605

Gly Leu Lys Ala Leu Lys Glu Pro Cys Glu Val Asp Leu Tyr Thr Asp
    610                 615                 620

Ser His Tyr Leu Lys Lys Ala Phe Thr Glu Gly Trp Leu Glu Gly Trp
625                 630                 635                 640

Arg Lys Arg Gly Trp Arg Thr Ala Glu Gly Lys Pro Val Lys Asn Arg
                645                 650                 655

Asp Leu Trp Glu Ala Leu Leu Leu Ala Met Ala Pro His Arg Val Arg
                660                 665                 670

Phe His Phe Val Lys Gly His Thr Gly His Pro Glu Asn Glu Arg Val
                675                 680                 685

Asp Arg Glu Ala Arg Arg Gln Ala Gln Ser Gln Ala Lys Thr Pro Cys
    690                 695                 700

Pro Pro Arg Ala Pro Thr Leu Phe His Glu Glu Ala
705                 710                 715

<210> SEQ ID NO 15
<211> LENGTH: 774
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Ile Asp Leu Gln Arg Pro Gln Ala Ala Thr Met Asp Ser Arg His
1               5                   10                  15

His His His His Pro Trp Asp Tyr Lys Asp Asp Asp Lys Pro
            20                  25                  30

Arg Trp Asn Ser Leu Asn Ile Glu Asp Glu His Arg Leu His Glu Thr
        35                  40                  45

Ser Lys Glu Pro Asp Val Ser Leu Gly Ser Thr Trp Leu Ser Asp Phe
    50                  55                  60

Pro Gln Ala Trp Ala Glu Thr Gly Gly Met Gly Leu Ala Val Arg Gln
65                  70                  75                  80

Ala Pro Leu Ile Ile Pro Leu Lys Ala Thr Ser Thr Pro Val Ser Ile
```

-continued

```
                85                  90                  95
Lys Gln Tyr Pro Met Ser Gln Glu Ala Arg Leu Gly Ile Lys Pro His
            100                 105                 110

Ile Gln Arg Leu Leu Asp Gln Gly Ile Leu Val Pro Cys Gln Ser Pro
            115                 120                 125

Trp Asn Thr Pro Leu Leu Pro Val Lys Lys Pro Gly Thr Asn Asp Tyr
        130                 135                 140

Arg Pro Val Gln Asp Leu Arg Glu Val Asn Lys Arg Val Glu Asp Ile
145                 150                 155                 160

His Pro Thr Val Pro Asn Pro Tyr Asn Leu Leu Ser Gly Leu Pro Pro
                165                 170                 175

Ser His Gln Trp Tyr Thr Val Leu Asp Leu Lys Asp Ala Phe Phe Cys
            180                 185                 190

Leu Arg Leu His Pro Thr Ser Gln Pro Leu Phe Ala Phe Glu Trp Arg
            195                 200                 205

Asp Pro Glu Met Gly Ile Ser Gly Gln Leu Thr Trp Thr Arg Leu Pro
        210                 215                 220

Gln Gly Phe Lys Asn Ser Pro Thr Leu Phe Asp Glu Ala Leu His Arg
225                 230                 235                 240

Asp Leu Ala Asp Phe Arg Ile Gln His Pro Asp Leu Ile Leu Leu Gln
                245                 250                 255

Tyr Val Asp Asp Leu Leu Leu Ala Ala Thr Ser Glu Leu Asp Cys Gln
            260                 265                 270

Gln Gly Thr Arg Ala Leu Leu Gln Thr Leu Gly Asn Leu Gly Tyr Arg
            275                 280                 285

Ala Ser Ala Lys Lys Ala Gln Ile Cys Gln Lys Gln Val Lys Tyr Leu
        290                 295                 300

Gly Tyr Leu Leu Lys Glu Gly Gln Arg Trp Leu Thr Glu Ala Arg Lys
305                 310                 315                 320

Glu Thr Val Met Gly Gln Pro Thr Pro Lys Thr Pro Arg Gln Leu Arg
                325                 330                 335

Glu Phe Leu Gly Thr Ala Gly Phe Cys Arg Leu Trp Ile Pro Gly Phe
            340                 345                 350

Ala Glu Met Ala Ala Pro Leu Tyr Pro Leu Thr Lys Thr Gly Thr Leu
            355                 360                 365

Phe Asn Trp Gly Pro Asp Gln Gln Lys Ala Tyr Gln Glu Ile Lys Gln
        370                 375                 380

Ala Leu Leu Thr Ala Pro Ala Leu Gly Leu Pro Asp Leu Thr Lys Pro
385                 390                 395                 400

Phe Glu Leu Phe Val Asp Glu Lys Gln Gly Tyr Ala Lys Gly Val Leu
                405                 410                 415

Thr Gln Lys Leu Gly Pro Trp Arg Arg Pro Val Ala Tyr Leu Ser Lys
            420                 425                 430

Lys Leu Asp Pro Val Ala Ala Gly Trp Pro Pro Cys Leu Arg Met Val
            435                 440                 445

Ala Ala Ile Ala Val Leu Thr Lys Asp Ala Gly Lys Leu Thr Met Gly
        450                 455                 460

Gln Pro Leu Val Ile Leu Ala Pro His Ala Val Glu Ala Leu Val Lys
465                 470                 475                 480

Gln Pro Pro Asp Arg Trp Leu Ser Asn Ala Arg Met Thr His Tyr Gln
                485                 490                 495

Ala Leu Leu Leu Asp Thr Asp Arg Val Gln Phe Gly Pro Val Val Ala
            500                 505                 510
```

```
Leu Asn Pro Ala Thr Leu Leu Pro Leu Pro Glu Glu Gly Leu Gln His
        515                 520                 525

Asn Cys Leu Asp Ile Leu Ala Glu Ala His Gly Thr Arg Pro Asp Leu
    530                 535                 540

Thr Asp Gln Pro Leu Pro Asp Lys Leu Gly Gly Ile Asn Gln Ala Gly
545                 550                 555                 560

Arg Gly Pro Val Ile Gly Pro Leu Val Ile Ala Ala Val Val Asp
                565                 570                 575

Glu Ser Arg Met Gln Glu Leu Glu Ala Leu Gly Val Lys Asp Ser Lys
                580                 585                 590

Lys Leu Thr Pro Lys Arg Arg Glu Glu Leu Phe Glu Glu Ile Val Gln
        595                 600                 605

Ile Val Asp Asp His Val Ile Ile Gln Leu Ser Pro Glu Glu Ile Asp
        610                 615                 620

Gly Arg Asp Gly Thr Met Asn Glu Leu Glu Ile Glu Asn Phe Ala Lys
625                 630                 635                 640

Ala Leu Asn Ser Leu Lys Val Lys Pro Asp Val Leu Tyr Ile Asp Ala
                645                 650                 655

Ala Asp Val Lys Glu Lys Arg Phe Gly Asp Ile Ile Gly Glu Arg Leu
                660                 665                 670

Ser Phe Ser Pro Lys Ile Ile Ala Glu His Lys Ala Asp Ser Lys Tyr
        675                 680                 685

Ile Pro Val Ala Ala Ala Ser Ile Leu Ala Lys Val Thr Arg Asp Arg
        690                 695                 700

Ala Ile Glu Lys Leu Lys Glu Leu Tyr Gly Glu Ile Gly Ser Gly Tyr
705                 710                 715                 720

Pro Ser Asp Pro Asn Thr Arg Arg Phe Leu Glu Glu Tyr Tyr Lys Ala
                725                 730                 735

His Gly Glu Phe Pro Pro Ile Val Arg Lys Ser Trp Lys Thr Leu Arg
                740                 745                 750

Lys Ile Glu Glu Lys Leu Lys Ala Lys Lys Thr Gln Pro Thr Ile Leu
        755                 760                 765

Asp Phe Leu Lys Lys Pro
        770

<210> SEQ ID NO 16
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Ile Asp Leu Gln Arg Pro Gln Ala Ala Thr Met Asp Ser Arg His
1               5                   10                  15

His His His His Pro Trp Asp Tyr Lys Asp Asp Asp Lys Pro
                20                  25                  30

Arg Trp Asn Ser Asn Phe Pro Ile Ser Pro Ile Glu Thr Val Pro Val
        35                  40                  45

Lys Leu Lys Pro Gly Met Asp Gly Pro Lys Val Lys Gln Trp Pro Leu
    50                  55                  60

Thr Glu Glu Lys Ile Lys Ala Leu Val Glu Ile Cys Thr Glu Met Glu
65                  70                  75                  80
```

-continued

```
Lys Glu Gly Lys Ile Ser Lys Ile Gly Pro Glu Asn Pro Tyr Asn Thr
             85                  90                  95

Pro Val Phe Ala Ile Lys Lys Asp Ser Thr Lys Trp Arg Lys Leu
            100                 105                 110

Val Asp Phe Arg Glu Leu Asn Lys Arg Thr Gln Asp Phe Trp Glu Val
            115                 120                 125

Gln Leu Gly Ile Pro His Pro Ala Gly Leu Lys Lys Lys Lys Ser Val
130                 135                 140

Thr Val Leu Asp Val Gly Asp Ala Tyr Phe Ser Val Pro Leu Asp Glu
145                 150                 155                 160

Asp Phe Arg Lys Tyr Thr Ala Phe Thr Ile Pro Ser Ile Asn Asn Glu
                165                 170                 175

Thr Pro Gly Ile Arg Tyr Gln Tyr Asn Val Leu Pro Gln Gly Trp Lys
            180                 185                 190

Gly Ser Pro Ala Ile Phe Gln Ser Ser Met Thr Lys Ile Leu Glu Pro
            195                 200                 205

Phe Arg Lys Gln Asn Pro Asp Ile Val Ile Tyr Gln Tyr Met Asp Asp
            210                 215                 220

Leu Tyr Val Gly Ser Asp Leu Glu Ile Gly Gln His Arg Thr Lys Ile
225                 230                 235                 240

Glu Glu Leu Arg Gln His Leu Leu Arg Trp Gly Leu Thr Thr Pro Asp
                245                 250                 255

Lys Lys His Gln Lys Glu Pro Pro Phe Leu Trp Met Gly Tyr Glu Leu
            260                 265                 270

His Pro Asp Lys Trp Thr Val Gln Pro Ile Val Leu Pro Glu Lys Asp
            275                 280                 285

Ser Trp Thr Val Asn Asp Ile Gln Lys Leu Val Gly Lys Leu Asn Trp
290                 295                 300

Ala Ser Gln Ile Tyr Pro Gly Ile Lys Val Arg Gln Leu Cys Lys Leu
305                 310                 315                 320

Leu Arg Gly Thr Lys Ala Leu Thr Glu Val Ile Pro Leu Thr Glu Glu
                325                 330                 335

Ala Glu Leu Glu Leu Ala Glu Asn Arg Glu Ile Leu Lys Glu Pro Val
            340                 345                 350

His Gly Val Tyr Tyr Asp Pro Ser Lys Asp Leu Ile Ala Glu Ile Gln
            355                 360                 365

Lys Gln Gly Gln Gly Gln Trp Thr Tyr Gln Ile Tyr Gln Glu Pro Phe
            370                 375                 380

Lys Asn Leu Lys Thr Gly Lys Tyr Ala Arg Met Arg Gly Ala His Thr
385                 390                 395                 400

Asn Asp Val Lys Gln Leu Thr Glu Ala Val Gln Lys Ile Thr Thr Glu
                405                 410                 415

Ser Ile Val Ile Trp Gly Lys Thr Pro Lys Phe Lys Leu Pro Ile Gln
            420                 425                 430

Lys Glu Thr Trp Glu Thr Trp Trp Thr Glu Tyr Trp Gln Ala Thr Trp
            435                 440                 445

Ile Pro Glu Trp Glu Phe Val Asn Thr Pro Pro Leu Val Lys Leu Trp
            450                 455                 460

Tyr Gln Leu Glu Lys Glu Pro Ile Val Asn Pro Ser Pro Arg Lys Arg
465                 470                 475                 480

Val Ala Leu Phe Thr Asn Gly Ala Cys Leu Gly Asn Pro Gly Pro Gly
                485                 490                 495

Gly Trp Ala Ala Leu Leu Arg Phe His Ala His Glu Lys Leu Leu Ser
```

```
                500               505               510
Gly Gly Glu Ala Cys Thr Thr Asn Asn Arg Met Glu Leu Lys Ala Ala
        515                 520                 525

Ile Glu Gly Leu Lys Ala Leu Lys Glu Pro Cys Glu Val Asp Leu Tyr
        530                 535                 540

Thr Asp Ser His Tyr Leu Lys Lys Ala Phe Thr Gly Trp Leu Glu
545                 550                 555                 560

Gly Trp Arg Lys Arg Gly Trp Arg Thr Ala Glu Gly Lys Pro Val Lys
                565                 570                 575

Asn Arg Asp Leu Trp Glu Ala Leu Leu Leu Ala Met Ala Pro His Arg
                580                 585                 590

Val Arg Phe His Phe Val Lys Gly His Thr Gly His Pro Glu Asn Glu
                595                 600                 605

Arg Val Asp Arg Glu Ala Arg Arg Gln Ala Gln Ser Gln Ala Lys Thr
        610                 615                 620

Pro Cys Pro Pro Arg Ala Pro Thr Leu Phe His Glu Glu Ala
625                 630                 635

<210> SEQ ID NO 17
<211> LENGTH: 696
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Ile Asp Leu Gln Arg Pro Gln Ala Ala Thr Met Asp Ser Arg His
1               5                   10                  15

His His His His Pro Trp Asp Tyr Lys Asp Asp Asp Lys Pro
            20                  25                  30

Arg Trp Asn Ser Asn Phe Pro Ile Ser Pro Ile Glu Thr Val Pro Val
        35                  40                  45

Lys Leu Lys Pro Gly Met Asp Gly Pro Lys Val Lys Gln Trp Pro Leu
    50                  55                  60

Thr Glu Glu Lys Ile Lys Ala Leu Val Glu Ile Cys Thr Glu Met Glu
65                  70                  75                  80

Lys Glu Gly Lys Ile Ser Lys Ile Gly Pro Glu Asn Pro Tyr Asn Thr
                85                  90                  95

Pro Val Phe Ala Ile Lys Lys Lys Asp Ser Thr Lys Trp Arg Lys Leu
            100                 105                 110

Val Asp Phe Arg Glu Leu Asn Lys Arg Thr Gln Asp Phe Trp Glu Val
        115                 120                 125

Gln Leu Gly Ile Pro His Pro Ala Gly Leu Lys Lys Lys Lys Ser Val
    130                 135                 140

Thr Val Leu Asp Val Gly Asp Ala Tyr Phe Ser Val Pro Leu Asp Glu
145                 150                 155                 160

Asp Phe Arg Lys Tyr Thr Ala Phe Thr Ile Pro Ser Ile Asn Asn Glu
                165                 170                 175

Thr Pro Gly Ile Arg Tyr Gln Tyr Asn Val Leu Pro Gln Gly Trp Lys
            180                 185                 190

Gly Ser Pro Ala Ile Phe Gln Ser Ser Met Thr Lys Ile Leu Glu Pro
        195                 200                 205

Phe Arg Lys Gln Asn Pro Asp Ile Val Ile Tyr Gln Tyr Met Asp Asp
    210                 215                 220
```

```
Leu Tyr Val Gly Ser Asp Leu Glu Ile Gly Gln His Arg Thr Lys Ile
225                 230                 235                 240

Glu Glu Leu Arg Gln His Leu Arg Trp Gly Leu Thr Thr Pro Asp
            245                 250                 255

Lys Lys His Gln Lys Glu Pro Pro Phe Leu Trp Met Gly Tyr Glu Leu
            260                 265                 270

His Pro Asp Lys Trp Thr Val Gln Pro Ile Val Leu Pro Glu Lys Asp
            275                 280                 285

Ser Trp Thr Val Asn Asp Ile Gln Lys Leu Val Gly Lys Leu Asn Trp
            290                 295                 300

Ala Ser Gln Ile Tyr Pro Gly Ile Lys Val Arg Gln Leu Cys Lys Leu
305                 310                 315                 320

Leu Arg Gly Thr Lys Ala Leu Thr Glu Val Ile Pro Leu Thr Glu Glu
                325                 330                 335

Ala Glu Leu Glu Leu Ala Glu Asn Arg Glu Ile Leu Lys Glu Pro Val
                340                 345                 350

His Gly Val Tyr Tyr Asp Pro Ser Lys Asp Leu Ile Ala Glu Ile Gln
            355                 360                 365

Lys Gln Gly Gln Gly Gln Trp Thr Tyr Gln Ile Tyr Gln Glu Pro Phe
370                 375                 380

Lys Asn Leu Lys Thr Gly Lys Tyr Ala Arg Met Arg Gly Ala His Thr
385                 390                 395                 400

Asn Asp Val Lys Gln Leu Thr Glu Ala Val Gln Lys Ile Thr Thr Glu
            405                 410                 415

Ser Ile Val Ile Trp Gly Lys Thr Pro Lys Phe Lys Leu Pro Ile Gln
            420                 425                 430

Lys Glu Thr Trp Glu Thr Trp Trp Thr Glu Tyr Trp Gln Ala Thr Trp
            435                 440                 445

Ile Pro Glu Trp Glu Phe Val Asn Thr Pro Pro Leu Val Lys Leu Trp
450                 455                 460

Tyr Gln Leu Glu Lys Glu Pro Ile Val Lys Leu Gly Gly Ile Asn Gln
465                 470                 475                 480

Ala Gly Arg Gly Pro Val Ile Gly Pro Leu Val Ile Ala Ala Val Val
                485                 490                 495

Val Asp Glu Ser Arg Met Gln Glu Leu Glu Ala Leu Gly Val Lys Asp
            500                 505                 510

Ser Lys Lys Leu Thr Pro Lys Arg Arg Glu Glu Leu Phe Glu Glu Ile
            515                 520                 525

Val Gln Ile Val Asp Asp His Val Ile Ile Gln Leu Ser Pro Glu Glu
            530                 535                 540

Ile Asp Gly Arg Asp Gly Thr Met Asn Glu Leu Glu Ile Glu Asn Phe
545                 550                 555                 560

Ala Lys Ala Leu Asn Ser Leu Lys Val Lys Pro Asp Val Leu Tyr Ile
                565                 570                 575

Asp Ala Ala Asp Val Lys Glu Lys Arg Phe Gly Asp Ile Gly Glu
            580                 585                 590

Arg Leu Ser Phe Ser Pro Lys Ile Ile Ala Glu His Lys Ala Asp Ser
            595                 600                 605

Lys Tyr Ile Pro Val Ala Ala Ala Ser Ile Leu Ala Lys Val Thr Arg
            610                 615                 620

Asp Arg Ala Ile Glu Lys Leu Lys Glu Leu Tyr Gly Glu Ile Gly Ser
625                 630                 635                 640
```

```
Gly Tyr Pro Ser Asp Pro Asn Thr Arg Arg Phe Leu Glu Glu Tyr Tyr
                645                 650                 655

Lys Ala His Gly Glu Phe Pro Pro Ile Val Arg Lys Ser Trp Lys Thr
            660                 665                 670

Leu Arg Lys Ile Glu Glu Lys Leu Lys Ala Lys Lys Thr Gln Pro Thr
        675                 680                 685

Ile Leu Asp Phe Leu Lys Lys Pro
    690                 695

<210> SEQ ID NO 18
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Ile Asp Leu Gln Arg Pro Gln Ala Ala Thr Met Asp Ser Arg His
1               5                   10                  15

His His His His Pro Trp Asp Tyr Lys Asp Asp Asp Lys Pro
            20                  25                  30

Arg Trp Asn Ser
        35

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Asp Asp Asp Lys
1               5

<210> SEQ ID NO 20
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

His His His His His His Pro Trp Asp Tyr Lys Asp Asp Asp Asp Lys
1               5                   10                  15

Pro Arg Trp Asn Ser
            20

<210> SEQ ID NO 21
<211> LENGTH: 166
<212> TYPE: PRT
<213> ORGANISM: Thermus thermophilus

<400> SEQUENCE: 21

Met Asn Pro Ser Pro Arg Lys Arg Val Ala Leu Phe Thr Asn Gly Ala
1               5                   10                  15

Cys Leu Gly Asn Pro Gly Pro Gly Gly Trp Ala Ala Leu Leu Arg Phe
            20                  25                  30
```

```
His Ala His Glu Lys Leu Leu Ser Gly Gly Glu Ala Cys Thr Thr Asn
            35                  40                  45

Asn Arg Met Glu Leu Lys Ala Ile Glu Gly Leu Lys Ala Leu Lys
50                  55                  60

Glu Pro Cys Glu Val Asp Leu Tyr Thr Asp Ser His Tyr Leu Lys Lys
65                  70                  75                  80

Ala Phe Thr Glu Gly Trp Leu Glu Gly Trp Arg Lys Arg Gly Trp Arg
                85                  90                  95

Thr Ala Glu Gly Lys Pro Val Lys Asn Arg Asp Leu Trp Glu Ala Leu
            100                 105                 110

Leu Leu Ala Met Ala Pro His Arg Val Arg Phe His Phe Val Lys Gly
        115                 120                 125

His Thr Gly His Pro Glu Asn Glu Arg Val Asp Arg Glu Ala Arg Arg
    130                 135                 140

Gln Ala Gln Ser Gln Ala Lys Thr Pro Cys Pro Pro Arg Ala Pro Thr
145                 150                 155                 160

Leu Phe His Glu Glu Ala
                165

<210> SEQ ID NO 22
<211> LENGTH: 224
<212> TYPE: PRT
<213> ORGANISM: Thermococcus litoralis

<400> SEQUENCE: 22

Met Asn Leu Gly Gly Ile Asn Gln Ala Gly Arg Gly Pro Val Ile Gly
1               5                   10                  15

Pro Leu Val Ile Ala Ala Val Val Asp Glu Ser Arg Met Gln Glu
            20                  25                  30

Leu Glu Ala Leu Gly Val Lys Asp Ser Lys Lys Leu Thr Pro Lys Arg
        35                  40                  45

Arg Glu Glu Leu Phe Glu Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
        115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
    210                 215                 220
```

<210> SEQ ID NO 23
<211> LENGTH: 895
<212> TYPE: PRT
<213> ORGANISM: Rous sarcoma virus

<400> SEQUENCE: 23

Thr Val Ala Leu His Leu Ala Ile Pro Leu Lys Trp Lys Pro Asp His
1               5                   10                  15

Thr Pro Val Trp Ile Asp Gln Trp Pro Leu Pro Glu Gly Lys Leu Val
            20                  25                  30

Ala Leu Thr Gln Leu Val Glu Lys Glu Leu Gln Leu Gly His Ile Val
        35                  40                  45

Pro Ser Leu Ser Cys Trp Asn Thr Pro Val Phe Val Ile Arg Lys Ala
    50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Val
145                 150                 155                 160

Val Gly Gln Val Leu Glu Pro Leu Arg Leu Lys His Pro Ser Leu Cys
                165                 170                 175

Met Leu His Tyr Met Asp Asp Leu Leu Leu Ala Ala Ser Ser His Asp
            180                 185                 190

Gly Leu Glu Ala Ala Gly Glu Glu Val Ile Ser Thr Leu Glu Arg Ala
        195                 200                 205

Gly Phe Thr Ile Ser Pro Asp Lys Val Gln Arg Glu Pro Gly Val Gln
    210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Gln
    290                 295                 300

Leu Ser Thr Thr Ala Ala Leu Glu Arg Trp Asp Pro Ala Leu Pro Leu
305                 310                 315                 320

Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
            340                 345                 350

Gln Pro Thr Lys Ala Phe Thr Ala Trp Leu Glu Val Leu Thr Leu Leu
        355                 360                 365

Ile Thr Lys Leu Arg Ala Ser Ala Val Arg Thr Phe Gly Lys Glu Val
    370                 375                 380

```
Asp Ile Leu Leu Leu Pro Ala Cys Phe Arg Glu Asp Leu Pro Leu Pro
385                 390                 395                 400

Glu Gly Ile Leu Leu Ala Leu Lys Gly Phe Ala Gly Lys Ile Arg Ser
            405                 410                 415

Ser Asp Thr Pro Ser Ile Phe Asp Ile Ala Arg Pro Leu His Val Ser
                420                 425                 430

Leu Lys Val Arg Val Thr Asp His Pro Val Pro Gly Pro Thr Val Phe
        435                 440                 445

Thr Asp Ala Ser Ser Ser Thr His Lys Gly Val Val Val Trp Arg Glu
450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                485                 490                 495

Thr Ala Pro Thr Asn Val Val Thr Asp Ser Ala Phe Val Ala Lys Met
                500                 505                 510

Leu Leu Lys Met Gly Gln Glu Gly Val Pro Ser Thr Ala Ala Ala Phe
            515                 520                 525

Ile Leu Glu Asp Ala Leu Ser Gln Arg Ser Ala Met Ala Ala Val Leu
530                 535                 540

His Val Arg Ser His Ser Glu Val Pro Gly Phe Phe Thr Glu Gly Asn
545                 550                 555                 560

Asp Val Ala Asp Ser Lys Ala Thr Phe Gln Ala Tyr Pro Leu Arg Glu
                565                 570                 575

Ala Lys Asp Leu His Thr Ala Leu His Ile Gly Pro Arg Ala Leu Ser
            580                 585                 590

Lys Ala Cys Asn Ile Ser Met Gln Gln Ala Arg Glu Val Val Gln Thr
                595                 600                 605

Cys Pro His Cys Asn Ser Ala Pro Ala Leu Glu Ala Gly Val Asn Pro
            610                 615                 620

Arg Gly Leu Gly Pro Leu Gln Ile Trp Gln Thr Asp Phe Thr Leu Glu
625                 630                 635                 640

Pro Arg Met Ala Pro Arg Ser Trp Leu Ala Val Thr Val Asp Thr Ala
                645                 650                 655

Ser Ser Ala Ile Val Val Thr Gln His Gly Arg Val Thr Ser Val Ala
                660                 665                 670

Ala Gln His His Trp Ala Thr Ala Ile Ala Val Leu Gly Arg Pro Lys
            675                 680                 685

Ala Ile Lys Thr Asp Asn Gly Ser Cys Phe Thr Ser Lys Ser Thr Arg
690                 695                 700

Glu Trp Leu Ala Arg Trp Gly Ile Ala His Thr Thr Gly Ile Pro Gly
705                 710                 715                 720

Asn Ser Gln Gly Gln Ala Met Val Glu Arg Ala Asn Arg Leu Leu Lys
                725                 730                 735

Asp Arg Ile Arg Val Leu Ala Glu Gly Asp Gly Phe Met Lys Arg Ile
                740                 745                 750

Pro Thr Ser Lys Gln Gly Glu Leu Leu Ala Lys Ala Met Tyr Ala Leu
            755                 760                 765

Asn His Phe Glu Arg Gly Glu Asn Thr Lys Thr Pro Ile Gln Lys His
            770                 775                 780

Trp Arg Pro Thr Val Leu Thr Glu Gly Pro Pro Val Lys Ile Arg Ile
785                 790                 795                 800

Glu Thr Gly Glu Trp Glu Lys Gly Trp Asn Val Leu Val Trp Gly Arg
```

```
                805                 810                 815
Gly Tyr Ala Ala Val Lys Asn Arg Asp Thr Asp Lys Val Ile Trp Val
            820                 825                 830

Pro Ser Arg Lys Val Lys Pro Asp Ile Thr Gln Lys Asp Glu Val Thr
            835                 840                 845

Lys Lys Asp Glu Ala Ser Pro Leu Phe Ala Gly Ile Ser Asp Trp Ile
    850                 855                 860

Pro Trp Glu Asp Glu Gln Glu Gly Leu Gln Gly Glu Thr Ala Ser Asn
865                 870                 875                 880

Lys Gln Glu Arg Pro Gly Glu Asp Thr Leu Ala Ala Asn Glu Ser
            885                 890                 895

<210> SEQ ID NO 24
<211> LENGTH: 900
<212> TYPE: PRT
<213> ORGANISM: Avian myeloblastosis virus type 1

<400> SEQUENCE: 24

Arg Ala Thr Val Leu Thr Val Ala Leu His Leu Ala Ile Pro Leu Lys
1               5                   10                  15

Trp Lys Pro Asn His Thr Pro Val Trp Ile Asp Gln Trp Pro Leu Pro
            20                  25                  30

Glu Gly Lys Leu Val Ala Leu Thr Gln Leu Val Glu Lys Glu Leu Gln
        35                  40                  45

Leu Gly His Ile Glu Pro Ser Leu Ser Cys Trp Asn Thr Pro Val Phe
    50                  55                  60

Val Ile Arg Lys Ala Ser Gly Ser Tyr Arg Leu Leu His Asp Leu Arg
65                  70                  75                  80

Ala Val Asn Ala Lys Leu Val Pro Phe Gly Ala Val Gln Gln Gly Ala
            85                  90                  95

Pro Val Leu Ser Ala Leu Pro Arg Gly Trp Pro Leu Met Val Leu Asp
        100                 105                 110

Leu Lys Asp Cys Phe Phe Ser Ile Pro Leu Ala Glu Gln Asp Arg Glu
    115                 120                 125

Ala Phe Ala Phe Thr Leu Pro Ser Val Asn Asn Gln Ala Pro Ala Arg
    130                 135                 140

Arg Phe Gln Trp Lys Val Leu Pro Gln Gly Met Thr Cys Ser Pro Thr
145                 150                 155                 160

Ile Cys Gln Leu Ile Val Gly Gln Ile Leu Glu Pro Leu Arg Leu Lys
                165                 170                 175

His Pro Ser Leu Arg Met Leu His Tyr Met Asp Asp Leu Leu Leu Ala
            180                 185                 190

Ala Ser Ser His Asp Gly Leu Glu Ala Ala Gly Glu Glu Val Ile Ser
        195                 200                 205

Thr Leu Glu Arg Ala Gly Phe Thr Ile Ser Pro Asp Lys Val Gln Arg
    210                 215                 220

Glu Pro Gly Val Gln Tyr Leu Gly Tyr Lys Leu Gly Ser Thr Tyr Val
225                 230                 235                 240

Ala Pro Val Gly Leu Val Ala Glu Pro Arg Ile Ala Thr Leu Trp Asp
                245                 250                 255

Val Gln Lys Leu Val Gly Ser Leu Gln Ser Val Arg Pro Ala Leu Gly
            260                 265                 270

Ile Pro Pro Arg Leu Met Gly Pro Phe Tyr Glu Gln Leu Arg Gly Ser
        275                 280                 285
```

```
Asp Pro Asn Glu Ala Arg Glu Trp Asn Leu Asp Met Lys Met Ala Trp
    290                 295                 300
Arg Glu Ile Val Gln Leu Ser Thr Thr Ala Ala Leu Glu Arg Trp Asp
305                 310                 315                 320
Pro Ala Leu Pro Leu Glu Gly Ala Val Ala Arg Cys Glu Gln Gly Ala
                325                 330                 335
Ile Gly Val Leu Gly Gln Gly Leu Ser Thr His Pro Arg Pro Cys Leu
            340                 345                 350
Trp Leu Phe Ser Thr Gln Pro Thr Lys Ala Phe Thr Ala Trp Leu Glu
        355                 360                 365
Val Leu Thr Leu Leu Ile Thr Lys Leu Arg Ala Ser Ala Val Arg Thr
370                 375                 380
Phe Gly Lys Glu Val Asp Ile Leu Leu Leu Pro Ala Cys Phe Arg Glu
385                 390                 395                 400
Asp Leu Pro Leu Pro Glu Gly Ile Leu Leu Ala Leu Arg Gly Phe Ala
                405                 410                 415
Gly Lys Ile Arg Ser Ser Asp Thr Pro Ser Ile Phe Asp Ile Ala Arg
            420                 425                 430
Pro Leu His Val Ser Leu Lys Val Arg Val Thr Asp His Pro Val Pro
        435                 440                 445
Gly Pro Thr Val Phe Thr Asp Ala Ser Ser Ser Thr His Lys Gly Val
    450                 455                 460
Val Val Trp Arg Glu Gly Pro Arg Trp Glu Ile Lys Glu Ile Ala Asp
465                 470                 475                 480
Leu Gly Ala Ser Val Gln Gln Leu Glu Ala Arg Ala Val Ala Met Ala
                485                 490                 495
Leu Leu Leu Trp Pro Thr Thr Pro Thr Asn Val Val Thr Asp Ser Ala
            500                 505                 510
Phe Val Ala Lys Met Leu Leu Lys Met Gly Gln Glu Gly Val Pro Ser
        515                 520                 525
Thr Ala Ala Ala Phe Ile Leu Glu Asp Ala Leu Ser Gln Arg Ser Ala
    530                 535                 540
Met Ala Ala Val Leu His Val Arg Ser His Ser Glu Val Pro Gly Phe
545                 550                 555                 560
Phe Thr Glu Gly Asn Asp Val Ala Asp Ser Gln Ala Thr Phe Gln Ala
                565                 570                 575
Tyr Pro Leu Arg Glu Ala Lys Asp Leu His Thr Ala Leu His Ile Gly
            580                 585                 590
Pro Arg Ala Leu Ser Lys Ala Cys Asn Ile Ser Met Gln Gln Ala Arg
        595                 600                 605
Glu Val Val Gln Thr Cys Pro His Cys Asn Ser Ala Pro Ala Leu Glu
    610                 615                 620
Ala Gly Val Asn Pro Arg Gly Leu Gly Pro Leu Gln Ile Trp Gln Thr
625                 630                 635                 640
Asp Phe Thr Leu Glu Pro Arg Met Ala Pro Arg Ser Trp Leu Ala Val
                645                 650                 655
Thr Val Asp Thr Ala Ser Ser Ala Ile Val Val Thr Gln His Gly Arg
            660                 665                 670
Val Thr Ser Val Ala Ala Gln His His Trp Ala Thr Ala Ile Ala Val
        675                 680                 685
Leu Gly Arg Pro Lys Ala Ile Lys Thr Asp Asn Gly Ser Cys Phe Thr
    690                 695                 700
Ser Lys Ser Thr Arg Glu Trp Leu Ala Arg Trp Gly Ile Ala His Thr
```

-continued

```
                705                 710                 715                 720
Thr Gly Ile Pro Gly Asn Ser Gln Gly Gln Ala Met Val Glu Arg Ala
                    725                 730                 735

Asn Arg Leu Leu Lys Asp Lys Ile Arg Val Leu Ala Glu Gly Asp Gly
            740                 745                 750

Phe Met Lys Arg Ile Pro Thr Ser Lys Gln Gly Glu Leu Leu Ala Lys
        755                 760                 765

Ala Met Tyr Ala Leu Asn His Phe Glu Arg Gly Glu Asn Thr Lys Thr
    770                 775                 780

Pro Ile Gln Lys His Trp Arg Pro Thr Val Leu Thr Glu Gly Pro Pro
785                 790                 795                 800

Val Lys Ile Arg Ile Glu Thr Gly Glu Trp Glu Lys Gly Trp Asn Val
                805                 810                 815

Leu Val Trp Gly Arg Gly Tyr Ala Ala Val Lys Asn Arg Asp Thr Asp
            820                 825                 830

Lys Val Ile Trp Val Pro Ser Arg Lys Val Lys Pro Asp Ile Thr Gln
        835                 840                 845

Lys Asp Glu Val Thr Lys Lys Asp Glu Ala Ser Pro Leu Phe Ala Gly
    850                 855                 860

Ile Ser Asp Trp Ala Pro Trp Glu Gly Glu Gln Gly Leu Gln Glu
865                 870                 875                 880

Glu Thr Ala Ser Asn Lys Gln Glu Arg Pro Gly Glu Asp Thr Pro Ala
                885                 890                 895

Ala Asn Glu Ser
            900

<210> SEQ ID NO 25
<211> LENGTH: 901
<212> TYPE: PRT
<213> ORGANISM: Avian myeloblastosis virus type 2

<400> SEQUENCE: 25

Gly Arg Ala Thr Val Phe Thr Val Ala Leu His Leu Ala Ile Pro Leu
1               5                   10                  15

Lys Trp Lys Pro Asp His Thr Pro Val Trp Ile Asp Gln Trp Pro Leu
            20                  25                  30

Pro Glu Gly Lys Leu Val Ala Leu Thr Gln Leu Val Glu Lys Glu Leu
        35                  40                  45

Gln Leu Gly His Ile Glu Pro Ser Leu Ser Cys Trp Asn Thr Pro Val
    50                  55                  60

Phe Val Ile Arg Lys Ala Ser Gly Ser Tyr Arg Leu Leu His Asp Leu
65                  70                  75                  80

Arg Ala Val Asn Ala Lys Leu Val Pro Phe Gly Ala Val Gln Gln Gly
                85                  90                  95

Ala Pro Val Leu Ser Ala Leu Pro Arg Gly Trp Pro Leu Met Val Leu
            100                 105                 110

Asp Leu Lys Asp Cys Phe Phe Ser Ile Pro Leu Ala Glu Gln Asp Arg
        115                 120                 125

Glu Ala Phe Ala Phe Thr Leu Pro Ser Val Asn Asn Gln Ala Pro Ala
    130                 135                 140

Arg Arg Phe Gln Trp Lys Val Leu Pro Gln Gly Met Thr Cys Ser Pro
145                 150                 155                 160

Thr Ile Cys Gln Leu Ile Val Gly Gln Ile Leu Glu Pro Leu Arg Leu
                165                 170                 175
```

```
Lys His Pro Ser Leu Arg Met Leu His Tyr Met Asp Asp Leu Leu Leu
                180                 185                 190

Ala Ala Ser Ser His Asp Gly Leu Glu Ala Ala Gly Glu Glu Val Ile
            195                 200                 205

Ser Thr Leu Glu Arg Ala Gly Phe Thr Ile Ser Pro Asp Lys Val Gln
        210                 215                 220

Lys Glu Pro Gly Val Gln Tyr Leu Gly Tyr Lys Leu Gly Ser Thr Tyr
225                 230                 235                 240

Val Ala Pro Val Gly Leu Val Ala Glu Pro Arg Ile Ala Thr Leu Trp
                245                 250                 255

Asp Val Gln Lys Leu Val Gly Ser Leu Gln Ser Val Arg Pro Ala Leu
            260                 265                 270

Gly Ile Pro Pro Arg Leu Met Gly Pro Phe Tyr Glu Gln Leu Arg Gly
        275                 280                 285

Ser Asp Pro Asn Glu Ala Arg Glu Trp Asn Leu Asp Met Lys Met Ala
290                 295                 300

Trp Arg Glu Ile Val Gln Leu Ser Thr Thr Ala Ala Leu Glu Arg Trp
305                 310                 315                 320

Asp Pro Ala Leu Pro Leu Glu Gly Ala Val Ala Arg Cys Glu Gln Gly
                325                 330                 335

Ala Ile Gly Val Leu Gly Gln Gly Leu Ser Thr His Pro Arg Pro Cys
            340                 345                 350

Leu Trp Leu Phe Ser Thr Gln Pro Thr Lys Ala Phe Thr Ala Trp Leu
        355                 360                 365

Glu Val Leu Thr Leu Leu Ile Thr Lys Leu Arg Ala Ser Ala Val Arg
370                 375                 380

Thr Phe Gly Lys Glu Val Asp Ile Leu Leu Pro Ala Cys Phe Arg
385                 390                 395                 400

Glu Asp Leu Pro Leu Pro Glu Gly Ile Leu Leu Ala Leu Arg Gly Phe
                405                 410                 415

Ala Gly Lys Ile Arg Ser Ser Asp Thr Pro Ser Ile Phe Asp Ile Ala
            420                 425                 430

Arg Pro Leu His Val Ser Leu Lys Val Arg Val Thr Asp His Pro Val
        435                 440                 445

Pro Gly Pro Thr Val Phe Thr Asp Ala Ser Ser Thr His Lys Gly
450                 455                 460

Val Val Val Trp Arg Glu Gly Pro Arg Trp Glu Ile Lys Glu Ile Ala
465                 470                 475                 480

Asp Leu Gly Ala Ser Val Gln Gln Leu Glu Ala Arg Ala Val Ala Met
                485                 490                 495

Ala Leu Leu Leu Trp Pro Thr Thr Pro Thr Asn Val Val Thr Asp Ser
            500                 505                 510

Ala Phe Val Ala Lys Met Leu Leu Lys Met Gly Gln Glu Gly Val Pro
        515                 520                 525

Ser Thr Ala Ala Ala Phe Ile Leu Glu Asp Ala Leu Ser Gln Arg Ser
530                 535                 540

Ala Met Ala Ala Val Leu His Val Arg Ser His Ser Glu Val Pro Gly
545                 550                 555                 560

Phe Phe Thr Glu Gly Asn Asp Val Ala Asp Ser Gln Ala Thr Phe Gln
                565                 570                 575

Ala Tyr Pro Leu Arg Glu Ala Lys Asp Leu His Thr Ala Leu His Ile
            580                 585                 590

Gly Pro Arg Ala Leu Ser Lys Ala Cys Asn Ile Ser Met Gln Gln Ala
```

```
                595                 600                 605
Arg Glu Val Val Gln Thr Cys Pro His Cys Asn Ser Ala Pro Ala Leu
610                 615                 620

Glu Ala Gly Val Asn Pro Arg Gly Leu Gly Pro Leu Gln Ile Trp Gln
625                 630                 635                 640

Thr Asp Phe Thr Leu Glu Pro Arg Met Ala Pro Arg Ser Trp Leu Ala
                645                 650                 655

Val Thr Val Asp Thr Ala Ser Ser Ala Ile Val Val Thr Gln His Gly
                660                 665                 670

Arg Val Thr Ser Val Ala Ala Gln His His Trp Ala Thr Ala Ile Ala
                675                 680                 685

Val Leu Gly Arg Pro Lys Ala Ile Lys Thr Asp Asn Gly Ser Cys Phe
690                 695                 700

Thr Ser Lys Ser Thr Arg Glu Trp Leu Ala Arg Trp Gly Ile Ala His
705                 710                 715                 720

Thr Thr Gly Ile Pro Gly Asn Ser Gln Gly Gln Ala Met Val Glu Arg
                725                 730                 735

Ala Asn Arg Leu Leu Lys Asp Lys Ile Arg Val Leu Ala Glu Gly Asp
                740                 745                 750

Gly Phe Met Lys Arg Ile Pro Thr Ser Lys Gln Gly Glu Leu Leu Ala
                755                 760                 765

Lys Ala Val Tyr Ala Leu Asn His Phe Glu Arg Gly Glu Asn Thr Lys
770                 775                 780

Thr Pro Ile Gln Lys His Trp Arg Pro Thr Val Leu Thr Glu Gly Pro
785                 790                 795                 800

Pro Val Lys Ile Arg Ile Glu Thr Gly Glu Trp Glu Lys Gly Trp Asn
                805                 810                 815

Val Leu Val Trp Gly Arg Gly Tyr Ala Ala Val Lys Asn Arg Asp Thr
                820                 825                 830

Asp Lys Val Ile Trp Val Pro Ser Arg Lys Val Lys Pro Asp Ile Thr
                835                 840                 845

Gln Lys Asp Glu Val Thr Lys Arg Asp Glu Ala Ser Pro Leu Phe Ala
850                 855                 860

Gly Ile Ser Asp Trp Ala Pro Trp Glu Gly Glu Gln Glu Gly Leu Gln
865                 870                 875                 880

Glu Glu Thr Ala Ser Asn Lys Gln Glu Arg Pro Gly Glu Asp Thr Leu
                885                 890                 895

Ala Ala Asn Glu Ser
            900

<210> SEQ ID NO 26
<211> LENGTH: 895
<212> TYPE: PRT
<213> ORGANISM: Rous-associated virus type 2

<400> SEQUENCE: 26

Thr Val Ala Leu His Leu Ala Ile Pro Leu Lys Trp Lys Pro Asp His
1               5                   10                  15

Thr Pro Val Trp Ile Asp Gln Trp Pro Leu Pro Glu Gly Lys Leu Val
                20                  25                  30

Ala Val Thr Gln Leu Val Glu Lys Glu Leu Gln Leu Gly His Ile Glu
            35                  40                  45

Pro Ser Leu Ser Cys Trp Asn Thr Pro Val Phe Val Ile Arg Lys Ala
        50                  55                  60
```

```
Ser Gly Ser Tyr Arg Leu Leu His Asp Leu Arg Ala Val Asn Ala Lys
 65                  70                  75                  80

Leu Val Pro Phe Gly Ala Val Gln Gln Gly Ala Pro Val Leu Ser Ala
                 85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Val
145                 150                 155                 160

Val Gly Gln Val Leu Glu Pro Leu Arg Leu Lys His Pro Ala Leu Arg
                165                 170                 175

Met Leu His Tyr Met Asp Asp Leu Leu Leu Ala Ala Ser Ser His Asp
            180                 185                 190

Gly Leu Glu Ala Ala Gly Lys Glu Val Ile Gly Thr Leu Glu Arg Ala
        195                 200                 205

Gly Phe Thr Ile Ser Pro Asp Lys Ile Gln Arg Glu Pro Gly Val Gln
    210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Gln
    290                 295                 300

Leu Ser Thr Thr Ala Ala Leu Glu Arg Trp Asp Pro Ala Gln Pro Leu
305                 310                 315                 320

Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
            340                 345                 350

Gln Pro Thr Lys Ala Phe Thr Ala Trp Leu Glu Val Leu Thr Leu Leu
        355                 360                 365

Ile Thr Lys Leu Arg Ala Ser Ala Val Arg Thr Phe Gly Lys Glu Val
    370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Arg Gly Phe Ala Gly Lys Ile Arg Ser
                405                 410                 415

Ser Asp Thr Pro Ser Ile Phe Asp Ile Ala Arg Pro Leu His Val Ser
            420                 425                 430

Leu Lys Val Arg Val Thr Asp His Pro Val Pro Gly Pro Thr Val Phe
        435                 440                 445

Thr Asp Ala Ser Ser Ser Thr His Lys Gly Val Val Val Trp Arg Glu
    450                 455                 460

Gly Pro Arg Trp Glu Ile Lys Glu Ile Val Asp Leu Gly Ala Ser Val
465                 470                 475                 480

Gln Gln Leu Glu Ala Arg Ala Val Ala Met Ala Leu Leu Leu Trp Pro
```

```
            485                 490                 495
Thr Thr Pro Thr Asn Val Val Thr Asp Ser Ala Phe Val Ala Lys Met
            500                 505                 510
Leu Leu Lys Met Gly Gln Glu Gly Val Pro Ser Thr Ala Ala Ala Phe
            515                 520                 525
Ile Leu Glu Asp Ala Leu Ser Gln Arg Ser Ala Met Ala Ala Val Leu
            530                 535                 540
His Val Arg Ser His Ser Glu Val Pro Gly Phe Phe Thr Glu Gly Asn
545                 550                 555                 560
Asp Val Ala Asp Ser Gln Ala Thr Phe Gln Ala Tyr Pro Leu Arg Glu
                565                 570                 575
Ala Lys Asp Leu His Thr Ala Leu His Ile Gly Pro Arg Ala Leu Ser
                580                 585                 590
Lys Ala Cys Asn Ile Ser Met Gln Gln Ala Arg Glu Val Val Gln Thr
                595                 600                 605
Cys Pro His Cys Asn Ser Ala Pro Ala Leu Glu Ala Gly Val Asn Pro
            610                 615                 620
Arg Gly Leu Gly Pro Leu Gln Ile Trp Gln Thr Asp Phe Thr Leu Glu
625                 630                 635                 640
Pro Arg Met Ala Pro Arg Ser Trp Leu Ala Val Thr Val Asp Thr Ala
                645                 650                 655
Ser Ser Ala Ile Val Val Thr Gln His Gly Arg Val Thr Ser Val Ala
            660                 665                 670
Ala Gln His His Trp Ala Thr Ala Ile Ala Val Leu Gly Arg Pro Lys
                675                 680                 685
Ala Ile Lys Thr Asp Asn Gly Ser Cys Phe Thr Ser Lys Ser Thr Arg
            690                 695                 700
Glu Trp Leu Ala Arg Trp Gly Ile Ala His Thr Thr Gly Ile Pro Gly
705                 710                 715                 720
Asn Ser Gln Gly Gln Ala Met Val Glu Arg Ala Asn Arg Leu Leu Lys
                725                 730                 735
Asp Lys Ile Arg Val Leu Ala Glu Gly Asp Gly Phe Met Lys Arg Ile
            740                 745                 750
Pro Ala Ser Lys Gln Gly Glu Leu Leu Ala Lys Ala Met Tyr Ala Leu
            755                 760                 765
Asn His Phe Glu Arg Gly Glu Asn Thr Lys Thr Pro Val Gln Lys His
            770                 775                 780
Trp Arg Pro Thr Val Leu Thr Glu Gly Pro Pro Val Lys Ile Arg Ile
785                 790                 795                 800
Glu Thr Gly Glu Trp Glu Lys Gly Trp Asn Val Leu Val Trp Gly Arg
                805                 810                 815
Gly Tyr Ala Ala Val Lys Asn Arg Asp Thr Asp Lys Val Ile Trp Val
                820                 825                 830
Pro Ser Arg Lys Val Lys Pro Asp Ile Thr Gln Lys Asp Glu Val Thr
            835                 840                 845
Lys Lys Asp Glu Ala Ser Pro Leu Phe Ala Gly Ser Ser Asp Trp Ile
            850                 855                 860
Pro Trp Gly Asp Glu Gln Glu Gly Leu Gln Glu Glu Ala Ala Ser Asn
865                 870                 875                 880
Lys Gln Glu Gly Pro Gly Glu Asp Thr Leu Ala Ala Asn Glu Ser
                885                 890                 895

<210> SEQ ID NO 27
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Glu Ala Ala Ala Lys
1               5
```